(12) United States Patent
Teverovskiy et al.

(10) Patent No.: US 7,461,048 B2
(45) Date of Patent: Dec. 2, 2008

(54) SYSTEMS AND METHODS FOR TREATING, DIAGNOSING AND PREDICTING THE OCCURRENCE OF A MEDICAL CONDITION

(75) Inventors: Mikhail Teverovskiy, Harrison, NY (US); David A. Verbel, New York, NY (US); Olivier Saidi, Greenwich, CT (US)

(73) Assignee: Aureon Laboratories, Inc., Yonkers, NY (US)

( * ) Notice: Subject to any disclaimer, the term of this patent is extended or adjusted under 35 U.S.C. 154(b) by 0 days.

(21) Appl. No.: 11/581,052

(22) Filed: Oct. 13, 2006

(65) Prior Publication Data

US 2007/0099219 A1 May 3, 2007

Related U.S. Application Data

(63) Continuation-in-part of application No. 11/080,360, filed on Mar. 14, 2005, which is a continuation-in-part of application No. 11/067,066, filed on Feb. 25, 2005, now Pat. No. 7,321,881, said application No. 11/080,360 is a continuation-in-part of application No. 10/991,897, filed on Nov. 17, 2004, said application No. 11/080,360 and a continuation-in-part of application No. 10/991,240, filed on Nov. 17, 2004, is a continuation-in-part of application No. 10/624,233, filed on Jul. 21, 2003, now Pat. No. 6,995,020.

(60) Provisional application No. 60/520,939, filed on Nov. 18, 2003, provisional application No. 60/548,322, filed on Feb. 27, 2004, provisional application No. 60/577,051, filed on Jun. 4, 2004, provisional application No. 60/520,815, filed on Nov. 17, 2003, provisional application No. 60/552,497, filed on Mar. 12, 2004, provisional application No. 60/577,051, filed on Jun. 4, 2004, provisional application No. 60/600,764, filed on Aug. 11, 2004, provisional application No. 60/620,514, filed on Oct. 20, 2004, provisional application No. 60/645,158, filed on Jan. 18, 2005, provisional application No. 60/651,779, filed on Feb. 9, 2005, provisional application No. 60/726,809, filed on Oct. 13, 2005.

(51) Int. Cl.
*G06F 15/00* (2006.01)
*G06F 15/18* (2006.01)

(52) U.S. Cl. .............................. 706/62; 706/21; 435/7.23

(58) Field of Classification Search ....................... None
See application file for complete search history.

(56) References Cited

U.S. PATENT DOCUMENTS 5,993,388 A * 11/1999 Kattan et al. ................. 600/300

(Continued)

*Primary Examiner*—Michael B Holmes
(74) *Attorney, Agent, or Firm*—Mintz, Levin, Cohn, Ferris, Glovsky & Popeo, P.C.

(57) ABSTRACT

Methods and systems are provided that use clinical information, molecular information and computer-generated morphometric information in a predictive model for predicting the occurrence (e.g., recurrence) of a medical condition, for example, cancer. In an embodiment, a model that predicts prostate cancer recurrence is provided, where the model is based on features including seminal vesicle involvement, surgical margin involvement, lymph node status, androgen receptor (AR) staining index of tumor, a morphometric measurement of epithelial nuclei, and at least one morphometric measurement of stroma. In another embodiment, a model that predicts clinical failure post prostatectomy is provided, wherein the model is based on features including biopsy Gleason score, lymph node involvement, prostatectomy Gleason score, a morphometric measurement of epithelial cytoplasm, a morphometric measurement of epithelial nuclei, a morphometric measurement of stroma, and intensity of androgen receptor (AR) in racemase (AMACR)-positive epithelial cells.

33 Claims, 18 Drawing Sheets

U.S. PATENT DOCUMENTS

| | | | |
|---|---|---|---|
| 6,409,664 B1* | 6/2002 | Kattan et al. | 600/300 |
| 6,410,043 B1* | 6/2002 | Steiner et al. | 424/422 |
| 6,413,533 B1* | 7/2002 | Steiner et al. | 424/422 |
| 6,413,535 B1* | 7/2002 | Steiner et al. | 424/422 |
| 6,545,034 B1* | 4/2003 | Carson et al. | 514/411 |
| 6,545,139 B1* | 4/2003 | Thompson et al. | 536/23.5 |
| 6,828,429 B1* | 12/2004 | Srivastava et al. | 536/23.1 |
| 6,906,320 B2* | 6/2005 | Sachs et al. | 250/282 |
| 6,949,342 B2* | 9/2005 | Golub et al. | 435/6 |
| 7,052,908 B2* | 5/2006 | Chang | 435/325 |
| 7,071,303 B2* | 7/2006 | Lin | 530/350 |
| 7,105,560 B1* | 9/2006 | Carson et al. | 514/411 |
| 7,105,561 B2* | 9/2006 | Carson et al. | 514/411 |
| 7,129,262 B2* | 10/2006 | Carson et al. | 514/411 |
| 7,151,100 B1* | 12/2006 | Carson et al. | 514/232.8 |
| 7,189,752 B2* | 3/2007 | Carson et al. | 514/411 |
| 7,211,599 B2* | 5/2007 | Carson et al. | 514/411 |
| 7,229,774 B2* | 6/2007 | Chinnaiyan et al. | 435/7.1 |
| 7,245,748 B2* | 7/2007 | Degani et al. | 382/128 |
| 7,321,881 B2* | 1/2008 | Saidi et al. | 706/21 |
| 7,332,290 B2* | 2/2008 | Rubin et al. | 435/7.1 |
| 7,361,680 B2* | 4/2008 | Carson et al. | 514/411 |
| 7,393,921 B2* | 7/2008 | Lin | 530/350 |

OTHER PUBLICATIONS

Raf kinase inhibitor protein: a putative molecular target in prostate cancer Singh, S.; Malik, B.K.; Sharma, D.K.; India Annual Conference, 2004. Proceedings of the IEEE INDICON 2004. First Dec. 20-22, 2004 pp. 406-409 Digital Object Identifier 10.1109/INDICO.2004.1497783.*

Improving risk grouping rules for prostate cancer patients with optimization Churilov, L.; Bagirov, A.M.; Schwartz, D.; Smith, K.; Dally, M.; System Sciences, 2004. Proceedings of the 37th Annual Hawaii International Conference on Jan. 5-8, 2004 pp. 9 pp. Digital Object Identifier 10.1109/HICSS.2004.1265355.*

MRI alone simulation for conformal radiation therapy of prostate cancer: technical aspects Pasquier, D.; Betrouni, N.; Vermandel, M.; Lacornerie, T.; Lartigau, E.; Rousseau, J.; Engineering in Medicine and Biology Society, 2006. EMBS '06. 28th Annual International Conference of the IEEE Aug. 2006 pp. 160-163.*

A Model-Aided Segmentation in Urethra Identification Based on an Atlas Human Autopsy Image for Intensity Modulated Radiation Therapy Yan Song; Muller, B.; Burman, C.; Mychalcazk, B.; Yulin Song; Engineering in Medicine and Biology Society, 2007. EMBS 2007. 29th Annual International Conference of the IEEE Aug. 22-26, 2007 pp. 3532-3535.*

Automatic detection of three radio-opaque markers for prostate targeting using EPID during external radiation therapy Pouliot, S.; Zaccarin, A.; Laurendeau, D.; Pouliot, J.; Image Processing, 2001. Proceedings. 2001 International Conference on vol. 2, Oct. 7-10, 2001 pp. 857-860 vol. 2 Digital Object Identifier 10.1109/ICIP.2001.958629.*

MRI alone simulation for conformal radiation therapy of prostate cancer: technical aspects Pasquier, D.; Betrouni, N.; Vermandel, M.; Lacornerie, T.; Lartigau, E.; Rousseau, J.; Engineering in Medicine and Biology Society, 2006. EMBS '06. 28th Annual International Conference of the IEEE Aug. 30, 2006-Sep. 3, 2006 pp. 160-163.*

Ultrasonic multifeature tissue characterization for the early detection of prostate cancer Scheipers, U.; Lorenz, A.; Pesavento, A.; Ermert, H.; Sommerfeld, H.-J.; Garcia-Schurmann, M.; Kuhne, K.; Senge, T.; Philippou, S.; Ultrasonics Symposium, 2001 IEEE vol. 2, Oct. 7-10, 2001 pp. 1265-1268 vol. 2.*

Ablameyko, S., et al. "From cell image segmentation to differential diagnosis of thyroid cancer", Pattern Recognition, 2002. Proceedings. 16th International Conference on Quebec City, Que., Canada Aug. 11-15, 2002, Los Alamitos, CA, USA, IEEE Compout. Soc, Us, vol. 1, Aug. 11, 2002, pp. 763-766.

Antonini, M., et al., "Image coding using wavelet transform," *IEEE Trans. Image Process.*, vol. 1, pp. 205-220, 1992.

Baatz, M., et al., "Multiresolution Segmentation—An Optimization Approach for High Quality Multi-scale Image Segmentation," In *Angewandte Geographische Informationsverarbeitung* XII, Strobl, J., Blaschke, T., Griesebner, G. (eds.), Wichmann—Verlag, Heidelberg, pp. 12-23, 2000.

Berry, DA, Cirrincione C, Henderson IC, et al. Estrogen-receptor status and outcomes of modern chemotherapy for patients with node-positive breast cancer. *Jama* 2006;295:1658-6714.

Biganzoli, E., et al. Feed forward neural networks for the analysis of censored survival data: a partial logistic regression approach. *Stat Med*, 1998.

Brown, et al. Knowledge-based analysis of microarray gene expression data by using support vector machines. Proc Natl Acad Sci U S A 97:262-7, 2000.

Brown, S.F., et al. On the use of artificial neural networks for the analysis of survival data. *IEEE Trans. on Neural Networks*, 8(5):1071-1077, 1997.

Burke, H.B., et al. Artificial neural networks improve the accuracy of cancer survival prediction. *Cancer*, 97(4): pp. 857-862, 1997.

Camp, R., G. G. Chung, and D. L. Rimm, "Automated subcellular localization and quantification of protein expression in tissue microarrays," *Nature Medicine*, vol. 8, pp. 1323-1327, 2002.

Chen, CD, Welsbie DS, Tran C, et al. Molecular determinants of resistance to antiandrogen therapy. Nat Med 2004; 10:33-91.

Cooperberg, MR, Broering JM, Litwin MS, et al. The contemporary management of prostate cancer in the United States: lessons from the cancer of the prostate strategic urologic research endeavor (CapSURE), a national disease registry. J Urol 2004;171:1393-4014.

Office Action corresponding to U.S. Appl. No. 10/991,240, mailed May 28, 2008, 22 pgs.

Daubechies, I., *Ten Lectures on Wavelets*, SIAM, Philadelphia, PA, 1992, pp. 198-202 and pp. 254-256.

Davidow, E., et al. Advancing drug discovery through systems biology. *Drug Discov Today*, 8:175-183, 2003.

Definiens, Cellenger Architecture: A Technical Review, Apr. 2004.

deSilva, C.J.S., et al. Artificial neural networks and breast cancer prognosis. *Australian Comput. J.* 26:78-81, 1994.

Dhanasekaran, S.M., Barrette, T.R., Ghosh, D., Shah, R., Varambally, S., Kurachi, K., Pienta, K.J., Rubin, M.A., and Chinnaiyan, A.M. 2001. Delineation of prognostic biomarkers in prostate cancer. Nature 412:822-826.

Diamond, J., et al., "The use of morphological characteristics and texture analysis in the identification of tissue composition in prostatic neoplasia," *Human Pathology*, vol. 35, pp. 1121-1131, 2004.

Duda, R.O., et al., *Pattern Classification*, 2nd ed. Wiley, New York, 2001, pp. 483-484.

Egmont-Petersen, M. et al., "Image Processing with Neural Networks-a-Review", Pattern Recognition, Elsevier, Kidlington, GB, vol. 35, No. 10, Oct. 2002, pp. 2279-2301.

Eskelinen, M., Lipponen, P., Majapuro, R., and Syrjanen, K. 1991. Prognostic factors in prostatic adenocarcinoma assessed by means of quantitative histology. Eur Urol 19:274-278.

Fayyad, U.M., et al. Knowledge Discovery and Data Mining : Towards a unifying framework. In *Proceedings of the Second International Conference on Knowledge Discovery and Data Mining*, Portland, 1996. AAAI Press.

Freedland, S.J., Humphreys, E.B., Mangold, L.A., Eisenberger, M., Dorey, F.J., Walsh, P.C., and Partin, A.W. 2005. Risk of prostate cancer-specific mortality following biochemical recurrence after radical prostatectomy. Jama 294:433-439.

Freiha, F.S., McNeal, J.E., and Stamey, T.A. 1988. Selection criteria for radical prostatectomy based on morphometric studies in prostate carcinoma. NCI Monogr: 107-108.

Fukunaga, K., *Introduction to Statistical Pattern Recognition*, 2nd ed. New York: Academic, 1990, p. 125.

Gonzales, R.C. et al., *Digital Image Processing*. Addison-Wesley, New York, 1992, pp. 173-185.

Gordon, A., A. Colman-Lerner, T. E. Chin, K. R. Benjamin, R. C. Yu, and R. Brent, "Single-cell quantification of molecules and rates using open-source microscope-based cytometry," Nature Methods, vol. 4, pp. 175-181, 2007.

Graefen, M., et al. Validation study of the accuracy of a postoperative nomogram for recurrence after radical prostatectomy for localized prostate cancer. *Journal of Clin Oncol*, 20:951-956, 2002.

Graefen, M., et al. A validation of two preoperative nomograms predicting recurrence following radical prostatectomy in a cohort of European men. Urol Oncol 7:141-6, 2002.

Graefen, M., et al. International validation of a preoperative nomogram for prostate cancer recurrence after radical prostatectomy. J. Clin Oncol 20:3206-12, 2002.

Gronberg, H. Prostate cancer epidemiology, *Lancet*, 361:859-864, 2003.

Guyon, I, et al. Gene selection for cancer classification using support vector machines. Machine Learning 1:S316-22, 2002.

Halabi, S, et al. Prognostic model for predicting survival in men with hormone-refractory metastatic prostate cancer. J. Clin Oncol 21:1232-7, 2003.

Hameed, O, Humphrey PA. Immunohistochemistry in diagnostic surgical pathology of the prostate. Semin Diagn Pathol 2005;22:88-1041.

Harashima, K, Akimoto T, Nonaka T, Tsuzuki K, Mitsuhashi N, Nakano T. Heat shock protein 90 (Hsp90) chaperone complex inhibitor, radicicol, potentiated radiation-induced cell killing in a hormone-sensitive prostate cancer cell line through degradation of the androgen receptor. Int J Radiat Biol 2005;81:63-761.

Harlan, William S. "Optimization of a Neural Network", Feb. 1999 (5 pp.) accessed at http://billharlan.com/pub/papers/neural/ on Mar. 1, 2006.

Harrell, F.E. et al. Evaluating the yield of medical tests. *JAMA*, 247(18):2543-2546, 1982.

Harrell, F.E., Regression Modeling Strategies, Springer-Verlag 2001, pp. 247 and 493.

Hood, L. Systems biology: integrating technology, biology, and computation. *Mech Ageing Dev*, 124:9-16, 2003.

Huggins, C, Hodges CV. Studies on prostate cancer: I: The effect of castration, of estrogen and of androgen injection on serum phosphatases in metastatic carcinoma of the prostate. The Journal of Urology, vol. 168, pp. 9-12, Jul. 2002.

Hull, GW, Rabbani F, Abbas F, Wheeler TM, Kattan MW, Scardino PT. Cancer control with radical prostatectomy alone in 1,000 consecutive patients. J Urol 2002;167:528-342 Pt 1.

Hurwitz, M.D., DeWeese, T.L., Zinreich, E.S., Epstein, J.I., and Partin, A.W. 1999. Nuclear morphometry predicts disease-free interval for clinically localized adenocarcinoma of the prostate treated with definitive radiation therapy. Int J Cancer 84:594-597.

Idekar, T., Galitski, T., and Hood, L. 2001. A new approach to decoding life: systems biology. Annu Rev Genomics Hum Genet 2:343-372.(2001).

Inoue, T., Segawa, T., Shiraishi, T., Yoshida, T., Toda, Y., Yamada, T., Kinukawa, N., Kinoshita, H., Kamoto, T., and Ogawa, O. 2005. Androgen receptor, Ki67, and p53 expression in radical prostatectomy specimens predict treatment failure in Japanese population. Urology 66:332-337.

International Search Report dated Dec. 19, 2005, corresponding to PCT/US2005/008350.

International Search Report for PCT/US04/38778, Mailed Jul. 2, 2008, 1 pg.

Jacquin, A.E. "Fractal image coding: A review, "*Proc. IEEE*, vol. 81, 1451-1465, 1993.

Jafari-Khouzani, K. et al. "Multiwavelet grading of pathological images of prostate," *IEEE Trans. Biomed. Eng.*, vol. 50, pp. 697-704, 2003.

Johansson, JE, Andren O, Andersson SO, et al. Natural history of early, localized prostate cancer. Jama 2004; 291:2713-2719.

Kaplan, E.L., et al. (1958), "nonparametric Estimation from Incomplete Observations," JASA, 53, pp. 457-481.

Kattan, M.W., et al. Experiments to determine whether recursive partitioning or an artificial neural network overcomes theoretical limitation of cox proportional hazards regression. *Comput Biomed Res*, 31(5):363-373, 1998.

Kattan, M.W., et al. Postoperative nomogram for disease recurrence after radical prostatectomy for prostate cancer. *Journal of Clin Oncol*, 17:1499-1507, 1999.

Kattan, M.W., et al. << A preoperative nomogram for disease recurrence following radical prostatectomy for prostate cancer. J. Natl. Cancer Inst. 90:766-771, 1998.

Kim, K.S. et al., "Automatic classification of cells using morphological shape in peripheral blood images", Proceedings of the SPIE—the international society for optical engineering spie-int. soc. Opt. eng USA, vol. 4210, 2000, (290-298 pp).

Klein, J.P., et al. *Survival Analysis: Techniques for Censored and Truncated Data*. Springer, New York, 1997, pp. 247-335.

Krtolica, A., C. O. de Solorzano, S. Lockett and J. Campisi, "Quantification of epithelial cells in coculture with fibroblast by fluorescence image analysis," Cytometry, vol. 49, pp. 73-82, 2002.

Laine, A. et al., "Texture classification by wavelet packet signatures," *IEEE Trans. Pattern Anal. Machine Intell.*, vol. 15, pp. 1186-1191, 1993.

Landini, G. "Applications of fractal geometry in pathology," in *Fractal Geometry in Biological Systems: An Analytical Approach*, P.M. Iannaccone and M. Kohokha, Eds. CRC Press, Boca Raton, FL, 1996, pp. 205-246.

LaTulippe, E., Satagopan, J., Smith, A., Scher, H., Scardino, P., Reuter, V., and Gerald, W.L. 2002. Comprehensive gene expression analysis of prostate cancer reveals distinct transcriptional programs associated with metastatic disease. Cancer Res 62:4499-4506.

Li, H, Luan Y. Kernel Cox regression models for linking gene expression profiles to censored survival data. *Pac Symp Biocomput* 2003:65-76.

Li, R., Wheeler, T., Dai, H., Frolov, A., Thompson, T., and Ayala, G. 2004. High level of androgen receptor is associated with aggressive clinicopathologic features and decreased biochemical recurrence-free survival in prostate: cancer patients treated with radical prostatectomy. Am J Surg Pathol 28:928-934 (2004).

Lin, Y, Kokontis J, Tang F, et al. Androgen and its receptor promote Bax-mediated apoptosis. Mol Cell Biol 2006;26:1908-165.

Liu, D.C., et al. On the limited memory bfgs method for large scale optimization. *Mathematical Programming*, 45:503-528, 1989.

Lu, N., *Fractal Imaging*. Academic, San Diego, CA 1997.

Luo, J., Duggan, D.J., Chen, Y., Sauvageot, J., Ewing, C.M., Bittner, M.L., Trent, J.M., and Isaacs, W.B. 2001. Human prostate cancer and benign prostatic hyperplasia: molecular dissection by gene expression profiling. Cancer Res 61:4683-4688 (2001).

Luo, J.H., Yu, Y.P., Cieply, K., Lin, F., Deflavia, P., Dhir, R., Finkelstein, S., Michalopoulos, G., and Becich, M. 2002. Gene expression analysis of prostate cancers. Mol Carcinog 33:25-35 (2002).

Messing EM, Manola J, Sarosdy M, Wilding G, Crawford ED, Trump D. Immediate hormonal therapy compared with observation after radical prostatectomy and pelvic lymphadenectomy in men with node-positive prostate cancer. N Engl J Med 341:1781-824 (1999).

Messing EM, Thompson I, Jr. Follow-up of conservatively managed prostate cancer: watchful waiting and primary hormonal therapy. Urol Clin North Am 30:687-702, viii4 (2003).

Mohler, JL, et al. Nuclear roundness factor measurement for assessment of prognosis of patients with prostatic carcinoma. I. Testing of a digitization system. J. Urol 139:1080-4, 1988.

Molinaro, A. et al., Tree-based Multivariate Regression and Density Estimation with Right-Censored Data. University of California, U.C. Berkeley Division of Biostatistics Working Paper Series, 2003, 1-50.

Moul JW, Wu H, Sun L, et al. Early versus delayed hormonal therapy for prostate specific antigen only recurrence of prostate cancer after radical prostatectomy. J Urol 171:1141-73 (2004).

Ohno-Machado, L., et al. Modular neural networks for medical prognosis: Quantifying the benefits of combining neural networks for survival prediction. *Connection Science*, 9:71-86, 1997.

Olinici, CD, et al. Computer-based image analysis of nucleoli in prostate carcinoma. Rom J. Morphol Embryol 43:163-7, 1997.

Osuna, E.E. et al. Support Vector Machines : Training and Applications. A.I. Memo 1602/C.B.C.L. Paper 144, MIT, 1997.

Partin, AW, et al. Use of nuclear morphometry, Gleason histologic scoring, clinical stage, and age predict disease-free survival among patients with prostate cancer. Cancer 70:161-168, 1992.

Rakotomamonjy, A., Variable Selection Using SVM-based Criteria, J of Machine Learning Research, 2003; (3)1357-1370.

Ramaswamy, S., Ross, K.N., Lander, E.S., and Golub, T.R. 2003. A molecular signature of metastasis in primary solid tumors. Nat Genet 33:49-54 (2003).

Rao, J.Y., D. Seligson, and G. P. Hemstreet, Protein expression analysis using quantitative fluorescence image analysis on tissue microarray slides, BioTechniques, vol. 32:924-932 (2002).

Rhodes, D.R., Barrette, T.R., Rubin, M.A., Ghosh, D., and Chinnaiyan, A.M. 2002. Meta-analysis of microarrays: interstudy validation of gene expression profiles reveals pathway dysregulation in prostate cancer. Cancer Res 62:4427-4433 (2002).

Roula, M.A. et al., "A multispectral computer vision system for automatic grading of prostatic neoplasia," in *Proc. IEEE Int. Symp. Biomed. Imaging*, Washington, DC, 2002, pp. 193-196.

Rubin, MA, Bismar TA, Andren O, Mucci L, Kim R, Shen R, Ghosh D, Wei J, Chinnaiyan A, Adami O, Kantoff P, Johansson J-E. Decreased a-methylacyl CoA racemase expression in localized prostate cancer is associated with an increased rate of biochemical recurrence and cancer-specific death. Cancer Epid Bio Prev 2005; 14:1424-1432.

Sabino, D.M.U. et al., "Toward leukocyte recognition using morphometry, texture and color", Biomedical Imaging: Macro To Nano, 2004. IEEE Internantional Symposium on Arlington Va, USA Apr. 15-18, 2004, Piscataway, NJ USA, IEEE, Apr. 15, 2004, pp. 121-124.

Sadi, MV, Barrack ER. Androgen receptors and growth fraction in metastatic prostate cancer as predictors of time to tumor progression after hormonal therapy. Cancer Surv 11:195-215 (1991).

Sadi, MV, Barrack ER. Image analysis of androgen receptor immunostaining in metastatic prostate cancer. Heterogeneity as a predictor of response to hormonal therapy. Cancer 71:2574-2580 (1993).

Scher, HI, et al. Clinical states in prostate cancer: towards a dynamic model of disease progression. Urology 55:323-327, 2000.

Schoelkopf, B. et al., "Comparing Support Vector Machines With Gaussian Kernels to Radial Basis Function Classifiers", IEEE Transactions on Signal Processing, IEEE Service Center, New York, NY, US, vol. 45, No. 11, Nov. 1997, pp. 2758-2765.

Schouten, B.A.M. et al., "Feature extraction using fractal codes," in *Proc. Int. Conf. Visual Information and Information Systems*, Amsterdam, 1999, pp. 483-492.

Sharifi, N, Gulley JL, Dahut WL. Androgen deprivation therapy for prostate cancer. Jama 2005;294:238-442.

Singh, D., Febbo, P.G., Ross, K., Jackson, D.G., Manola, J., Ladd, C., Tamayo, P., Renshaw A.A., D'Amico, A.V., Richie, J.P., et al. 2002. Gene expression correlates of clinical prostate cancer behavior. Cancer Cell 1:203-209.

Sloan, A. "Retrieving database contents by image recognition: New fractal power," *Advanced Imaging*, vol. 5, pp. 26-30, 1994.

Smaletz, O, et al., Nomogram for overall survival of patients with progressive metastatic prostate cancer after castration. J. Clin Oncol 20:3972-82, 2002.

Smith, Y. et al., "Similarity measurement method for the classification of architecturally differentiated images," *Comp. Biomed. Res.*, vol. 32, pp. 1-12, 1999.

Smola, A. et al., A Tutorial on Support Vector Regression, NeuroCOLT2 Technical Report Series NCE-TR-1998-030, 1998, 1-73.

Snow, P. et al. Artificial neural networks in the diagnosis and prognosis of prostate cancer: a pilot study. *J. Urology*, 152(5):1923-1926, 1997.

Stephenson AJ, Scardino PT, Eastham JA, Bianco F, Dotan ZA, Fearn PA, Kattan M. Preoperative nomogram predicting the 10-year probability of prostate cancer recurrence after radical prostatectomy. *J Natl Cancer Inst* 2006 98:715-717.

Stephenson AJ, Scardino PT, Eastham JA, et al. Postoperative nomogram predicting the 10-year probability of prostate cancer recurrence after radical prostatectomy. J Clin Oncol, 23:7005-12 (2005).

Stephenson AJ, Smith A, Kattan MW, et al. Integration of gene expression profiling and clinical variable to predict prostate carcinoma recurrence after radical prostatectomy. Cancer 104:290-298 (2005).

Stephenson, RA, et al. An image analysis method for assessment of prognostic risk in prostate cancer: a pilot study. Anal Cell Pathol 3:243-8, 1991.

Stotzka, R. et al., "A hybrid neural and statistical classifier system for histopathologic grading of prostate lesions," *Anal. Quant. Cytol. Histol.*, vol. 17, pp. 204-218, 1995.

Su, A.I., Welsh, J.B., Sapinoso, L.M., Kern, S.G., Dimitrov, P., Lapp, H., Schultz, P.G., Powell, S.M., Moskaluk, C.A., Frierson, H.F., Jr. et al. 2001. Molecular classification of human carcinomas by use of gene expression signatures. *Cancer Res* 61:7388-7393.

Sun L, Gancarczyk K, Paquette E, et al. Introduction to Department of Defense Center for Prostate Disease Research Multicenter National Prostate Cancer Database, and analysis of changes in the PSA-era. Urol Oncol 2001;6:203-95.

Swindle P.W., et al., Markers and Meaning of Primary Treatment Failure. Urologic Clinics of North America. 30(2):377-401, May 2003.

Swindle, P., Eastham, J.A., Ohori, M., Kattan, M.W., Wheeler, T., Maru, N., Slawin, K., and Scardino, P.T. 2005. Do margins matter? The prognostic significance of positive surgical margins in radical prostatectomy specimens. J Urol 174:903-907(2005).

Teverovskiy, M. et al., "Improved prediction of prostate cancer recurrence base on an automated tissue image analysis system," in Proc. *IEEE Int. Symp. Biomed. Imaging*, Arlington, VA, 2004, pp. 257-260.

Tong, Zhao et al., "A novel scheme for abnormal cell detection in pap smear images". Proceedings of the Spie—The International Society for Optical Engineering SPIE-INT. Soc. Opt. Eng USA, vol. 5318, No. 1, Jul. 2004, pp. 151-162.

Veltri, RW, et al. Quantitative nuclear grade (QNG) : a new image analysis-based biomarker of clinically relevant nuclear structure alterations. J Cell Biochem Suppl Suppl 35:151-7, 2000.

Veltri, RW, et al. Quantitative nuclear morphometry, Markovian texture descriptors, and DNA content captured on a CAS-200 Image analysis system, combined with PCNA and HER-2/neuimmunohistochemistry for prediction of prostate cancer progression. J. Cell Biochem Suppl 19:249-58, 1994.

Veltri, RW, et al., Ability to predict biochemical progression using Gleason score and a computer-generated quantitative nuclear grade derived from cancer cell nuclei. Urology 48:685-91, 1996.

Vonesch, C., F. Aquet, J.L. Vonesch and M. Unser, "The colored revolution of bioimaging," IEEE Signal Proc. Mag., vol. 23, No. 3, pp. 20-31, May 2006.

Wang, N., et al. Morphometry of nucleli of the normal and malignant prostate in relation to DNA ploidy. Anal Quant Cytol Histol 14:210-6, 1992.

Ward JF, Blute ML, Slezak J, Bergstralh EJ, Zincke H. The long-term clinical impact of biochemical recurrence of prostate cancer 5 or more years after radical prostatectomy. J Urol 2003; 170:1872-65.

Welsh, J.B., Sapinoso, L.M., Su, A.I., Kern, S.G., Wang-Rodriguez, J., Moskaluk, C.A., Frierson, H.F., Jr., and Hampton, G.M. 2001. Analysis of gene expression identifies candidate markers and pharmacological targets in prostate cancer. Cancer Res 61:5974-5978 (2001).

Wetzel, A. W. et al. "Evaluation of prostate tumor grades by content-based image retrieval," in *Proc. SPIE AIPR Workshop on Advances in Computer-Assisted Recognition*, vol. 3584, Washington, DC, 1999, pp. 244-252.

Wirth M, Tyrrell C, Delaere K, et al. Bicalutamide ('Casodex') 150 mg in addition to standard care in patients with nonmetastic prostate cancer: updated results from a randomised double-blind phase III study (median follow-up 5.1 y) in the early prostate cancer programme. Prostate Cancer Prostatic Dis (2005);8:194-200.

Yan, I. et al., "*Optimizing classifier performance via an approximation function to the Wilcoxon-mann-whitney statistic,*"*Proc. Of 20$^{th}$ Int'l Conf. Machine Learning*, pp. 848-855, 2003.

Ye, Q.H., Qin, L.X., Forgues, M., He, P., Kim, J.W., Peng, A.C., Simon, R., Li, Y., Robles, A.I., Chen, Y., et al. 2003. Predicting hepatitis B virus-positive metastic hepatocellular carcinomas using gene expression profiling and supervised machine learning. Nat Med 9:416-423.

Yeang, C.H., Ramaswamy, S., Tamayo, P., Mukherjee, S., Rifkin, R.M., Angelo, M., Reich, M., Lander, E., Mesirov, J., and Golub, T. 2001. Molecular classification of multiple tumor types. Bioinformatics 17 Suppl 1:S316-322.

Yeh, W-C et al., << Liver fibrosis grade classification with B-mode ultrasound>> Ultrasound in Medicine and Biology, New York, NY, US, vol. 29, No. 9 Sep. 2003, pp. 1229-1235.

* cited by examiner

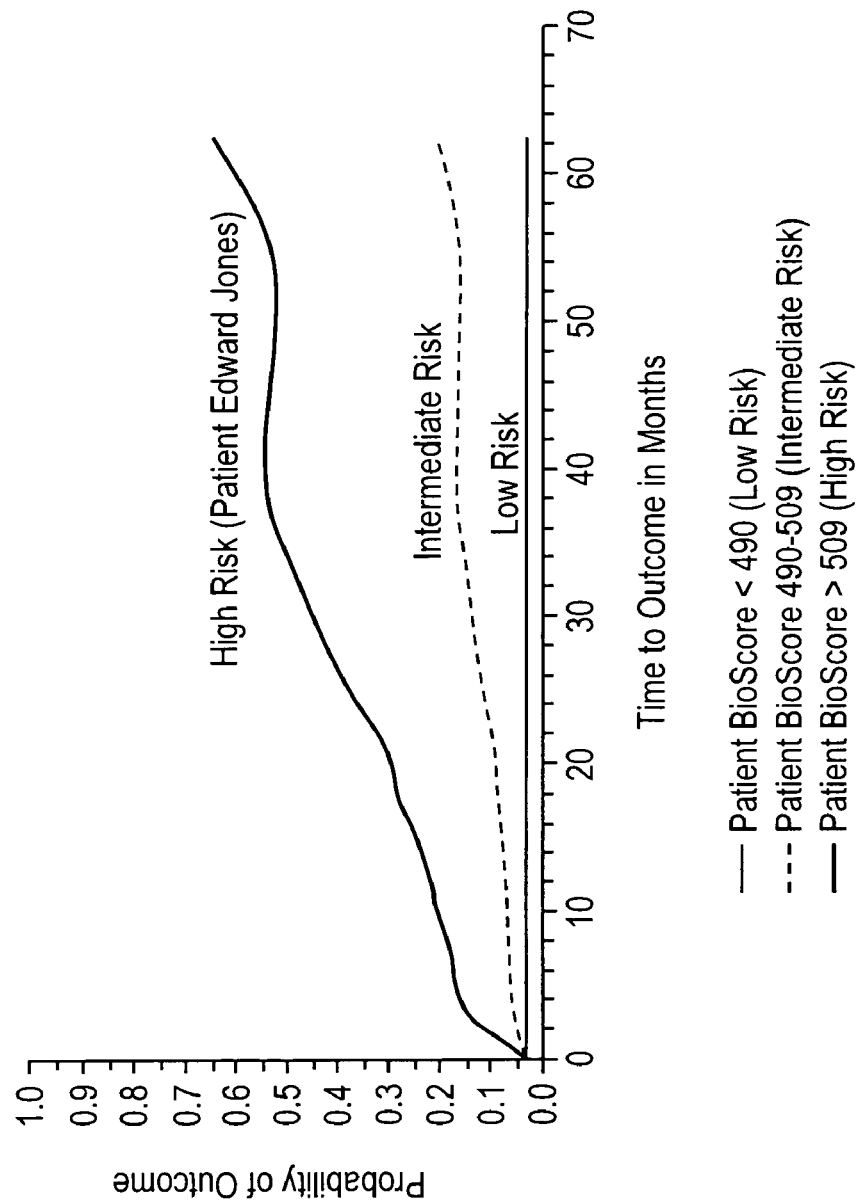

Image of healthy prostate tissue

Image of abnormal prostate tissue

FIG. 6

Features Selected for Prediction of PSA Recurrence (Example 2, Study 1)

| Feature | Description |
| --- | --- |
| Clinical | |
| | Biopsy Gleason Score |
| | Race |
| | UICC Stage |
| | Ploidy Result |
| | DRE Result |
| | Lymph Node Involvement |
| | Dominant Biopsy Gleason Grade |
| | Percent Ploidy in S Phase |
| | Post-operative Gleason Score |
| | TNM Stage |
| | Dominant Post-operative Gleason Grade |
| | Age |
| | Seminal Vesicle Involvement |
| | Pre-operative PSA |
| | Percent Ploidy Fraction |
| | Surgical Margin Involvement |
| | Extracapsular Involvement |
| Molecular | |
| | AR-tumor |
| | AR-gland |
| | CD34-tumor/PIN |
| | Ki67-tumor 2 |
| | CD45-Pin 3 |
| | CD34-tumor/stroma |
| | Ki-67-tumor 3 |
| | p27-tumor |
| | C14-PIN |
| | CD34-tumor |
| | PSA-gland |
| | PSMA-PIN |
| | CD34-PIN/stroma |
| | CD45-tumor 3 |
| Morphometric | |
| | Red Blood Cell Minimum Length in Pixels |
| | Epitheial Nuclei Maximum Compactness |
| | Lumen Minimum Radius of Smallest Enclosure |
| | Epithelial Nuclei Minimum Width in Pixels |
| | Stroma Maximum Density |
| | Lumen Maximum Border Length in Pixels |
| | Epithelial Nuclei Minimum Standard Deviation Channel 2 |
| | Epithelial Nuclei Maximum Radius of Smallest Enclosure |
| | Cytoplasm Standard Deviation of Border Length in Pixels |
| | Background Standard Deviation of Area in Pixels |

Features Selected for Prediction of PSA Recurrence (Example 2, Study 2)

| | | |
|---|---|---|
| Clinical | TNM Clinical Stage | 0.7431 |
| | Surgical Margins | 0.7937 |
| | Lymph Nodes | 0.8376 |
| Molecular | AR Staining Index (tumor) | 0.8528 |
| Morphometric | EpithelialNucleiMinCompactne0215 | 0.8222 |
| | StromaMaxStddevChannel30569 | 0.8483 |
| | CytoplasmStddevMaxDiff0148 | 0.8569 |
| | RedBloodCellMeanAreaPxl0386 | 0.8596 |
| | RedBloodCellStddevAreaPxl0388 | 0.8621 |
| | LumenMinAsymmetry0295 | 0.8635 |

FIG. 11

Features Selected for Prediction of Overall Survival (Example 2, Study 3)

| | | |
|---|---|---|
| Clinical | tnm | 0.7362 |
| | age | 0.7906 |
| Molecular | psapsi | 0.7595 |
| Morphometric | | |
| | StromaMinMeanChannel10535 | 0.6804 |
| | RedBloodCellMeanStddevChann30474 | 0.7475 |
| | StromaMinMeanChannel20539 | 0.7722 |
| | RedBloodCellMinMeanChannel20443 | 0.7772 |
| | RedBloodCellStddeStddeChann20472 | 0.7809 |
| | StromaMaxMaxDiff0529 | 0.7852 |
| | EpitheNucleMeanBordeLengtPxl0206 | 0.7888 |
| | EpithelialNucleMeanAreaPxl0194 | 0.7921 |
| | EpithelNucleiStddevElliptFit0228 | 0.7951 |
| | RedBloodCellStddeStddeChann30476 | 0.7964 |
| | RedBloodCellStddevElliptiFit0420 | 0.7976 |

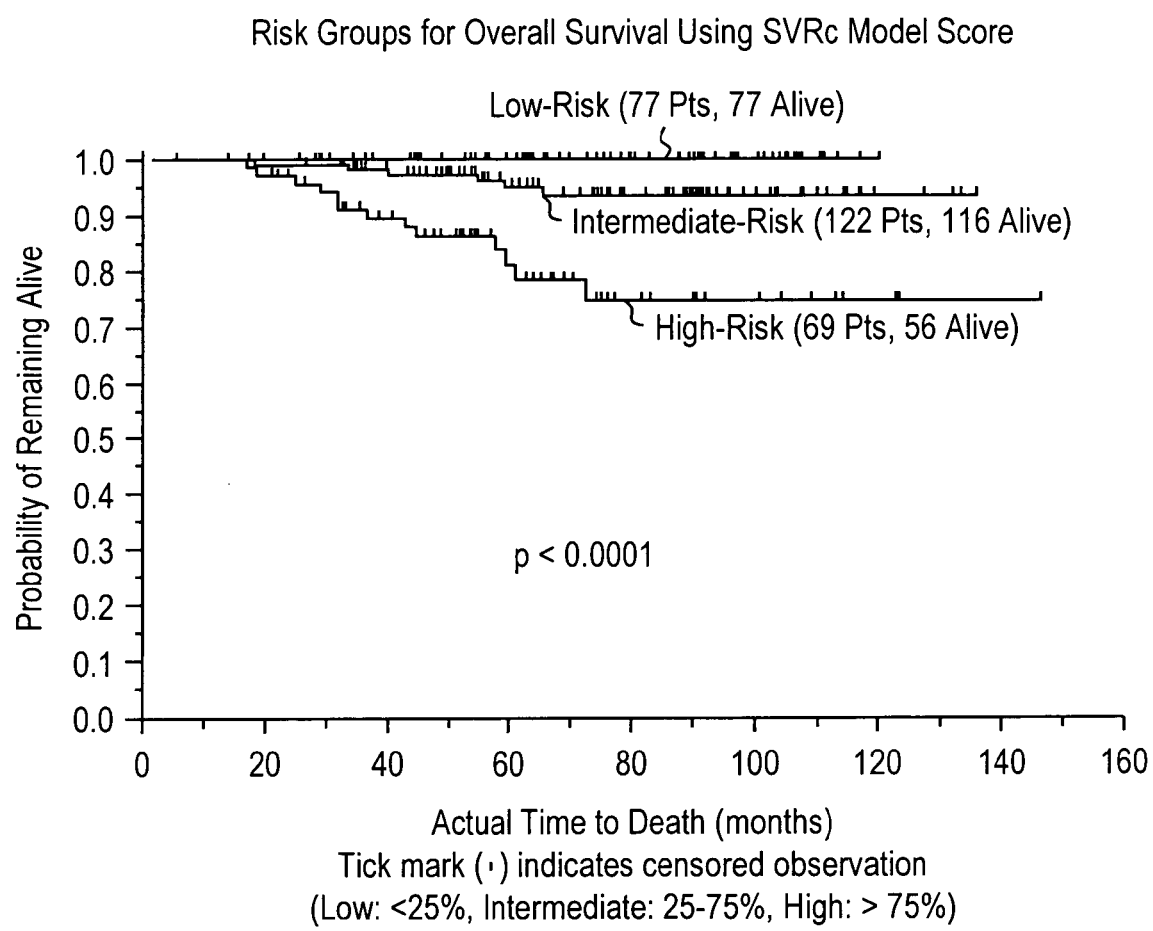

FIG. 13

| | Features Selected for Prediction of Clinical Failure (Example 3) |
|---|---|
| Clinical | Extracapsular Extension |
| | Seminal Vesicle Invasion |
| | Dominant Prostatectomy Gleason Grade |
| | Lymph Node Invasion |
| Morphometric | |
| | Cytoplasm Area Divided by Total Tissue Area |
| | Cytoplasm Standard Deviation of Mean Red Channel |
| | Lumen Area Divided by Total Tissue Area |

FIG. 14

Features Selected for Prediction of PSA Recurrence (Example 5)

| | | |
|---|---|---|
| Clinical | Lymph Nodes | -9.3742 |
| | Surgical Margin Involvement | -7.3159 |
| | Seminal Vesicle Involvement | -5.2103 |
| Molecular | AR (Tumor) Staining Index | -3.5404 |
| Morphometric | AreaStromadivTotTissueArea | -.34225 |
| | AreaEpitNucdivTotTissueArea | 3.2975 |

FIG. 15

Features Selected for Prediction of PSA Recurrence (Example 6)

| | | |
|---|---|---:|
| Clinical | Lymph Nodes | -23.32 |
| | Surgical Margin Involvement | -11.73 |
| | Biopsy Gleason Score | -10.60 |
| | Seminal Vesicle Involvement | -6.40 |
| Molecular | AR (Tumor) Staining Index | -10.49 |
| Morphometric | AreaStromadivTotTissueArea | -16.15 |
| | AreaEpitNucdivTotTissueArea | 11.54 |
| | StromaMeanStddevRedChann | -11.26 |

FIG. 16

Features Selected for Prediction of Clinical Failure
Post Prostatectomy (Example 7)

| | | |
|---|---|---|
| Clinical | Biopsy Gleason Score | -18.08 |
| | Lymph Node Involvement | -11.87 |
| | Specimen (Prostatectomy) Gleason Score | -6.36 |
| Molecular | AR intensity within AMACR epithelial cells | -6.20 |
| Morphometric | CytoplasmMeanMeanChannel | 19.68 |
| | StromaMeanStddevChannel | -10.06 |
| | EpitheNucleiStddevMeanChann | -8.87 |

SYSTEMS AND METHODS FOR TREATING, DIAGNOSING AND PREDICTING THE OCCURRENCE OF A MEDICAL CONDITION

RELATED APPLICATIONS

This is a continuation-in-part of U.S. patent application Ser. No. 11/080,360, filed Mar. 14, 2005, which is: a continuation-in-part of U.S. patent application Ser. No. 11/067,066, filed Feb. 25, 2005, which claims priority from U.S. Provisional Patent Application Nos. 60/548,322, filed Feb. 27, 2004, and 60/577,051, filed Jun. 4, 2004; a continuation-in-part of U.S. patent application Ser. No. 10/991,897, filed Nov. 17, 2004, which claims priority from U.S. Provisional Patent Application No. 60/520,815, filed Nov. 17, 2003; a continuation-in-part of U.S. patent application Ser. No. 10/624,233, filed Jul. 21, 2003; a continuation-in-part of U.S. patent application Ser. No. 10/991,240, filed Nov. 17, 2004, which claims priority from U.S. Provisional Patent Application No. 60/520,939 filed Nov. 18, 2003; and claims priority from U.S. Provisional Patent Application Nos. 60/552,497, filed Mar. 12, 2004, 60/577,051, filed Jun. 4, 2004, 60/600,764, filed Aug. 11, 2004, 60/620,514, filed Oct. 20, 2004, 60/645,158, filed Jan. 18, 2005, and 60/651,779, filed Feb. 9, 2005. This also claims priority from U.S. Provisional Patent Application No. 60/726,809, filed Oct. 13, 2005. All of the foregoing disclosures are hereby incorporated by reference herein in their entireties.

FIELD OF THE INVENTION

Embodiments of the invention relate to methods and systems that use clinical information, molecular information and computer-generated morphometric information in a predictive model for predicting the occurrence of a medical condition (e.g., disease or responsiveness or unresponsiveness to treatment). For example, in one embodiment, the invention comprises methods and systems that use clinical, molecular and morphometric information to treat, diagnose and predict the recurrence of prostate cancer.

BACKGROUND

Physicians are required to make many medical decisions ranging from, for example, whether and when a patient is likely to experience a medical condition to how a patient should be treated once the patient has been diagnosed with the condition. Determining an appropriate course of treatment for a patient may increase the patient's chances for, for example, survival and/or recovery. Similarly, predicting the occurrence of an event advantageously allows individuals to plan for the event. For example, predicting whether a patient is likely to experience occurrence (e.g., recurrence) of a disease may allow a physician to recommend an appropriate course of treatment for that patient.

Traditionally, physicians rely heavily on their expertise and training to treat, diagnose and predict the occurrence of medical conditions. For example, pathologists use the Gleason scoring system to evaluate the level of advancement and aggression of prostate cancer, in which cancer is graded based on the appearance of prostate tissue under a microscope as perceived by a physician. Higher Gleason scores are given to samples of prostate tissue that are more undifferentiated [1]. Although Gleason grading is widely considered by pathologists to be reliable, it is a subjective scoring system. Particularly, different pathologists viewing the same tissue samples may make conflicting interpretations.

Conventional tools for assisting physicians in medical diagnostics are limited in scope and application. For example, tools for assisting physicians with decisions regarding prostate cancer treatment after a patient has undergone radical prostatectomy are limited to serum-based PSA screening tests and generalized nomograms. One postoperative nomogram, developed by Kattan et al. U.S. Pat. No. 6,409,664, is widely used by urologists and allows prediction of the 7-year probability of disease recurrence for patients treated by radical prostatectomy. This nomogram provides information about the likelihood of biochemical failure only (i.e., an increase in PSA level), and does not predict clinical failure (death). Moreover, this nomogram only predicts whether a patient's condition is likely to recur within 7 years, and does not predict when in that interval the patient's condition might recur. Prognostic variables used in this nomogram include pre-treatment serum PSA levels, Gleason score, and microscopic assessment by a pathologist of prostate capsular invasion, surgical margins, seminal vesicle invasion, and lymph node status. Treatment failure is recorded when there is clinical evidence of disease recurrence, a rising serum PSA, or initiation of adjuvant therapy. However, these nomograms have several limitations. Of the most notable limitations is that even the best of these nomograms performs only slightly better than mid-way between a model with perfect discrimination (concordance index=1.0) and a model with no discriminating ability (concordance index=0.5). Furthermore, outcome for the approximately 30% of patients who have nomogram predictions in the mid range (7-year progression-free survival, 30-70%) is uncertain as the prediction is no more accurate than a coin toss.

Techniques in computer-implemented image processing and analysis have emerged that provide significantly increased computational power. In many applications, the ability to extract large amounts of quantitative continuous-valued features automatically from a single image has become a reality. A feature X is said to be continuous-valued if, for some A<B, the set of values for the feature includes all numbers x between A and B. Cancer image analysis systems have been developed for images taken from cytological specimens [2] [3]. However, such systems only capture cells and thus do not utilize all of the architectural information observable at the tissue level, let alone combine that information with clinical and molecular information. Cancer image analysis systems have not been provided for analyzing the structure of different pathological elements at the tissue level, which often plays a more important role in diagnosis (e.g., in Gleason analysis) than the appearance of individual cells. Thus, pathologists have resorted to manual techniques for analyzing the shape and size of the prostate gland to determine the pathologic grade of the cancer [4]. The deficiency of conventional cancer image analysis systems is exacerbated by the fact that tissue images are typically more complex than cellular images and require comprehensive domain expert knowledge to be understood.

In view of the foregoing, it would be desirable to provide systems and methods for treating, diagnosing and predicting the occurrence of medical conditions, responses and other medical phenomena with improved predictive power. It would also be desirable to provide computer-implemented systems and methods that utilize information at the tissue level to treat, diagnose and predict the occurrence of medical conditions.

SUMMARY OF THE INVENTION

Embodiments of the present invention provide automated systems and methods for predicting the occurrence of medical conditions. As used herein, predicting an occurrence of a medical condition may include, for example, predicting whether and/or when a patient will experience occurrence (e.g., recurrence) of disease such as cancer, predicting whether a patient is likely to respond to one or more therapies (e.g., a new pharmaceutical drug), and predicting the occurrence of any other suitable medical condition. Predictions by embodiments of the present invention may be used by physicians or other individuals to, for example, select an appropriate course of treatment for a patient and/or to diagnose a medical condition in the patient.

In an aspect of the present invention, systems and methods are provided for generating a model that predicts the occurrence of a medical condition. Generating a predictive model may include using an analytical tool to train a support vector machine (SVM) or a neural network with data for a cohort of patients whose outcomes are at least partially known. In one embodiment, the training data includes clinical data, molecular data, and computer-generated morphometric data. As used herein, "data" of a particular type (e.g., clinical, molecular, or morphometric) may include one or more features of that type. Additionally, morphometric data is defined to include any computer-generated data associated with or derived from an electronic (digital) image of tissue, including but not limited to data regarding structural properties of the tissue or portion thereof (e.g., area, length, width, compactness, and density), spectral properties of the tissue or portion thereof (e.g., red, green, blue (RGB) color channel values, brightness and channel histograms), and fractal properties of the tissue image and/or identified tissue components (e.g., fractal dimension of intraepithelial interface, lumen outline), statistical properties of wavelet decomposition coefficients and/or other image data transforms. In other embodiments, the training data includes computer-generated morphometric data only or the combination of clinical data and computer-generated morphometric data.

In one embodiment, systems and methods are provided for generating a predictive model based on one or more computer-generated morphometric features related to stroma, cytoplasm, epithelial nuclei, stroma nuclei, lumen, red blood cells, tissue artifacts, or tissue background, or a combination thereof. The predictive model may be generated based on the computer-generated morphometric features alone or in combination with one or more of the clinical features listed in Table 4 and/or one or more of the molecular features listed in Table 6. For example, the one or more features may be input to an analytical tool that determines an affect of the features on the ability of an associated model to predict a medical condition. Features that increase the predictive power of the model may be included in the final model, whereas features that do not increase (e.g., or decrease) the predictive power may be removed from consideration. Using the above-described morphometric features alone or in combination with the clinical and/or morphometric features listed in Tables 4 and/or 6, respectively, as a basis for developing a predictive model may focus the resources of physicians, other individuals, and/or automated processing equipment (e.g., a tissue image analysis system) on obtaining data for patient features that are more likely to be correlated with outcome and therefore useful in the final predictive model.

In another aspect of the present invention, a predictive model is provided that evaluates a dataset for a patient in order to evaluate the risk of occurrence of a medical condition in the patient, where the predictive model is based on computer-generated morphometric data alone or in combination with clinical data and/or molecular data. For example, the predictive model may receive the dataset for the patient as input, and may output a "score" indicating the likelihood that the patient will experience one or more outcomes related to the medical condition.

In one particular embodiment, a predictive model is provided that predicts the risk of prostate cancer recurrence in a patient, where the model is based on features including one or more of the following: seminal vesicle involvement, surgical margin involvement, lymph node status, androgen receptor (AR) staining index of tumor, a morphometric measurement of epithelial nuclei derived from a tissue image (e.g., area occupied by epithelial nuclei divided by total tissue area), and/or a morphometric measurement of stroma derived from a tissue image (e.g., area occupied by stroma divided by total tissue area). In some embodiments, the model may be based further on the features of biopsy Gleason score and/or a measurement of texture within the stroma derived from a tissue image. The model may evaluate a dataset for the patient, thereby evaluating a risk of prostate cancer recurrence in the patient.

In another embodiment, a predictive model is provided for predicting occurrence or recurrence of disease, where the model is based on one or more computer-generated morphometric features related to stroma, cytoplasm, epithelial nuclei, stroma nuclei, lumen, red blood cells, tissue artifacts, or tissue background, or a combination thereof. The predictive model may be based on these computer-generated morphometric features alone or in combination with one or more of the clinical features listed in Table 4 and/or one or more of the molecular features listed in Table 6.

In another embodiment, a predictive model is provided for predicting prostate cancer recurrence, where the model is based on one or more of the clinical and/or molecular features set forth in FIG. 6 and one or more morphometric features for one or more of the following pathological objects: red blood cell, epithelial nuclei, stroma, lumen, cytoplasm, and tissue background.

In yet another embodiment, a predictive model is provided for predicting prostate cancer recurrence, where the model is based on one or more of the clinical and/or molecular features set forth in FIG. 9 and one or more morphometric features for one or more of the following pathological objects: red blood cell, epithelial nuclei, stroma, lumen, and cytoplasm.

In another embodiment, a predictive model is provided for predicting prostate cancer survivability, where the model is based on one or more of the clinical and/or molecular features set forth in FIG. 11 and one or more morphometric features for one or more of the following pathological objects: red blood cell, epithelial nuclei, and stroma.

In other embodiments, the predictive model may determine whether a tissue sample is normal or abnormal or may predict whether a patient is likely to experience clinical failure post prostatectomy. In one particular embodiment, a predictive model is provided that predicts the risk of clinical failure post prostatectomy, where the model is based on features including one or more (e.g., one, two, three, four, etc.) of the following: biopsy Gleason score, lymph node involvement, prostatectomy Gleason score, a morphometric measurement of epithelial cytoplasm derived from a tissue image (e.g., mean intensity of epithelial cytoplasm), a morphometric measurement of epithelial nuclei derived from a tissue image (e.g., variation in texture in the epithelial nuclei), a morphometric measurement of stroma derived from a tissue image (e.g., variation in texture within the stroma), and/or intensity of androgen receptor (AR) in racemase (AMACR)-positive epithelial cells (e.g., generated based on computer analysis of a tissue image showing immunofluorescence). The model may evaluate a dataset for the patient, thereby evaluating a risk of clinical failure in the patient.

In another aspect, systems and methods are provided in which data for a patient is measured at each of a plurality of points in time and evaluated by a predictive model of the present invention. A diagnosis or treatment of the patient may be based on a comparison of the results from each evaluation. Such a comparison may be summarized in, for example, a report output by a computer for use by a physician or other individual. For example, systems and methods may be provided for screening for an inhibitor compound of a medical condition. A first dataset for a patient may be evaluated by a predictive model, where the model is based on clinical data, molecular data, and computer-generated morphometric data. A test compound may be administered to the patient. Following administering of the test compound, a second dataset may be obtained from the patient and evaluated by the predictive model. The results of the evaluation of the first dataset may be compared to the results of the evaluation from the second dataset. A change in the results for the second dataset with respect to the first dataset may indicate that the test compound is an inhibitor compound.

In still another aspect of the present invention, a test kit is provided for treating, diagnosing and/or predicting the occurrence of a medical condition. Such a test kit may be situated in a hospital, other medical facility, or any other suitable location. The test kit may receive data for a patient (e.g., including clinical data, molecular data, and/or computer-generated morphometric data), compare the patient's data to a predictive model (e.g., programmed in memory of the test kit) and output the results of the comparison. In some embodiments, the molecular data and/or the computer-generated morphometric data may be at least partially generated by the test kit. For example, the molecular data may be generated by an analytical approach subsequent to receipt of a tissue sample for a patient. The morphometric data may be generated by segmenting an electronic image of the tissue sample into one or more objects, classifying the one or more objects into one or more object classes (e.g., stroma, lumen, red blood cells, etc.), and determining the morphometric data by taking one or more measurements for the one or more object classes. In some embodiments, the test kit may include an input for receiving, for example, updates to the predictive model. In some embodiments, the test kit may include an output for, for example, transmitting data, such as data useful for patient billing and/or tracking of usage, to another device or location.

BRIEF DESCRIPTION OF THE DRAWINGS

For a better understanding of embodiments of the present invention, reference is made to the following description, taken in conjunction with the accompanying drawings, in which like reference characters refer to like parts throughout, and in which:

FIG. 2 shows illustrative results for a patient that may be output by a predictive model;

FIG. 6 shows various clinical, molecular, and computer-generated morphometric features used by a model to predict prostate cancer recurrence;

FIG. 9 shows various clinical, molecular, and computer-generated morphometric features used by a model to predict prostate cancer recurrence;

FIG. 11 shows various clinical, molecular, and computer-generated morphometric features used by a model to predict overall survivability of prostate cancer;

FIG. 12 is a graph of a Kaplan-Meier curve demonstrating a classification of patients as being at low-risk, intermediate-risk, or high-risk of death due to any cause as predicted by a model based on the features of FIG. 11;

FIG. 13 shows various clinical and computer-generated morphometric features used by a model to predict aggressive disease subsequent to a patient having a prostatectomy;

FIGS. 14 and 15 show various clinical, molecular, and computer-generated morphometric features used by a model to predict prostate cancer recurrence; and FIG. 16 shows various clinical and computer-generated tissue image features used by a model to predict clinical failure in a patient subsequent to radical prostatectomy.

DETAILED DESCRIPTION OF THE PREFERRED EMBODIMENTS

Figure 1A:
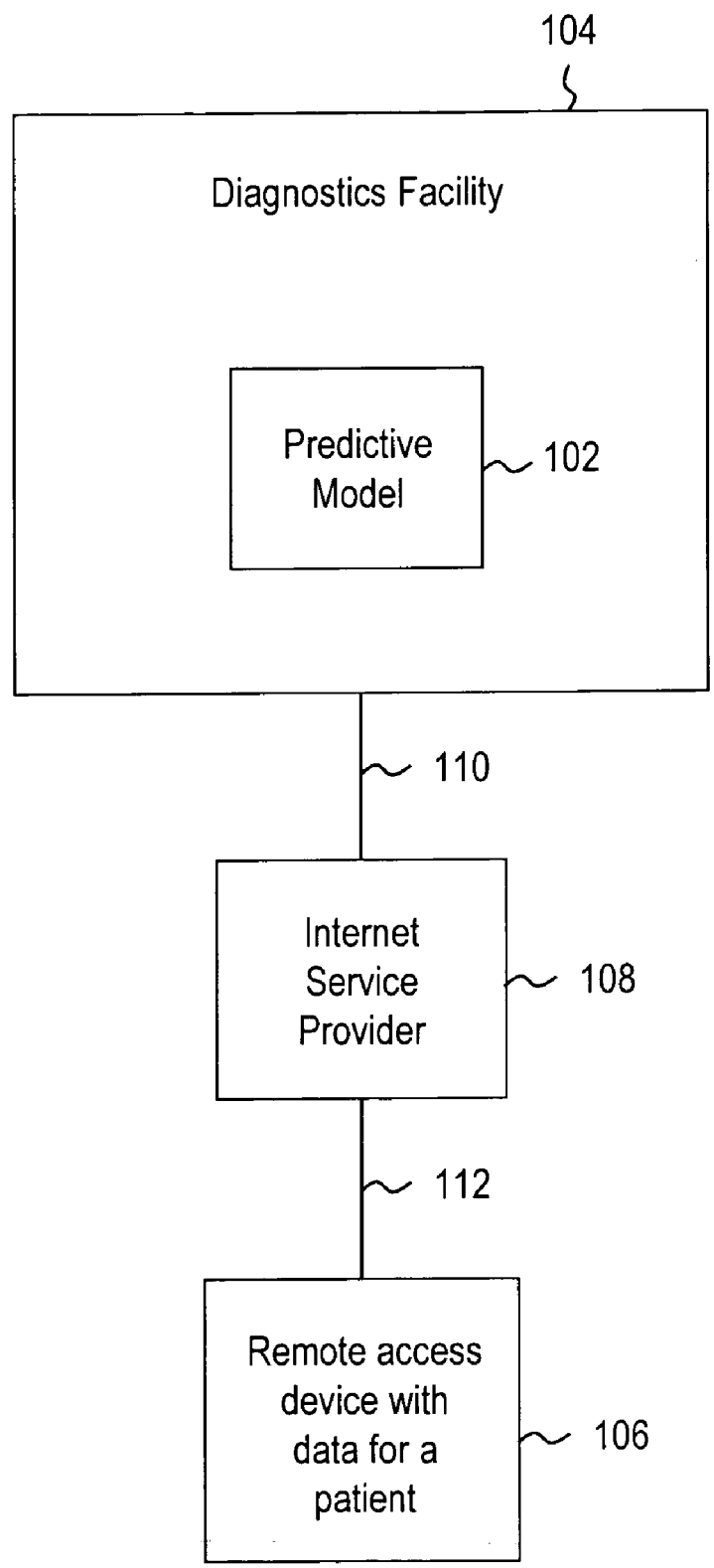
FIGS. 1A and 1B are block diagrams of systems that use a predictive model to treat, diagnose or predict the occurrence of a medical condition.

Embodiments of this invention relate to methods and systems that use computer-generated morphometric information alone or in combination with clinical information and/or molecular information in a predictive model for predicting the occurrence of a medical condition. For example, in one embodiment of the present invention, clinical, molecular and computer-generated morphometric information is used to predict the recurrence of prostate cancer. In other embodiments, the teachings provided herein are used to predict the occurrence of other medical conditions such as, for example, other types of disease (e.g., epithelial and mixed-neoplasms including breast, colon, lung, bladder, liver, pancreas, renal cell, and soft tissue) and the responsiveness or unresponsiveness of a patient to one or more therapies (e.g., pharmaceutical drugs). These predictions may be used by physicians or other individuals to, for example, select an appropriate course of treatment for a patient and/or to diagnose a medical condition in the patient.

In an aspect of the present invention, an analytical tool including a support vector machine (SVM) and/or a neural network may be provided that determines correlations between clinical, molecular, and computer-generated morphometric features and a medical condition. The correlated features may form a model that can be used to predict the occurrence or recurrence of the condition. For example, an analytical tool may be used to generate a predictive model based on data for a cohort of patients whose outcomes with respect to a medical condition (e.g., time to recurrence of cancer) are at least partially known. The model may then be used to evaluate data for a new patient in order to predict the occurrence of the medical condition for the new patient. In some embodiments, only a subset of the three data types (e.g., clinical and morphometric data only) may be used by the analytical tool to generate the predictive model.

The clinical, molecular, and/or morphometric data used by embodiments of the present invention may include any clinical, molecular, and/or morphometric data that is relevant to the diagnosis, treatment and/or prediction of a medical condition. Features analyzed for correlations with prostate cancer recurrence and survival in order to generate predictive models are described below in connection with, for example, Tables 1, 2, 4 and/or 6. It will be understood that at least some of these features (e.g., epithelial and mixed-neoplasms) may provide a basis for developing predictive models for other medical conditions (e.g., breast, colon, lung, bladder, liver, pancreas, renal cell, and soft tissue). For example, one or more of the features in Tables 1, 2, 4 and/or 6 may be assessed for patients having some other medical condition and then input to an analytical tool that determines whether the features correlate with the medical condition. Features that increase the ability of the model to predict the occurrence of the medical condition may be included in the final model, whereas features that do not increase (e.g., or decrease) the predictive power of the model may be removed from consideration. Using the features in Tables 1, 2, 4 and/or 6 as a basis for developing a predictive model may focus the resources of physicians, other individuals, and/or automated processing equipment (e.g., a tissue image analysis system) on obtaining patient data that is more likely to be correlated with outcome and therefore useful in the final predictive model. Moreover, the features determined to be correlated with prostate cancer recurrence and survival are shown in FIGS. 6, 9, and 11. It will be understood that these features may be included directly in final models predictive of prostate cancer recurrence and/or survival, and/or used for developing predictive models for other medical conditions.

The morphometric data may include computer-generated data indicating various structural and/or spectral properties of, for example, tissue specimens. In one embodiment, the morphometric data may include data for morphometric features of stroma, cytoplasm, epithelial nuclei, stroma nuclei, lumen, red blood cells, tissue artifacts, tissue background, or a combination thereof. In an aspect of the present invention, a tissue image analysis system is provided for obtaining measurements of the morphometric features from a tissue image. Such a system may be the MAGIC™ system which uses the Definiens Cellenger software. Such a system may receive an H&E stained image as input, and may output various measurements of morphometric features for pathological objects in the image. Additional details regarding systems and methods for obtaining morphometric features from an image are described below in connection with FIG. 3.

Clinical features may include or be based on data for one or more patients such as age, race, weight, height, medical history, genotype and disease state, where disease state refers to clinical and pathologic staging characteristics and any other clinical features gathered specifically for the disease process at hand. Generally, clinical data is gathered by a physician during the course of examining a patient and/or the tissue or cells of the patient. The clinical data may also include clinical data that may be more specific to a particular medical context. For example, in the context of prostate cancer, the clinical data may include data indicating blood concentration of prostate specific antigen (PSA), the result of a digital rectal exam, Gleason score, and/or other clinical data that may be more specific to prostate cancer. Generally, when any features (i.e., clinical, morphometric and/or molecular) in Tables 1, 2, 4 and/or 6 and/or FIGS. 6, 9 and/or 11 are applied to medical contexts other than the prostate, features from these Tables and/or Figures that are more specific to the prostate may not be considered. Optionally, features more specific to the medical context in question may be substituted for the prostate-specific features. For example, other histologic disease-specific features/manifestations may include regions of necrosis (e.g., ductal carcinoma in situ for the breast), size, shape and regional pattern/distribution of epithelial cells (e.g., breast, lung), degree of differentiation (e.g., squamous differentiation with non-small cell lung cancer (NSCLC, mucin production as seen with various adenocarcinomas seen in both breast and colon)), morphological/microscopic distribution of the cells (e.g., lining ducts in breast cancer, lining bronchioles in NSCLC), and degree and type of inflammation (e.g., having different characteristics for breast and NSCLC in comparison to prostate).

The molecular features may include or be based on data indicating the presence, absence, relative increase or decrease or relative location of biological molecules including nucleic acids, polypeptides, saccharides, steroids and other small molecules or combinations of the above, for example, glycoroteins and protein-RNA complexes. The locations at which these molecules are measured may include glands, tumors, stroma, and/or other locations, and may depend on the particular medical context. Generally, molecular data is gathered using common molecular biological and biochemical techniques including Southern, Western, and Northern blots, polymerase chain reaction (PCR), immunohistochemistry, and immunofluorescence. Further, in situ hybridization may be used to show both the relative abundance and location of molecular biological features. Illustrative methods and systems for in situ hybridization of tissue are described in above-incorporated U.S. patent application Ser. No. 10/624, 233, filed Jul. 21, 2003, and entitled "Methods and compositions for the preparation and use of fixed-treated cell-lines and tissue in fluorescence in situ hybridization."

Figure 1B:
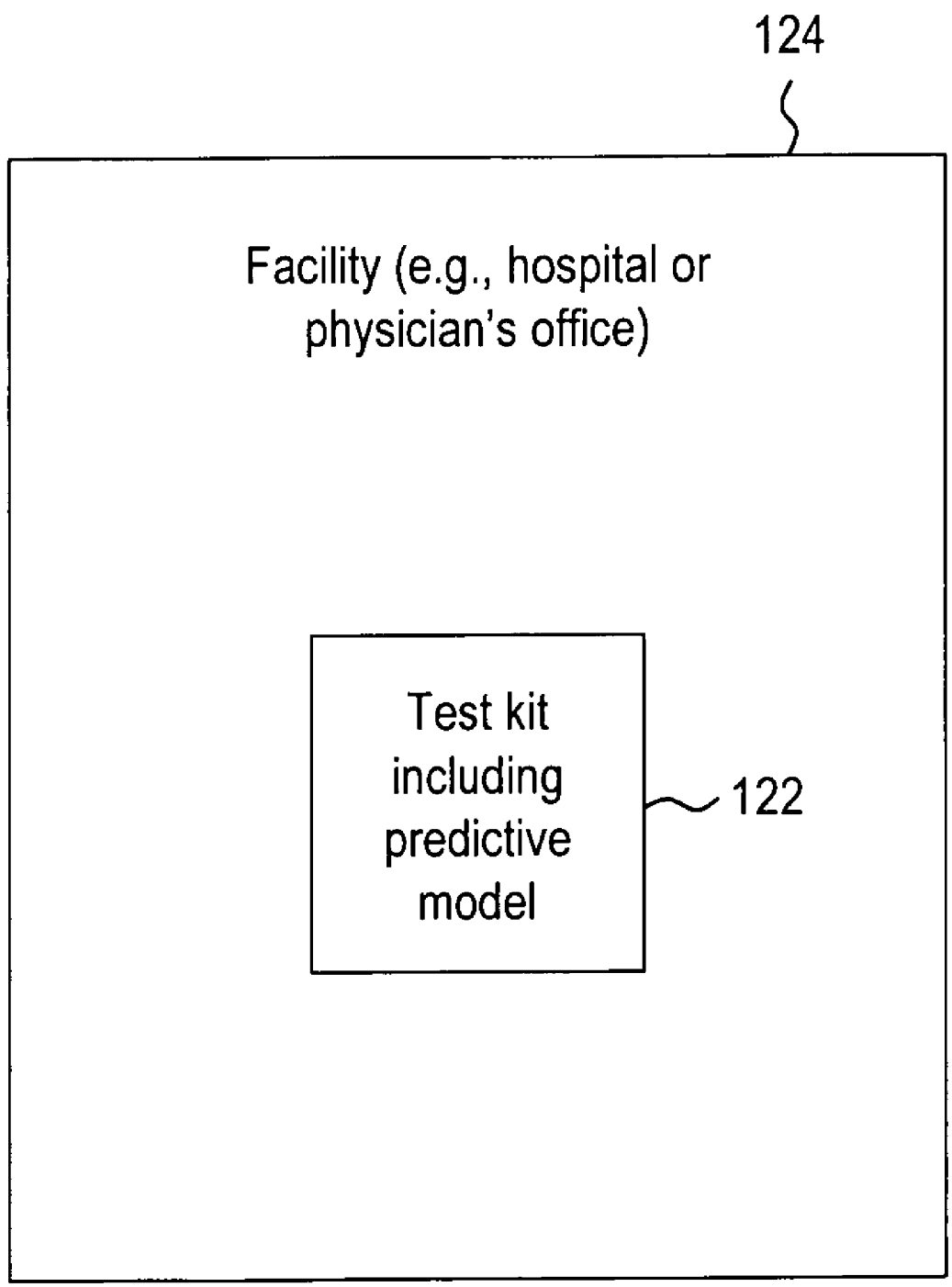

FIGS. 1A and 1B show illustrative systems that use a predictive model to predict the occurrence of a medical condition in a patient. The arrangement in FIG. 1A may be used when, for example, a medical diagnostics lab provides support for a medical decision to a physician or other individual associated with a remote access device. The arrangement in FIG. 1B may be used when, for example, a test kit including the predictive model is provided for use in a facility such as a hospital, other medical facility, or other suitable location.

Referring to FIG. 1A, predictive model 102 is located in diagnostics facility 104. Predictive model 102 may include any suitable hardware, software, or combination thereof for receiving data for a patient, evaluating the data in order to predict the occurrence (e.g., recurrence) of a medical condition for the patient, and outputting the results of the evaluation. In another embodiment, model 102 may be used to predict the responsiveness of a patient to particular one or more therapies. Diagnostics facility 104 may receive data for a patient from remote access device 106 via Internet service provider (ISP) 108 and communications networks 110 and 112, and may input the data to predictive model 102 for evaluation. Other arrangements for receiving and evaluating data for a patient from a remote location are of course possible (e.g., via another connection such as a telephone line or through the physical mail). The remotely located physician or individual may acquire the data for the patient in any suitable manner and may use remote access device 106 to transmit the data to diagnostics facility 104. In some embodiments, the data for the patient may be at least partially generated by diagnostics facility 104 or another facility. For example, diagnostics facility 104 may receive a digitized version of an H&E stained image from remote access device 106 or other device and may generate morphometric data for the patient based on the image. In another example, actual tissue samples may be received and processed by diagnostics facility 104 in order to generate the morphometric data. In other examples, a third party may receive an image or tissue for a new patient, generate morphometric data based on the image or tissue, and provide the morphometric data to diagnostics facility 104. A suitable image processing tool for generating morphometric data from tissue images and/or samples is described below in connection with FIG. 3.

Diagnostics facility 104 may provide the results of the evaluation to a physician or individual associated with remote access device 106 through, for example, a transmission to remote access device 106 via ISP 108 and communications networks 110 and 112 or in another manner such as the physical mail or a telephone call. The results may include a diagnostic "score" (e.g., an indication of the likelihood that the patient will experience one or more outcomes related to the medical condition such as the predicted time to recurrence of the event), information indicating one or more features analyzed by predictive model 102 as being correlated with the medical condition, information indicating the sensitivity and/or specificity of the predictive model, or other suitable diagnostic information or a combination thereof. For example, FIG. 2 shows an example of a report for a fictional patient that may be output by the predictive model. As shown, the report maps the patient's probability of outcome (e.g., recurrence of prostate cancer; i.e., y-axis) to time in months (x-axis). In this example, the patient has a score of "520" which places the patient in a high-risk category. Such a report may be used by a physician or other individual to assist in determining a more refined clinical-diagnostic tumor grade, develop an effective means to sub-classify patients and finally generate more accurate (and appropriate) treatment option algorithms for the individual patient. The report may also be useful in that it may help the physician or individual to explain the patient's risk to the patient.

Remote access device 106 may be any remote device capable of transmitting and/or receiving data from diagnostics facility 104 such as, for example, a personal computer, a wireless device such as a laptop computer, a cell phone or a personal digital assistant (PDA), or any other suitable remote access device. Multiple remote access devices 106 may be included in the system of FIG. 1A (e.g., to allow a plurality of physicians or other individuals at a corresponding plurality of remote locations to communicate data with diagnostics facility 104), although only one remote access device 106 has been included in FIG. 1A to avoid over-complicating the drawing. Diagnostics facility 104 may include a server capable of receiving and processing communications to and/or from remote access device 106. Such a server may include a distinct component of computing hardware and/or storage, but may also be a software application or a combination of hardware and software. The server may be implemented using one or more computers.

Each of communications links 110 and 112 may be any suitable wired or wireless communications path or combination of paths such as, for example, a local area network, wide area network, telephone network, cable television network, intranet, or Internet. Some suitable wireless communications networks may be a global system for mobile communications (GSM) network, a time-division multiple access (TDMA) network, a code-division multiple access (CDMA) network, a Bluetooth network, or any other suitable wireless network.

FIG. 1B shows a system in which test kit 122 including the predictive model of the present invention is provided for use in facility 124, which may be a hospital, a physician's office, or other suitable location. Test kit 122 may include any suitable hardware, software, or combination thereof (e.g., a personal computer) that is adapted to receive data for a patient (e.g., at least one of clinical, morphometric and molecular data), evaluate the patient's data with a predictive model (e.g., programmed in memory of the test kit), and output the results of the evaluation. For example, test kit 122 may include a computer readable medium encoded with computer executable instructions for performing the functions of the predictive model. The predictive model may be a predetermined model previously generated (e.g., by another system or application such as the system in FIG. 1C). In some embodiments, test kit 122 may optionally include an image processing tool capable of generating data corresponding to morphometric features from, for example, a tissue sample or image. A suitable image processing tool is described below in connection with FIG. 3. In other embodiments, test kit 122 may receive pre-packaged data for the morphometric features as input from, for example, an input device (e.g., keyboard) or another device or location. Test kit 122 may optionally include an input for receiving, for example, updates to the predictive model. The test kit may also optionally include an output for transmitting data, such as data useful for patient billing and/or tracking of usage, to a main facility or other suitable device or location. The billing data may include, for example, medical insurance information for a patient evaluated by the test kit (e.g., name, insurance provider, and account number). Such information may be useful when, for example, a provider of the test kit charges for the kit on a per-use basis and/or when the provider needs patients' insurance information to submit claims to insurance providers.

Figure 1C:
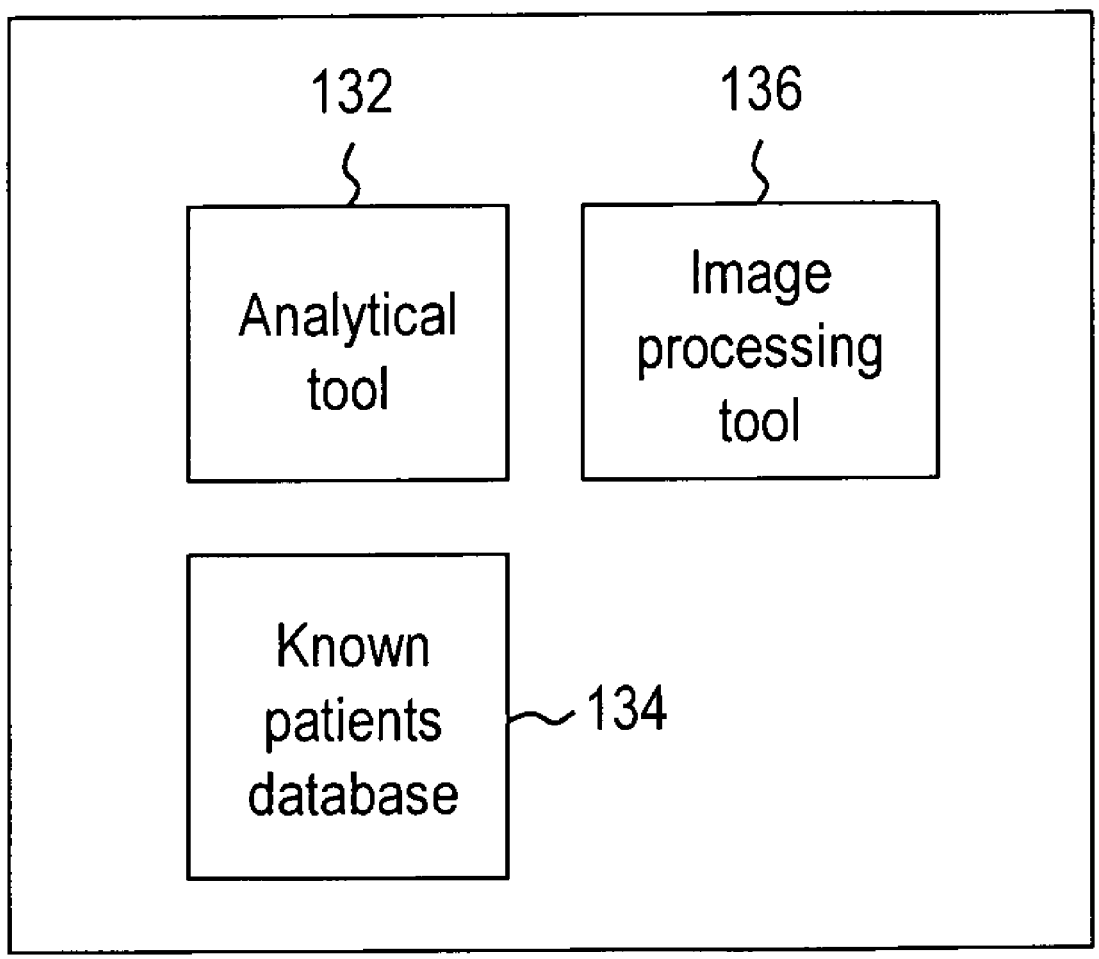
FIG. 1C is a block diagram of a system for generating a predictive model.

FIG. 1C shows an illustrative system for generating a predictive model. The system includes analytical tool 132 (e.g., including a support vector machine (SVM) and/or a neural network) and database 134 of patients whose outcomes are at least partially known. Analytical tool 132 may include any suitable hardware, software, or combination thereof for determining correlations between the data from database 134 and a medical condition. The system in FIG. 1C may also include image processing tool 136 capable of generating morphometric data based on, for example, a digitized version of an H&E stained tissue image, an actual tissue sample, or both. Tool 136 may generate morphometric data for, for example, the known patients whose data is included in database 134. A suitable image processing tool 136 is described below in connection with FIG. 3.

Database 134 may include any suitable patient data such as data for clinical features, morphometric features, molecular features, or a combination thereof. Database 134 may also include data indicating the outcomes of patients such as whether and when the patients have experienced disease recurrence. For example, database 134 may include uncensored data for patients (i.e., data for patients whose outcomes are completely known) such as data for patients who have experienced a recurrence of a medical condition. Database 134 may alternatively or additionally include censored data for patients (i.e., data for patients whose outcomes are not completely known) such as data for patients who have not shown signs of disease recurrence in one or more follow-up visits to a physician. The use of censored data by analytical tool 132 may increase the amount of data available to generate the predictive model and, therefore, may advantageously improve the reliability and predictive power of the model. Examples of support vector machines (SVM) and neural networks (NNci) that can make use of both censored and uncensored data are described below.

In one embodiment, analytical tool 132 may include a support vector machine (SVM). In such an embodiment, tool 132 preferably includes an SVM capable of performing support vector regression on censored data (SVRc). As described in co-pending U.S. patent application Ser. No. 10/991,240, in SVRc a novel modified loss/penalty function is provided for use within an SVM that may allow the SVM to utilize censored data. Data including clinical, molecular and/or morphometric features of known patients from database 134 may be input to the SVM to determine parameters for a predictive model. The parameters may indicate the relative importance of input features, and may be adjusted in order to maximize the ability of the SVM to predict the outcomes of the known patients. Additional details regarding the use of SVM to determine correlations of features with a medical condition are described in [5] and [6].

The use of SVRc by analytical tool 132 may include obtaining from database 134 multi-dimensional, non-linear vectors of information indicative of status of patients, where at least one of the vectors lacks an indication of a time of occurrence of an event with respect to a corresponding patient. Analytical tool 132 may then perform regression using the vectors to produce a kernel-based model that provides an output value related to a prediction of time to the event based upon at least some of the information contained in the vectors of information. Analytical tool 132 may use a loss function for each vector containing censored data that is different from a loss function used by tool 132 for vectors comprising uncensored data. A censored data sample may be handled differently because it may provide only "one-sided information." For example, in the case of survival time prediction, a censored data sample typically only indicates that the event has not happened within a given time, and there is no indication of when it will happen after the given time, if at all.

The loss function used by analytical tool 132 for censored data may be as follows:

$$\text{Loss}(f(x), y, s = 1) = \begin{cases} C_s^*(e - \varepsilon_s^*) & e > \varepsilon_s^* \\ 0 & -\varepsilon_s \leq e \leq \varepsilon_s^* \\ C_s(\varepsilon_s - e) & e < -\varepsilon_s \end{cases}$$

where $e = f(x) - y$; and $$f(x) = W^T \Phi(x) + b$$

is a linear regression function on a feature space F. Here, W is a vector in F, and $\Phi(x)$ maps the input x to a vector in F.

In contrast, the loss function used by tool 132 for uncensored data may be:

$$\text{Loss}(f(x), y, s = 0) = \begin{cases} C_n^*(e - \varepsilon_n^*) & e > \varepsilon_n^* \\ 0 & -\varepsilon_n \leq e \leq \varepsilon_n^* \\ C_n(\varepsilon_n - e) & e < -\varepsilon_n \end{cases}$$

where $e = f(x) - y$ and $\varepsilon_n^* \leq \varepsilon_n$ and $C_n^* \geq C_n$.

In the above description, the W and b are obtained by solving an optimization problem, the general form of which is:

$$\min_{W, b} \frac{1}{2} W^T W$$

$$\text{s.t.} \quad y_i - (W^T \phi(x_i) + b) \leq \varepsilon$$

$$(W^T \phi(x_i) + b) - y_i \leq \varepsilon$$

This equation, however, assumes the convex optimization problem is always feasible, which may not be the case. Furthermore, it is desired to allow for small errors in the regression estimation. It is for these reasons that a loss function is used for SVRc. The loss allows some leeway for the regression estimation. Ideally, the model built will exactly compute all results accurately, which is infeasible. The loss function allows for a range of error from the ideal, with this range being controlled by slack variables ξ and ξ*, and a penalty C. Errors that deviate from the ideal, but are within the range defined by ξ and ξ*, are counted, but their contribution is mitigated by C. The more erroneous the instance, the greater the penalty. The less erroneous (closer to the ideal) the instance is, the less the penalty. This concept of increasing penalty with error results in a slope, and C controls this slope. While various loss functions may be used, for an epsilon-insensitive loss function, the general equation transforms into:

$$\min_{W,b} \quad P = \frac{1}{2} W^T W + C \sum_{i=1}^{l} (\xi_i + \xi_i^*)$$

$$\text{s.t.} \quad y_i - (W^T \Phi(x_i) + b) \leq \varepsilon + \xi_i$$

$$(W^T \Phi(x_i) + b) - y_i \leq \varepsilon + \xi_i^*$$

$$\xi_i, \xi_i^* \geq 0, \quad i = 1 \ldots l$$

For an epsilon-insensitive loss function in accordance with the invention (with different loss functions applied to censored and uncensored data), this equation becomes:

$$\min_{W,b} \quad P_c = \frac{1}{2} W^T W + \sum_{i=1}^{l} (C_i \xi_i + C_i^* \xi_i^*)$$

$$\text{s.t.} \quad y_i - (W^T \Phi(x_i) + b) \leq \varepsilon_i + \xi_i$$

$$(W^T \Phi(x_i) + b) - y_i \leq \varepsilon_i^* + \xi_i^*$$

$$\xi_i^{(*)} \geq 0, \quad i = 1 \ldots l$$

where $C_i^{(*)} = s_i C_s^{(*)} + (1 - s_i) C_n^{(*)}$ $$\varepsilon_i^{(*)} = s_i \varepsilon_s^{(*)} + (1 - s_i) \varepsilon_n^{(*)}$$

The optimization criterion penalizes data points whose y-values differ from f(x) by more than ε. The slack variables, ξ and ξ*, correspond to the size of this excess deviation for positive and negative deviations respectively. This penalty mechanism has two components, one for uncensored data (i.e., not right-censored) and one for censored data. Both components are, here, represented in the form of loss functions that are referred to as ε-insensitive loss functions.

Additional details regarding systems and methods for performing support vector regression on censored data (SVRc) are described in above-incorporated U.S. patent application Ser. No. 10/991,240, filed Nov. 17, 2004, and U.S. Provisional Patent Application No. 60/520,939, filed Nov. 18, 2003.

In another embodiment, analytical tool 132 may include a neural network. In such an embodiment, tool 132 preferably includes a neural network that is capable of utilizing censored data. Additionally, the neural network preferably uses an objective function substantially in accordance with an approximation (e.g., derivative) of the concordance index (CI) to train an associated model (NNci). Though the CI has long been used as a performance indicator for survival analysis [7], the use of the CI to train a neural network has not been proposed previously. The difficulty of using the CI as a training objective function in the past is that the CI is non-differentiable and cannot be optimized by gradient-based methods. As described in co-pending U.S. patent application Ser. No. 11/067,066, filed Feb. 25, 2005, this obstacle may be overcome by using an approximation of the CI as the objective function.

For example, when analytical tool 132 includes a neural network that is used to predict prostate cancer recurrence, the neural network may process input data for a cohort of patients whose outcomes with respect to prostate cancer recurrence are at least partially known in order to produce an output. The particular features selected for input to the neural network may be selected through the use of the above-described SVRc (e.g., implemented with a support vector machine of analytical tool 132) or using another suitable feature selection process. An error module of tool 132 may determine an error between the output and a desired output corresponding to the input data (e.g., the difference between a predicted outcome and the known outcome for a patient). Analytical tool 132 may then use an objective function substantially in accordance with an approximation of the CI to rate the performance of the neural network. Analytical tool 132 may adapt the weighted connections (e.g., relative importance of features) of the neural network based upon the results of the objective function. Additional details regarding adapting the weighed connections of a neural network in order to adjust the correlations of features with a predicted outcome are described in [8] and [9].

The concordance index may be expressed in the form:

$$CI = \frac{\sum_{(i,j) \in \Omega} I(\hat{t}_i, \hat{t}_j)}{|\Omega|}$$

where $$I(\hat{t}_i, \hat{t}_j) = \begin{cases} 1: \hat{t}_i > \hat{t}_j \\ 0: \text{otherwise} \end{cases},$$

and may be based on pair-wise comparisons between the prognostic estimates $\hat{t}_i$ and $\hat{t}_j$ for patients i and j, respectively. In this example, $\Omega$ consists of all the pairs of patients $\{i,j\}$ who meet the following conditions:

both patients i and j experienced recurrence, and the recurrence time $t_i$ of patient i is shorter than patient j's recurrence time $t_j$; or only patient i experienced recurrence and $t_i$ is shorter than patient j's follow-up visit time $t_j$.

The numerator of the CI represents the number of times that the patient predicted to recur earlier by the neural network actually does recur earlier. The denominator is the total number of pairs of patients who meet the predetermined conditions.

Generally, when the CI is increased, preferably maximized, the model is more accurate. Thus, by preferably substantially maximizing the CI, or an approximation of the CI, the performance of a model is improved. An embodiment of the present invention provides an approximation of the CI as follows:

$$C = \frac{\sum_{(i,j) \in \Omega} R(\hat{t}_i, \hat{t}_j)}{|\Omega|}$$

where $$R(\hat{t}_i, \hat{t}_j) = \begin{cases} (-(\hat{t}_i - \hat{t}_j - \gamma))^n : \hat{t}_i - \hat{t}_j < \gamma \\ 0: \text{otherwise} \end{cases},$$

and where $0 < \gamma \leq 1$ and $n > 1$. $R(\hat{t}_i, \hat{t}_j)$ can be regarded as an approximation to $I(-\hat{t}_i, -\hat{t}_j)$.

Another approximation of the CI provided by the present invention which has been shown empirically to achieve improved results is the following:

$$C_\omega = \frac{\sum_{(i,j) \in \Omega} -(\hat{t}_i - \hat{t}_j) \cdot R(\hat{t}_i, \hat{t}_j)}{D},$$

where $$D = \sum_{(i,j) \in \Omega} -(\hat{t}_i - \hat{t}_j)$$

is a normalization factor. Here each $R(\hat{t}_i, \hat{t}_j)$ is weighted by the difference between $\hat{t}_i$ and $\hat{t}_j$. The process of minimizing the $C_\omega$ (or C) seeks to move each pair of samples in $\Omega$ to satisfy $\hat{t}_i - \hat{t}_j > \gamma$ and thus to make $I(\hat{t}_i, \hat{t}_j) = 1$.

When the difference between the outputs of a pair in $\Omega$ is larger than the margin $\gamma$, this pair of samples will stop contributing to the objective function. This mechanism effectively overcomes over-fitting of the data during training of the model and makes the optimization preferably focus on only moving more pairs of samples in $\Omega$ to satisfy $\hat{t}_i - \hat{t}_j > \gamma$. The influence of the training samples is adaptively adjusted according to the pair-wise comparisons during training. Note that the positive margin $\gamma$ in R is preferable for improved generalization performance. In other words, the parameters of the neural network are adjusted during training by calculating the CI after all the patient data has been entered. The neural network then adjusts the parameters with the goal of minimizing the objective function and thus maximizing the CI. As used above, over-fitting generally refers to the complexity of the neural network. Specifically, if the network is too complex, the network will react to "noisy" data. Overfitting is risky in that it can easily lead to predictions that are far beyond the range of the training data.

Additional details regarding systems and methods for using an objective function substantially in accordance with an approximation of the CI to train a neural network are described in above-incorporated U.S. patent application Ser.

No. 11/067,066, filed Feb. 25, 2005, and U.S. Provisional Patent Application Nos. 60/548,322, filed Feb. 27, 2004, and 60/577,051, filed Jun. 4, 2004.

Figure 3:
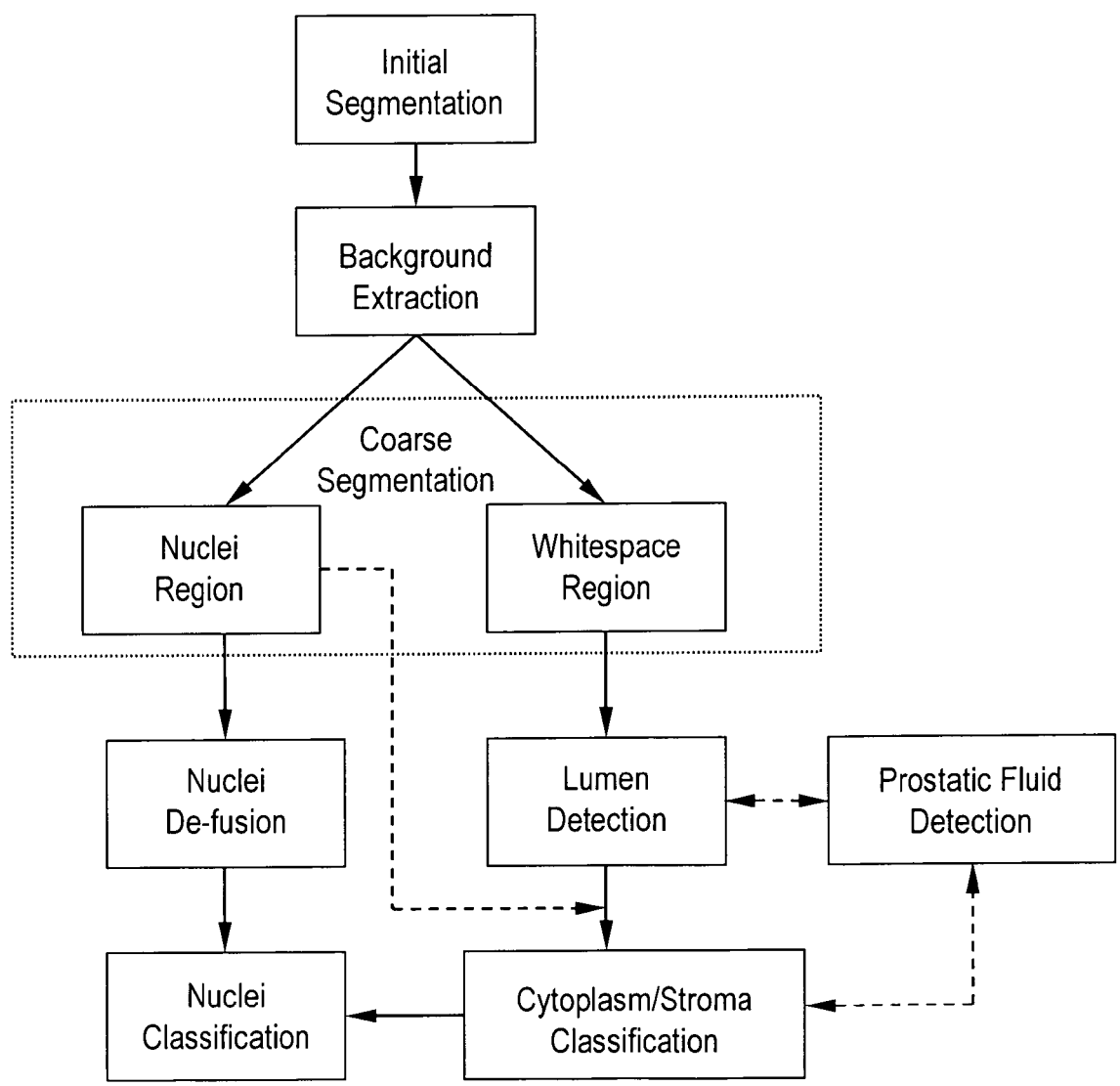
FIG. 3 is flowchart of illustrative stages involved in processing tissue images.

FIG. 3 is a flowchart of illustrative functions of a suitable image processing tool. The functions in FIG. 3 relate primarily to the segmentation of tissue images in order to classify pathological objects in the images (e.g., classifying objects as cytoplasm, lumen, nuclei, stroma, background, artifacts, and red blood cells). In one example, the image processing tool may include a light microscope that captures tissue images at 20× magnification using a SPOT Insight QE Color Digital Camera (KAI2000) and produces images with 1600×1200 pixels. The images may be stored as images with 24 bits per pixel in Tiff format. Such equipment is only illustrative and any other suitable image capturing equipment may be used without departing from the scope of the present invention. The image processing tool may also include any suitable hardware, software, or combination thereof for segmenting and classifying objects in the captured images, and then measuring morphometric features of the objects. In one embodiment, the image processing tool may include the commercially-available Definiens Cellenger Developer Studio (v. 4.0) adapted to perform the segmenting and classifying of, for example, the various pathological objects described above and to measure various morphometric features of these objects. Additional details regarding the Definiens Cellenger product are described in [10]. The image processing tool may measure various morphometric features of the objects including spectral-based characteristics (red, green, blue (RGB) channel characteristics, such as mean values, standard deviations, etc.), position, size, perimeter, shape (asymmetry, compactness, elliptic fit, etc.) and spatial and intensity relationships to neighboring objects (contrast). The image processing tool may measure these features for every instance of every identified pathological object in the image and may output these features for, for example, evaluation by predictive model 102 (FIG. 1A), test kit 122 (FIG. 1B), or analytical tool 132 (FIG. 1C). Optionally, the image processing tool may also output an overall statistical summary for the image for each of the measured features. Additional details regarding measuring morphometric features of the classified pathological objects are described below in connection with Tables 1 and 2. The following is a description of the functions shown in FIG. 3 of the image processing tool.

Initial Segmentation. In a first stage, the image processing tool may segment an image (e.g., an H&E stained tissue microarray (TMA) image or an H&E of a whole tissue section) into small groups of contiguous pixels known as objects. These objects may be obtained by a region-growing algorithm which finds contiguous regions based on color similarity and shape regularity. The size of the objects can be varied by adjusting a few parameters [11]. In this system, an object rather than a pixel is typically the smallest unit of processing. Thus, all morphometric feature calculations and operations may be performed with respect to objects. For example, when a threshold is applied to the image, the feature values of the object are subject to the threshold. As a result, all the pixels within an object are assigned to the same class. In one embodiment, the size of objects may be controlled to be 10-20 pixels at the finest level. Based on this level, subsequent higher and coarser levels are built by forming larger objects from the smaller ones in the lower level.

Background Extraction. Subsequent to initial segmentation, the image processing tool may segment the image tissue core from the background (transparent region of the slide) using intensity threshold and convex hull. The intensity threshold is an intensity value that separates image pixels in two classes: "tissue core" and "background". Any pixel with an intensity value greater than or equal the threshold is classified as a "tissue core" pixel, otherwise the pixel is classified as a "background" pixel. The convex hull of a geometric object is the smallest convex set (polygon) containing that object. A set S is convex if, whenever two points P and Q are inside S, then the whole line segment PQ is also in S.

Coarse Segmentation. In a next stage, the image processing tool may re-segment the foreground (e.g., TMA core) into rough regions corresponding to nuclei and white spaces. For example, the main characterizing feature of nuclei in H&E stained images is that they are stained blue compared to the rest of the pathological objects. Therefore, the difference in the red and blue channels (R−B) intensity values may be used as a distinguishing feature. Particularly, for every image object obtained in the initial segmentation step, the difference between average red and blue pixel intensity values may be determined. The length/width ratio may also be used to determine whether an object should be classified as nuclei area. For example, objects which fall below a (R−B) feature threshold and below a length/width threshold may be classified as nuclei area. Similarly, a green channel threshold can be used to classify objects in the tissue core as white spaces. Tissue stroma is dominated by the color red. The intensity difference d, "red ratio" r=R/(R+G+B) and the red channel standard deviation $\sigma_R$ of image objects may be used to classify stroma objects.

White Space Classification. In the stage of coarse segmentation, the white space regions may correspond to both lumen (pathological object) and artifacts (broken tissue areas) in the image. The smaller white space objects (area less than 100 pixels) are usually artifacts. Thus, the image processing tool may apply an area filter to classify them as artifacts.

Nuclei De-fusion and Classification. In the stage of coarse segmentation, the nuclei area is often obtained as contiguous fused regions that encompass several real nuclei. Moreover, the nuclei region might also include surrounding misclassified cytoplasm. Thus, these fused nuclei areas may need to be de-fused in order to obtain individual nuclei.

The image processing tool may use two different approaches to de-fuse the nuclei. The first approach may be based on a region growing algorithm that fuses the image objects constituting nuclei area under shape constraints (roundness). This approach has been determined to work well when the fusion is not severe.

In the case of severe fusion, the image processing tool may use a different approach based on supervised learning. This approach involves manual labeling of the nuclei areas by an expert (pathologist). The features of image objects belonging to the labeled nuclei may be used to design statistical classifiers.

In one embodiment, in order to reduce the number of feature space dimensions, feature selection may be performed on the training set using two different classifiers: the Bayesian classifier and the k nearest neighbor classifier [12]. The leave-one-out method [13] may be used for cross-validation, and the sequential forward search algorithm may be used to choose the best features. Finally, two Bayesian classifiers may be designed with number of features equal to 1 and 5, respectively. The class-conditional distributions may be assumed to be Gaussian with diagonal covariance matrices.

In some embodiments, the input image may include different kinds of nuclei: epithelial nuclei, fibroblasts, basal nuclei, endothelial nuclei, apoptotic nuclei and red blood cells. Since the number of epithelial nuclei is typically regarded as an important feature in grading the extent of the tumor, it may be important to distinguish the epithelial nuclei from the others.

The image processing tool may accomplish this by classifying the detected nuclei into two classes: epithelial nuclei and "the rest" based on shape (eccentricity) and size (area) features.

Additional details regarding image segmentation and classification in accordance with the present invention are described in above-incorporated U.S. patent application Ser. No. 10/991,897, filed Nov. 17, 2004, and U.S. Provisional Patent Application Nos. 60/520,815, filed Nov. 17, 2003 and 60/552,497, filed Mar. 12, 2004.

As described above, the image processing tool may measure various morphometric features subsequent to the segmenting and classifying of objects in the image by the tool. These morphometric features may be indicative of one or more properties and/or statistics. The object properties may include both spectral properties (e.g., color channel mean values, standard deviations and brightness) and structural/shape properties (e.g., area, length, width, compactness, density). The statistics may include minimum, maximum, mean and standard deviation and may be computed for each property of an image object. Tables 1 and 2 (appended hereto) show various examples of morphometric features that may be measured in accordance with the present invention. The morphometric features in these tables are named using a convention that indicates the various properties and/or statistics measured by these features. The particular naming convention shown in Tables 1 and 2 is adapted from the commercially-available Definiens software product described above and, therefore, will be understood by one of ordinary skill in the art.

It will be understood that the computer-generated morphometric features shown in Tables 1 and 2 are only illustrative and that any computer-generated morphometric features may be utilized without departing from the scope of the present invention. For example, Tables 1 and 2 include different sets of morphometric features. The reduced and modified set of features in Table 2 (i.e., reduced and modified in comparison to the features of Table 1) resulted from additional experimentation in the field of prostate cancer recurrence and survival from the time that the study involving Table 1 was performed. Particularly, the additional experimentation provided additional insight regarding the types of features which may be more likely to correlate with outcome. The inventors expect that continued experimentation and/or the use of other suitable hardware, software, or combination thereof will yield various other sets of computer-generated features (e.g., a subset of the features in Table 1 (see Tables 10 and 11) or a subset of the features in Table 2) that may correlate with these and other medical conditions.

Referring to Tables 1 and 2, the feature "Lumen.StdDevAreaPxl", "Lumen" indicates a type of image object, "StdDev" indicates a statistic (standard deviation) to be computed using all instances of the identified Lumen, and "AreaPxl" indicates a feature of an object instance (area as a number of pixels) to be evaluated by the statistic. An image processing tool may measure morphometric features for all the objects previously segmented and classified in the image. For example, the image processing tool may measure morphometric features for objects including "Background," "Cytoplasm," "Epithelial nuclei," "Lumen," "Stroma," "Stroma nuclei" and "Red blood cells." "Background" includes portions of the digital image that are not occupied by tissue. "Cytoplasm" refers to the cytoplasm of a cell, which may be an amorphous area (e.g., pink area that surrounds an epithelial nucleus in an image of, for example, H&E stained tissue). "Epithelial nuclei" refers to the nucleus present within epithelial cells/luminal and basal cells of the glandular unit, which appear as "round" objects surrounded by cytoplasm. "Lumen" refers to central glandular space where secretions are deposited by epithelial cells, which appear as enclosed white areas surrounded by epithelial cells. Occasionally, the lumen can be filled by prostatic fluid (which typically appears pink in H&E stained tissue) or other "debris" (e.g., macrophages, dead cells, etc.). Together the lumen and the epithelial cytoplasm and nuclei form a gland unit. "Stroma" refers to a form of connective tissue with different density that maintains the architecture of the prostatic tissue. Stroma tissue is present between the gland units, and appears as red to pink in H&E stained tissue. "Stroma nuclei" are elongated cells with no or minimal amounts of cytoplasm (fibroblasts). This category may also include endothelial cells and inflammatory cells, and epithelial nuclei may also be found scattered within the stroma if cancer is present. "Red blood cells" are small red round objects usually located within the vessels (arteries or veins), but can also be found dispersed throughout tissue.

"C2EN" in the below tables is a relative ratio of nucleus area to the cytoplasm. The more anaplastic/malignant the epithelial cell is, the more area is occupied by the nucleus and the greater the ratio. "EN2SN" is the percent or relative amount of epithelial to stroma cells present in the digital tissue image. "L2Core" is the number or area of lumen present within the tissue. The higher the Gleason grade, the more aggressive cancer is and therefore the less amount of lumen is present. Generally, this is because epithelial cells replicate in an uncontrolled way when cancer occurs, which causes lumen to become filled with the epithelial cells.

Figure 4:
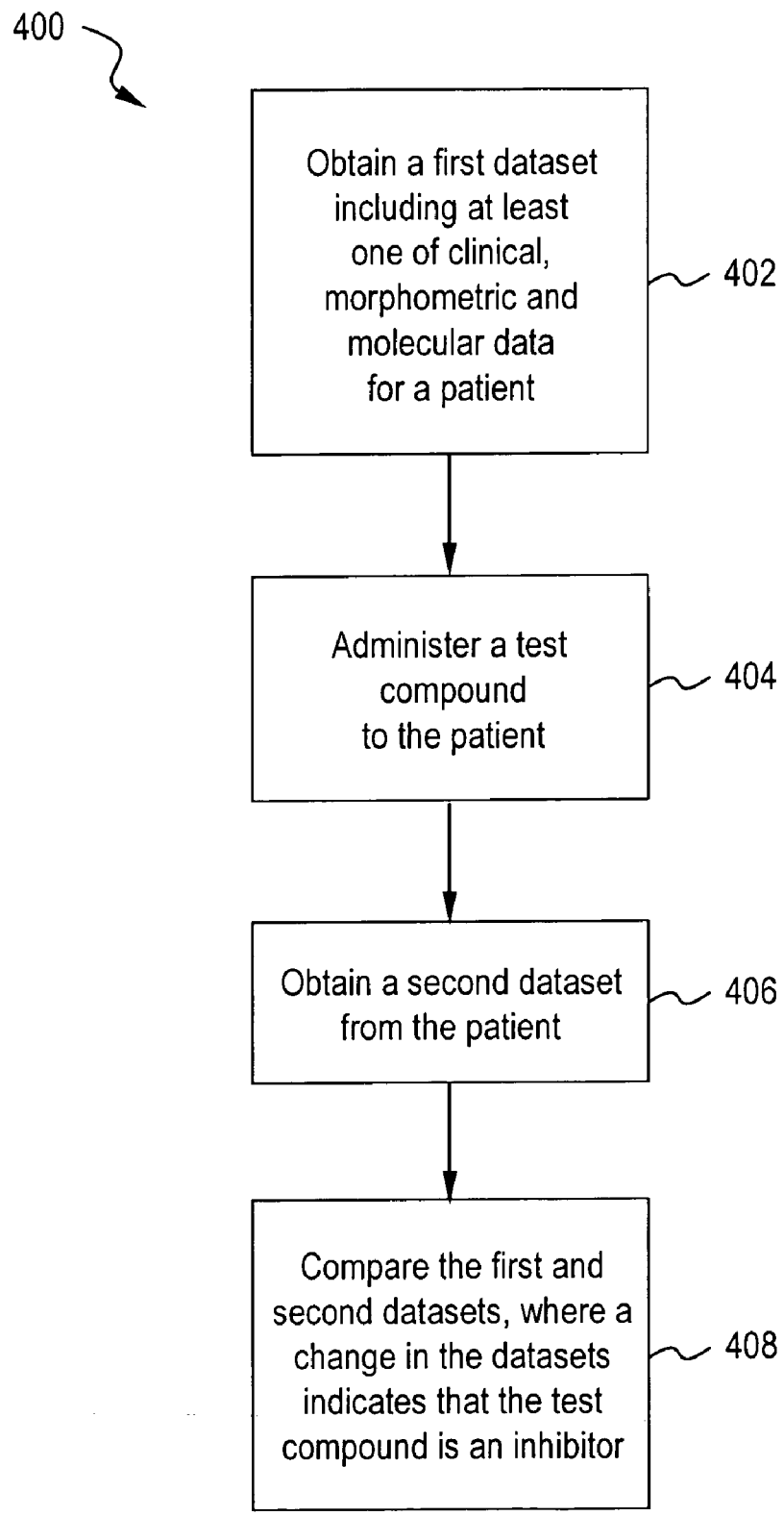
FIG. 4 is a flowchart of illustrative stages involved in screening for an inhibitor compound of a medical condition.

In an aspect of the present invention, systems and methods are provided for screening for an inhibitor compound of a medical condition (e.g., disease). FIG. 4 is a flowchart of illustrative stages involved in screening for an inhibitor compound in accordance with an embodiment of the present invention. At stage 402, a first dataset for a patient may be obtained that includes one or more of clinical data, morphometric data and molecular data. A test compound may be administered to the patient at stage 404. Following stage 404, a second dataset may be obtained from the patient at stage 406. The second dataset may or may not include the same data types (i.e., features) included in the first dataset. At stage 408, the second dataset may be compared to the first dataset, where a change in the second dataset following administration of the test compound indicates that the test compound is an inhibitor compound. Stage 408 of comparing the datasets may include, for example, comparing an output generated by a predictive model of the present invention responsive to an input of the first dataset with an output generated by the predictive model responsive to an input of the second dataset. For example, the inhibitor compound may be a given drug and the present invention may determine whether the drug is effective as a medical treatment for a medical condition.

Various illustrative applications of embodiments of the present invention to the prediction of medical conditions will now be described. In a first example, an embodiment of the present invention used clinical and morphometric data to predict the recurrence of prostate cancer. In a second example, an embodiment of the present invention used clinical, morphometric, and molecular data to predict the recurrence of prostate cancer and overall survivability. In a third example, an embodiment of the present invention was used to predict the occurrence of aggressive disease subsequent to a patient prostatectomy. In a fourth example, an embodiment of the present invention was used to predict liver toxicology. In fifth and sixth examples, embodiments of the present invention were used to predict prostate cancer recurrence. In a seventh example, an embodiment of the present invention was used to predict clinical failure post prostatectomy.

Prostate Cancer Overview

Prostate cancer is a leading cause of death among men in the United States with an anticipated 230,000 newly diagnosed cases and nearly 30,000 deaths in 2004. The expanded use of serum based screening with PSA has offered physicians the ability to detect prostate cancer at an earlier stage (i.e. T1a-c, T2), either localized to the prostate or regionally spread while only a small percentage are detected at the metastatic stage. The reported benefits of early detection and diagnosis have placed enormous pressure on both the patient and the urologist in selecting the course of treatment. The need for accurate prognosis is critical when selecting initial therapeutic intervention, as the majority of tumors are indolent and require minimal intervention (i.e. 'watchful waiting') while others are more aggressive and early intervention (i.e. radiotherapy/hormonal/adjuvant systemic therapy/clinical trial placement) is recommended. Furthermore, in a randomized trial comparing watchful waiting with radical prostatectomy, only a modest benefit was derived from surgery (6.6% reduction in mortality after prostatectomy) suggesting that better patient stratification measures are needed in order to guide individualized patient care [14].

The natural history of PCa re-emphasizes the challenges facing the patient at the time of their diagnosis [15]. Even though early stage prostate cancer is curable with local therapy, approximately 25-40% of men will develop a PSA/biochemical recurrence (BCR). To complicate matters even further, a man with prostate cancer who has had a recurrence can still develop a metastasis some 8 years post PSA/BCR (mean 8 years; median 5 years post BCR), suggesting that identifying this group of patients early in their treatment regimen (both in predicting their time to BCR as well as their propensity to develop metastases) is paramount to their overall survival. Unfortunately, the existing predictive models are limited in their accuracy and are not individualized for the specific patient with respect to their tumor pathology. Although a variety of genetic, environmental and life-style changes have been implicated in the pathogenesis of PCa, at present there is no single biochemical pathway, gene mutation or clinical biomarker which can predict a given patients outcome. Twenty-one years after radical prostatectomy became popular again and 15 years after the widespread use of PSA, urologists still cannot tell patients which treatment for localized disease results in the best clinical disease-free or overall survival.

Prognostic nomograms based only on clinical feature data do in fact provide useful predictions of clinical states and outcomes, but need improvement in both accuracy and universality [16]. Embodiments of the present invention provide a 'Systems Pathology' approach to successfully improve upon the accuracy of a predictive model for PSA/BCR post prostatectomy. This represents an 'individualized' view of the patients own tumor sample, including quantitative assessment of cellular and microanatomic morphometric characteristics, clinical profiles and molecular markers to create a highly accurate and integrative model of prediction. By utilizing domain expertise, highly accurate models for predicting PSA recurrence have been developed. These efforts have validated the utility of systems pathology in generating predictive and prognostic models. Furthermore, the analysis demonstrates that a limited set of clinical variables, molecular biomarkers, and tissue morphometric features can be derived and included in a predictive test used by urologists/pathologists to construct optimal patient treatment plans based on a designated clinical outcome. The selected molecular features which were associated with PSA recurrence suggest convergent roles for mechanisms of growth factor signaling (through the androgen receptor (hereinafter "AR"), described below) and cellular coupled vascularization (through CD34). CD34 is a transmembrane glycoprotein which is present on endothelial cells which line vessels in the human body. Further studies are underway to better understand these observations and the potential impact on predicting prostate cancer progression. Also of note were the selected image segmentation and morphometric characteristics which represent in part a highly accurate, non-subjective and quantitative Gleason Score in addition to several novel tissue descriptors which were important in model development and accuracy. The defined morphometric features relating to the Gleason Scoring System include in part the overall appearance of the glandular structures, shape and size (cytoplasmic composition) of the epithelial cells, epithelial cell nuclei and the demonstration of single epithelial cells admixed in the stroma.

The androgen receptor protein (AR) receives naturally occurring androgenic hormones (testosterone and its 5 .alpha.-reduced metabolite, dihydrotestosterone) after these hormones are synthesized by the Leydig cells of the male testes. Particularly, after synthesizing, these hormones circulate throughout the body and bind to the AR. Androgens, acting through the receptor AR, stimulate development of the male genitalia and accessory sex glands in the fetus, virilization and growth in the pubertal male, and maintenance of male virility and reproductive function in the adult. The androgen receptor, together with other steroid hormone receptors, constitute a family of trans-acting transcriptional regulatory proteins that control gene transcription through interactions with specific gene sequences.

Studies on AR with respect to prostate cancer have suggested that a positive correlation may exist between the presence of androgen receptors in cancer cells and their dependence on androgenic hormone stimulation for growth. For example, Sovak et al. U.S. Pat. No. 6,472,415 proposes that growth of prostate cancer in early stages is androgen driven and can, at least temporarily, be stopped by androgen deprivation. French et al. U.S. Pat. No. 6,821,767 proposes various ways for measuring AR that may allow for the use of androgen receptor assays in the diagnostic evaluation of prostate cancer by physicians. However, these studies have not proposed using measurements of AR in conjunction with automated models that predict the occurrence of prostate cancer, as disclosed herein.

EXAMPLE 1

Prediction of Prostate Cancer Recurrence

Clinical and Morphometric Data

A number of raw morphometric features initially as large as five hundred was extracted from each prostate tissue image using the MAGIC tissue image analysis system which is based on Definiens Cellenger software. The full set of raw features was chosen agnostically to avoid disregarding potentially useful features. However, all of these morphometric features were not likely to be equally informative, and a prediction model built based on the full feature set would be likely to have poor predictive performance due to the "curse of dimensionality" [13]. So a dimensionality reduction procedure was applied, and a set of eight morphometric features was finally selected.

A study was conducted based on a subset of 153 patients from a cohort of prostate cancer patients who underwent radical prostatectomy. Measurable prostate specific antigen (PSA) after the operation was used to define prostate cancer recurrence (also referred to as a biochemical recurrence (BCR)). Patients were followed post-operatively. Their recurrence status at their last visit, as well as their follow-up time, was recorded, which generated a set of right-censored data. Gleason scores were measured both pre-operatively from the biopsy specimen and post-operatively using the excised prostate gland. The four specific clinical measures, or features, considered in this study were (1) the biopsy Gleason grade, (2) the biopsy Gleason score, (3) the post-operative Gleason grade, and (4) the post-operative Gleason score.

The morphometric features were analyzed separately from the clinically derived Gleason score feature to predict both the probability and the time to PSA/BCR recurrence. The image and Gleason score (features) were then combined to establish a recurrence and time to recurrence time prediction. Improved prediction accuracy achieved by this joint set of features indicated that the image features indeed provided additional information and thus enhanced the recurrence prediction rate and the overall prediction model.

Because this cohort of patients had right-censored outcome data, survival analysis models had to be built for the prediction of recurrence. In order to avoid the potential algorithmic bias on different types of data, two survival analysis algorithms were used: 1) a Cox regression model [17]; and 2) SVRc which is described above and as applied to a support vector machine. The concordance index estimated using 5-fold cross validation was used to measure the models' predictive accuracy [13] [18].

Both algorithms were applied to three data sets: (1) the Gleason score clinical features alone; (2) the selected morphometric features alone; and (3) the combination of the morphometric features and the Gleason score clinical features. The experimental results are listed in Table 3.

The clinical features selected in this example were BXGGTOT, BXGG1, GGTOT, and GG1 and the morphometric features selected related to epithelial nuclei (Epithelial.Nuclei.MaxCompactness), background (Background.StdDevAreaPxl), and lumen (Lumen.MaxBorderLengthPxl, Lumen.MinRadiusofsmallestenclosinge, Lumen.StdDevBorderLengthPxl, Lumen.SumBorderlengthPxl, Lumen.StdDevAreaPxl, and Lumen.MinCompactness). More particularly, in this example, morphometric features related to the area, border length, and shape (compactness) of the lumen were determined to correlate with disease progression. The smaller and more compact the lumen, the more advanced the cancer was likely to be. Indeed, with more aggressive cancer (Gleason grade 4 and 5), it can be expected that lumen will almost or completely disappear from the tissue. It was also determined that the morphometric feature of compactness of epithelial nuclei correlated with cancer progression, where compactness was calculated by the Definiens Cellenger software as the ratio of the length and width product of the epithelial nuclei to the epithelial nuclei area. This may be because epithelial nuclei invasion into stroma increases as cancer progresses (i.e., tissue with advanced cancer typically includes an abundance of epithelial nuclei). The background-based morphometric feature that was determined to correlate with outcome in this example measured the actual size of the tissue core used in the analysis.

TABLE 3

Comparison of Prediction Accuracy

|      | Gleason | Image  | Gleason + Image |
|------|---------|--------|-----------------|
| Cox  | 0.6952  | 0.6373 | 0.7261          |
| SVRc | 0.6907  | 0.7269 | 0.7871          |

According to Table 3, the predictive performance of the morphometric features is comparable with that of the Gleason scores, and the combination of the morphometric features and the Gleason scores achieves a higher predictive rate, which confirms that the morphometric features extracted by the tissue image analysis system indeed provide extra information beyond the Gleason scores. Therefore, the use of the morphometric measurements can enhance overall recurrence prediction.

EXAMPLE 2

Prediction of Prostate Cancer Recurrence and Overall Survival

Clinical, Morphometric and Molecular Data

Two studies were conducted which successfully predicted prostate specific antigen (PSA) recurrence with 88% and 87% predictive accuracies, respectively. By combining clinical, molecular, and morphometric features with machine learning, a robust platform was created which has broad applications in patient diagnosis, treatment management and prognostication. A third study was conducted to predict overall survival of prostate cancer patients, where the outcome of interest was death due to any cause.

A cohort of 539 patients who underwent radical prostatectomy was studied incorporating high-density tissue microarrays (TMAs) constructed from prostatectomy specimens. Morphometric studies were performed using hematoxylin and eosin (H&E) stained tissue sections and molecular biological determinants were assessed with immunohistochemistry (IHC). A predictive model for both PSA recurrence and overall survival was derived from a selected set of features through supervised multivariate learning. Patients with complete non-missing data in each domain were evaluated with a support vector machine for regression developed to handle censored data (SVRc). Predictive performance of the model was estimated using the concordance index (CI) with generated scores used to define risk groups.

Using a cohort of 132 patients, 41 features (including 17 clinical, 14 molecular, and 10 morphometric) were selected which predicted PSA recurrence with 88% accuracy. In a cohort of 268 patients, 10 features (3 clinical, 1 molecular, and 6 morphometric) were found to be predictive of PSA recurrence with 87% accuracy; additionally, 14 features (2 clinical, 1 molecular, and 11 morphometric) were found to be predictive of overall survival with 80% accuracy. Using the log-rank test, significant differences in tumor recurrence and death were observed between risk groups (p<0.0001).

The present study reveals an incremental trend of improved prostate cancer recurrence prediction through the use of a new systems approach combining clinical variables, molecular markers, and tissue histology, analyzed by machine learning.

Patient Clinical Features. A cohort of 539 patients who underwent radical prostatectomy was studied. Seventeen clinical features (shown below in Table 4) were retrospectively collected using de-identified patient information, which included patient age, preoperative PSA, and Gleason Grade.

TABLE 4

Clinical Features Collected

| Feature | Description |
|---|---|
| age | Age (in years) |
| race | Race |
| prepsa | Prostate specific antigen (ng/dl) |
| tnm | TNM clinical stage |
| uicc | UICC clinical stage |
| dre | Palpable on digital rectal exam |
| ln | Lymph node status |
| svi | Invasion of the seminal vesicles |
| margins | +/−surgical margins |
| ece | Tumor located outside capsule |
| bxgg1 | Dominant biopsy Gleason Grade |
| bxggtot | Biopsy Gleason Score |
| gg1 | Dominant post-operative Gleason Grade |
| ggtot | Post-operative Gleason Score |
| prsltcd | Diploid, Tetraploid, Aneuploid |
| pp_sphas | Percent of cells in ploidy in S phase |
| pp_frac | Ploidy proliferation fraction |

Tissue microarrays (TMAs) were constructed from selected blocks of the prostatectomy specimens. Tissue cores with a diameter of 0.6 mm from each specimen were randomly arrayed in triplicate for each of the recipient paraffin blocks (Beecher Instruments, Silver Spring, Md.). Sections (5 μm) of these TMA blocks were placed on charged poly-lysine-coated slides, and used for morphometric and immunohistochemical (IHC) analyses (see below).

Missing values for clinical features were imputed with flexible additive regression models containing all of the features to estimate the value of the missing feature without reference to outcome, and only those patients with complete clinical (after imputation), morphometric, and molecular data, as well as non-missing outcome information, were further studied. The effective sample size for Study 1 (proof of concept) consisted of 132 patients. The primary classification of interest was whether a patient recurred or not after surgery for prostate cancer. Patients who had two observed consecutive elevations in PSA>0.2 ng/mL were considered to have recurrent prostate cancer. If a patient did not recur as of his last visit, or the patient outcome was unknown as of his most recent visit (i.e. due to loss-to-follow-up), then the patient's outcome was considered censored. Time to recurrence was defined as the time (in months) from radical prostatectomy until PSA (biochemical) recurrence.

Study 2 was performed using 268 patients from the original 539 patient cohort including 129 of the 132 patients from Study 1. Instead of utilizing H&E images derived from TMA cores, whole sections from radical prostatectomies were analyzed. Study 3 examined the same 268-patient cohort but was used to predict overall survival, where the outcome of interest was death due to any cause.

Image Analysis and Morphometry Studies. Representative areas of the original tumor tissue retrieved from each patient, either from a tissue core or whole section, were digitized and analyzed using the H&E stained slides. Images were captured with a light microscope at 20× magnification using a SPOT Insight QE Color Digital Camera (KAI2000). Only areas containing greater than 80% tumor were selected for optimal image segmentation and quantitative analysis.

Molecular Analysis. A panel of 12 biomarkers including Cytokeratin 18 (luminal cells), Cytokeratin 14 (basal cells), CD45 (lymphocytes), CD34 (endothelial cells), CD68 (macrophages), Ki67 (proliferation), PSA (hK-3, kallikrein), PSMA (growth receptor), Cyclin D1 (cell cycle), p27 (cell cycle), Androgen Receptor (endocrine) and Her-2/neu (signaling) were applied across all 7 TMA blocks with standard chromogenic immunohistochemistry. Antigen retrieval was performed with a 0.01M citrate buffer (pH 6) for 30 min in a pressure cooker for all antibodies. Illustrative methods and systems relating to such a process are described in above-incorporated U.S. patent application Ser. No. 10/624,233, filed Jul. 21, 2003, and entitled "Methods and compositions for the preparation and use of fixed-treated cell-lines and tissue in fluorescence in situ hybridization." Primary antibodies (shown in Table 5) were diluted in Tris-buffered saline with 0.1% Tween and applied for 16 h at 4° C. followed by biotinylated secondary antibodies (Vector) at 1:1000 dilution for 1 h.

TABLE 5

List of Antibodies

| Biomarker | Clone |
|---|---|
| Ki-67 | Clone ki-67 (DAKO) |
| Cytokeratin18 | Clone DC-10 (Novocastra) |
| CD45 | Clone X16/99 |
| CD68 | Clone 514H2 (Novocastra UK) |
| CD34 | Clone QBEnd 101 (DAKO) |
| AR | Clone AR27 (Novocastra) |
| Cytokeratin14 | Clone LL002 (Novocastra) |
| Cyclin D1 | Clone P2D11F11 |
| PSA | Clone PA05 (Neomarkers) |
| PSMA | Clone ZMD.80 (Zymed)$^P$ |
| p27 | Clone DCS72 (Oncogene) |
| Her-2/neu | KIT DAKO$^P$ |

$^P$polyclonal, the rest are monoclonal

Negative control slides received normal mouse serum (DAKO) as the primary antibody. Slides were counterstained with Harris hematoxylin and reviewed by two independent pathologists with all discrepancies resolved by a third pathologist. The recorded IHC data from all 539 patients and their respective triplicate cores included the percentage and intensity (0-3+) of cells which stained for a particular antigen under investigation. Where applicable, these two measures were combined to create a Staining Index for that particular biomarker (Table 6, below, shows an exemplary list of molecular features). A Staining Index was calculated for AR (Androgen Receptor), CK14 (Cytokeratin 14), Cyclin D1, PSA (Prostate Specific Antigen), PSMA (Prostate Specific Membrane Antigen), p27 and Her2/neu while the remaining markers (i.e., Ki67, CK18 (Cytokeratin 18), CD45, CD68) were evaluated based on percentage of positive cells with a given intensity. These biomarkers are further described below. The Staining Index ranged from 0-300, and was calculated as follows: 1*(the percentage of cells staining positive with 1+ intensity for a biomarker)+2*(the percentage of cells staining positive with 2+ intensity for the biomarker)+3*(the percentage of cells staining positive with 3+ intensity for the biomarker), where the percentage of cells staining positive refers to the number of positive cells identified per every 100 cells counted. Additional details regarding this staining index are described in [19]. Such a staining index is only illustrative and any other suitable way for measuring molecular features may be used without departing from the scope of the present invention.

In the discussion of biomarkers above, p27 belongs to the family of cell cycle regulators called cyclin-dependent kinase inhibitors, which bind to cyclin-CDK complexes and cause cell cycle arrest in the G1 phase. The biomarker p27 is postulated to promote apoptosis and play a role in terminal differentiation of some tissues. By immunohistochemistry, the loss of nuclear p27 expression is associated with a more aggressive phenotype. Her2/neu is a member of the EGFR family of receptor tyrosine kinases and plays an important role in the pathogenesis of certain human cancers. The overexpression of Her2/neu by immunohistochemistry on cellular membranes has been associated with a more aggressive type of breast cancer. Ki67 is one of many proliferative markers that stains the nucleus with varying degrees of intensity and is utilized to assess a proliferative index or measure of cellular activity of the tumor sample in question. CD45 is a cell surface antigen that is used to identify cells that are destined to become immune cells such as lymphocytes (T cells, B-cells, NK cells etc.). The intensity is believed not to be as important as its distribution/presence and association with other histological elements. CD68 is a cytoplasmic antigen closely associated with lysosomes. It is expressed throughout the monocyte differentiation cascade but is usually more intense in macrophages than monocytes.

TABLE 6

Molecular Features

| Feature | Description |
|---|---|
| atki67t1 | Ki-67 in intensity area 1 (tumor) |
| atki67t2 | Ki-67 in intensity area 2 (tumor) |
| atki67t3 | Ki-67 in intensity area 3 (tumor) |
| atki67p1 | Ki-67 in intensity area 1 (PIN) |
| atki67p2 | Ki-67 in intensity area 2 (PIN) |
| atki67p3 | Ki-67 in intensity area 3 (PIN) |
| atki67a1 | Ki-67 in intensity area 1 (gland) |
| atki67a2 | Ki-67 in intensity area 2 (gland) |
| atki67a3 | Ki-67 in intensity area 3 (gland) |
| atc18t3 | Cytokeratin18 (tumor) |
| atcd45t3 | CD45 (tumor) |
| atcd68t3 | CD68 (tumor) |
| atcd34p | CD34 (PIN) |
| atcd34s | CD34 (stroma) |
| atcd34t | CD34 (tumor) |
| atcd34tp | CD34 (tumor/PIN) |
| atcd34ts | CD34 (tumor/stroma) |
| atcd34ps | CD34 (PIN/stroma) |
| atc18p3 | Cytokeratin 18 (PIN) |
| atcd45p3 | CD45 (PIN) |
| atc18a3 | Cytokeratin 18 (gland) |
| atcd45a3 | CD45 (gland) |
| arsi | AR (tumor) staining index |
| c14si | Cytokeratin 14 (tumor) staining index |
| cd1si | Cyclin D1 (tumor) staining index |
| psasi | PSA (tumor) staining index |
| psmasi | PSMA (tumor) staining index |
| p27si | p27 (tumor) staining index |
| her2si | Her-2/neu (tumor) staining index |
| arpsi | AR (PIN) staining index |
| c14psi | Cytokeratin 14 (PIN) staining index |
| cd1psi | Cyclin D1 (PIN) staining index |
| psapsi | PSA (PIN)staining index |
| psmapsi | PSMA (PIN)staining index |
| p27psi | p27 (PIN)staining index |
| her2psi | Her-2/neu (PIN) staining index |
| arasi | AR (gland) staining index |
| c14asi | Cytokeratin 14 (gland) staining index |
| cd1asi | Cyclin D1 (gland) staining index |
| psaasi | PSA (gland) staining index |
| psmaasi | PSMA (gland) staining index |
| p27asi | p27 (gland) staining index |
| her2asi | Her-2/neu (gland) staining index |

Analytical and Statistical Studies. Three studies were conducted: an initial proof of concept analysis (Study 1) with 132 patients and an extended investigation (Study 2 and Study 3) using 268 patients. In both Study 1 and Study 2, the analysis consisted of two steps: identifying features predictive of PSA recurrence and developing a model based on those features, with the ultimate objective of using the model to predict biochemical (PSA) recurrence in future radical prostatectomy patients. The goals of Study 3 were to identify features and develop a model for predicting overall survival post-prostatectomy. Support Vector Regression for Censored data (SVRc) of the type described above was used to develop the resulting models in each of these studies.

Figure 8:
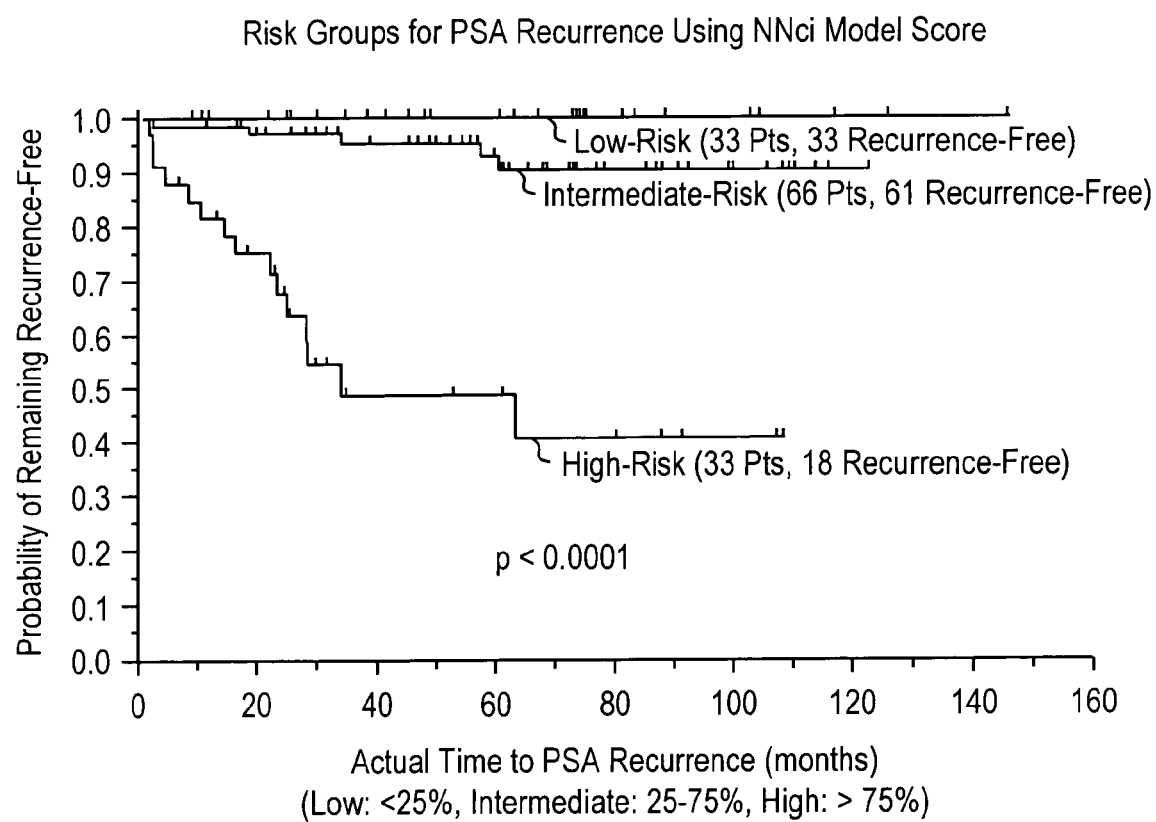
FIG. 8 is a graph of a Kaplan-Meier curve demonstrating a classification of patients as being at low-risk, intermediate-risk, or high-risk for experiencing prostate cancer recurrence as predicted by a model based on the features of FIG. 6.
Figure 10:
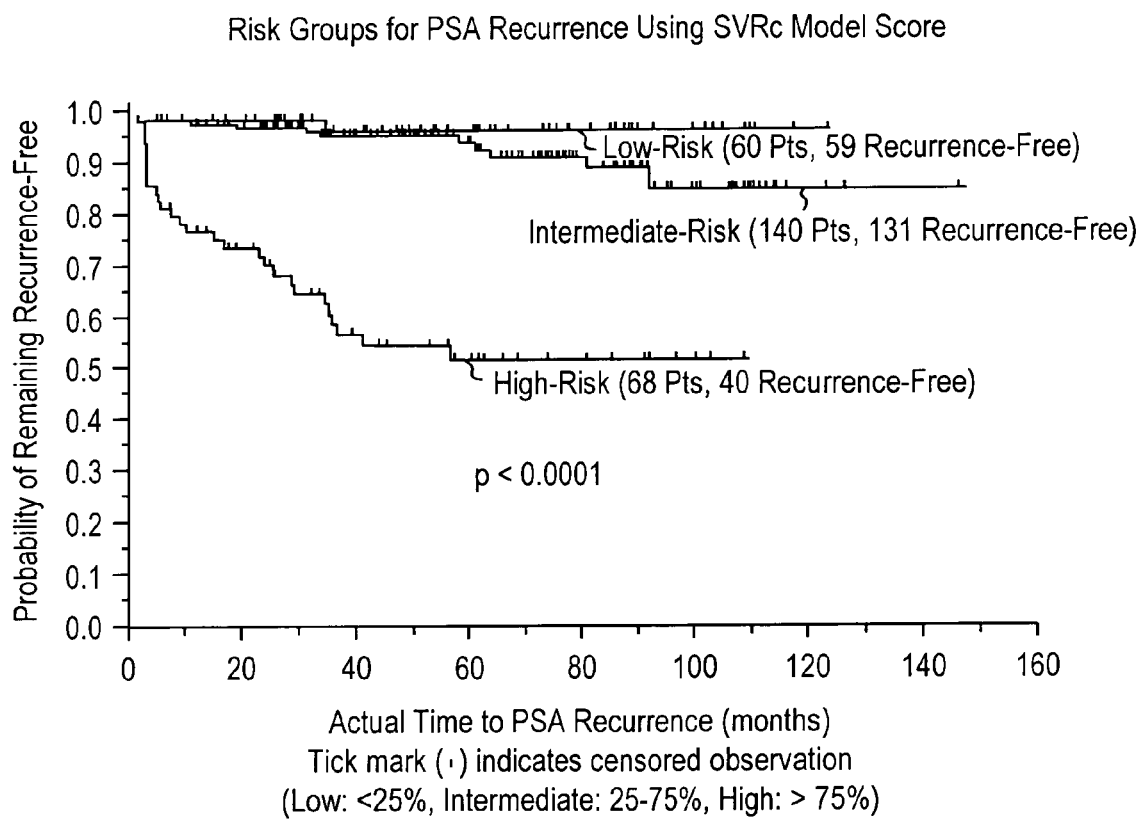
FIG. 10 is a graph of a Kaplan-Meier curve demonstrating a classification of patients as being at low-risk, intermediate-risk, or high-risk for experiencing prostate cancer recurrence as predicted by a model based on the features of FIG. 9.

Predictive accuracy of a model was evaluated using the concordance index (CI). In dealing with censored outcomes this is often the metric of choice. The concordance index is based on pairwise comparisons between the prognostic scores of two randomly selected patients who meet any one of the following criteria: both patients experienced the event and the event time of the first patient is shorter than that of the second patient or only the first patient experienced the event and his event time is shorter than the second patient's follow-up time. The CI estimates the probability that a patient with the higher prognostic score from the model will experience the event within a shorter time than a patient with a lower score and is tightly associated with the area under the ROC curve (AUC). Other metrics may also be used to measure the ability of a predictive model. For example, sensitivity and specificity may be used in assessing diagnostics. As another example, a "p-value" may be used that represents the probability that chance alone is responsible for, for example, the observed differences between strata (e.g., see FIGS. 8, 10, and 12). Therefore, the lower the p-value, the more likely there is a true statistical association with outcome. Typically, the standard is that any p-value less than or equal to 0.05 is statistically significant.

Study 1. In this analysis, the above-described SVRc model was applied sequentially to the clinical, molecular, and morphometric data, with the clinical features first serving as an anchor for a "greedy-forward" feature selection ("FS") algorithm via SVRc run on the molecular data. Following this step, a second SVRc greedy-forward feature selection algorithm on the morphometric data was run, using the combination of the clinical and selected molecular features as the anchor. The last step involved running a greedy-backward selection algorithm on the combination of the clinical, selected molecular and selected morphometric features to derive a final model. During feature selection, the criterion to determine whether a feature was entered (or kept) in the model was based on whether the presence (or absence) of that feature increased the concordance index, i.e. added predictive information.

The model was evaluated for predictive accuracy using both internal and external validation. Internal validation was performed using five-fold cross-validation. In order to perform external validation, a series of test sets of patients was created from the cohort of patients and predicted outcome was compared to actual outcome for these patients via the concordance index. In applying this two-level validation design, a subset of patients were randomly selected from the full set of patient records and only the remaining patients were used to build the predictive model using the procedure just described. The withheld records were then used to apply to the trained model in order to get a predictive accuracy. These two steps were repeated B times to get B predictive rates where the final predictive rate was the average. Features selected for the final model were those that appeared a sufficient amount of times in the B distinct models created.

Using the selected feature set, a neural network model was developed via directly maximizing the concordance index. Particularly, a neural network (NNci) of the type described above was used, in which network was trained using an objective function substantially in accordance with an approximation of the concordance index. The output of this final model was used to estimate individual future patient risk for PSA recurrence.

Study 2. The goals of this study were identical to Study 1; however, different feature selection and validation procedures were used. Instead of using the anchoring approach, all of the features were ranked by their association with time to PSA recurrence (measured by the concordance index) and those features which passed a certain pre-determined threshold (CI≧0.60) were selected. This was done after the number of imaging features was reduced by our domain experts, and these features were then evaluated in a series of n-feature models (e.g. 1-feature, 2-feature, 3-feature, etc.). Using a forward feature selection process, the features that maximized the concordance index of each n-feature model were used in the next n+1-feature model. This process ended once the CI could not be improved by a pre-determined threshold. Then using a backward feature selection process, features were removed in an effort to increase the CI. This process was terminated when the removal of any feature did not improve the CI.

A simple bootstrapping technique was used for feature selection. In this approach, patients were sampled with replacement and used as a training set while the model was evaluated on those not selected. As a comparison, this feature selection algorithm was run using only those features found in the Kattan post-operative nomogram, which is described in Kattan et al U.S. Pat. No. 6,409,664, which is hereby incorporated by reference herein in its entirety. The output of the final model was used to estimate individual future patient risk for PSA recurrence.

Study 3. The goal of this study was to identify features predictive of overall survival using the same cohort and feature set analyzed in Study 2 as well as the same feature selection algorithm. The output of the final model was used to estimate individual future patient risk for death due to any cause.

Results

The general approach was to apply systems pathology (the combination of morphometric analyses, molecular signatures and patient clinical profiles) to develop predictive models for PSA recurrence and overall survival in a cohort of prostate cancer patients status post prostatectomy. It is important to note that when clinicopathological features alone from Study 1 were utilized in a standard Cox Model analysis, the accuracy for predicting PSA recurrence was only 59%. It was only after the integration of morphometric and molecular features with SVRc that the level of predictive accuracy was increased to 88%. The following sections describe how this improvement was achieved.

Study 1. For the 132 patients in this cohort, the median age at diagnosis was 63 years (min: 40, max: 81), and the median pre-operative PSA was 8.2 ng/dl (min: 1.1, max: 81.9). Based on the prostatectomy samples, 32% had a Gleason score less than 7, 60% were Gleason 7 and the remaining 8% were greater than 7. Sixty-nine patients (52%) were pT2N0M0, 40 patients (30%) pT3aN0M0, and the remaining 23 patients (18%) pT3bN0M0 or pT1-3N+. (Table 7 contains a summary list of clinical characteristics for the three studies).

TABLE 7

Clinical Information

| | Study 1 | Study 2 and 3 |
|---|---|---|
| N | 132 | 268 |
| Age (years) | | |
| Mean | 62 | 62 |
| Median | 63 | 63 |
| Range | 40-81 | 40-81 |
| Race | | |
| Caucasian | 120 (90.9%) | 241 (89.9%) |
| Hispanic | 8 (6.1%) | 12 (4.5%) |
| African-American | 2 (1.5%) | 9 (3.4%) |
| Unknown | 2 (1.5%) | 6 (2.2%) |
| Pre-operative PSA (ng/dl) | | |
| Mean | 12.2 | 10.8 |
| Median | 8.2 | 7.8 |
| Range | 1.1-81.9 | 0.9-81.9 |
| TNM Stage | | |
| pT2N0 | 69 (52.3%) | 157 (58.6%) |
| pT3aN0 | 40 (30.3%) | 72 (26.9%) |
| pT3bN0 | 13 (9.8%) | 22 (8.2%) |
| pT1-3N+ | 10 (7.6%) | 17 (6.3%) |
| UICC Stage | | |
| T1a <5% | 0 (0.0%) | 1 (0.3%) |
| T1b ≧5% | 0 (0.0%) | 1 (0.3%) |
| T1c not palpable or visible | 49 (37.1%) | 112 (41.8%) |
| T2a ≦½ lobe | 23 (17.4%) | 58 (21.7%) |
| T2b ≦1 lobe | 27 (20.5%) | 45 (16.8%) |
| T2c both lobes | 23 (17.4%) | 34 (12.7%) |
| T3a unilateral ECE | 8 (6.1%) | 15 (5.6%) |
| T3c SV+ | 2 (1.5%) | 2 (0.8%) |
| DRE Result | | |
| Non-palpable | 56 (42.4%) | 118 (44.0%) |
| Palpable | 76 (57.6%) | 150 (56.0%) |
| Lymph Node Involvement | | |
| Negative | 121 (91.7%) | 250 (93.3%) |
| Positive | 11 (8.3%) | 18 (6.7%) |
| Seminal Vesicle Involvement | | |
| No | 113 (85.6%) | 236 (88.0%) |
| Yes | 19 (14.4%) | 32 (12.0%) |
| Surgical Margins | | |
| Negative | 108 (81.8%) | 217 (81.0%) |
| Positive | 24 (18.2%) | 51 (19.0%) |
| Extracapsular Involvement | | |
| No | 70 (53.0%) | 159 (59.3%) |
| Yes | 62 (47.0%) | 109 (40.7%) |
| Dominant Biopsy Gleason Grade | | |
| 1 | 0 (0.0%) | 1 (0.4%) |
| 2 | 24 (18.2%) | 43 (16.0%) |
| 3 | 85 (64.4%) | 184 (68.7%) |
| 4 | 22 (16.7%) | 38 (14.2%) |
| 5 | 1 (0.7%) | 2 (0.8%) |
| Biopsy Gleason Score | | |
| 2 | 0 (0.0%) | 1 (0.4%) |
| 3 | 0 (0.0%) | 0 (0.0%) |
| 4 | 6 (4.6%) | 7 (2.6%) |
| 5 | 27 (20.5%) | 56 (20.9%) |
| 6 | 41 (31.1%) | 97 (36.2%) |
| 7 | 48 (36.4%) | 90 (33.6%) |
| 8 | 7 (5.3%) | 13 (4.9%) |
| 9 | 3 (2.3%) | 4 (1.5%) |

TABLE 7-continued

Clinical Information

|  | Study 1 | Study 2 and 3 |
|---|---|---|
| Dominant Post-operative Gleason Grade | | |
| 2 | 3 (2.3%) | 20 (7.5%) |
| 3 | 98 (74.2%) | 201 (75.0%) |
| 4 | 31 (23.5%) | 47 (17.5%) |
| Post-operative Gleason Score | | |
| 5 | 6 (4.6%) | 21 (7.8%) |
| 6 | 36 (27.3%) | 86 (32.1%) |
| 7 | 79 (59.9%) | 148 (55.2%) |
| 8 | 10 (7.6%) | 12 (4.5%) |
| 9 | 1 (0.8%) | 4 (0.4%) |
| Ploidy | | |
| Diploid | 74 (56.1%) | 145 (54.1%) |
| Tetraploid | 54 (40.9%) | 115 (42.9%) |
| Aneuploid | 4 (3.0%) | 8 (3.0%) |
| Percent Ploidy in S Phase (%) | | |
| Mean | 2.3 | 2.4 |
| Median | 1.1 | 1.1 |
| Range | 0.0-63.8 | 0.0-66.4 |
| Percent Ploidy Fraction | | |
| Mean | 3.4 | 3.5 |
| Median | 2.6 | 2.4 |
| Range | 0.0-20.0 | 0.0-20.0 |

Twenty (15%) patients experienced PSA recurrence, while the remaining patients (85%) were censored. For censored patients, the median follow-up time was 60.8 months, or just over 5 years. The overall median time to PSA recurrence was not reached. All seventeen clinical features were selected as being predictive of PSA recurrence, with the most informative being annotated as follows (clinicopathological feature and # of times selected by the model): biopsy Gleason grade (112), race (112), UICC clinical stage (110), ploidy (110), and DRE results (109).

Figure 5A:
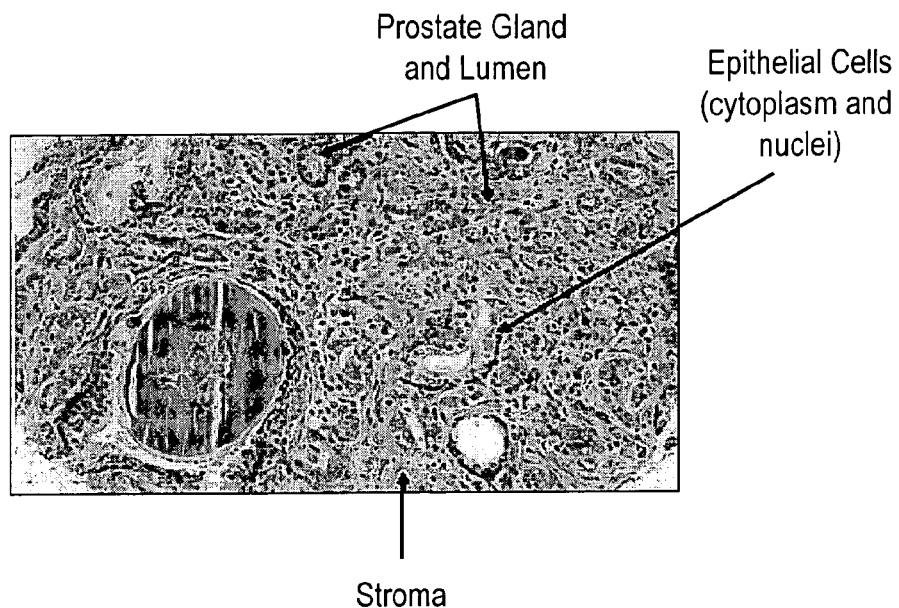
FIGS. 5a and 5b show grayscale digital images of healthy and abnormal prostate tissue specimens, respectively, after image segmentation and classification.
Figure 5B:
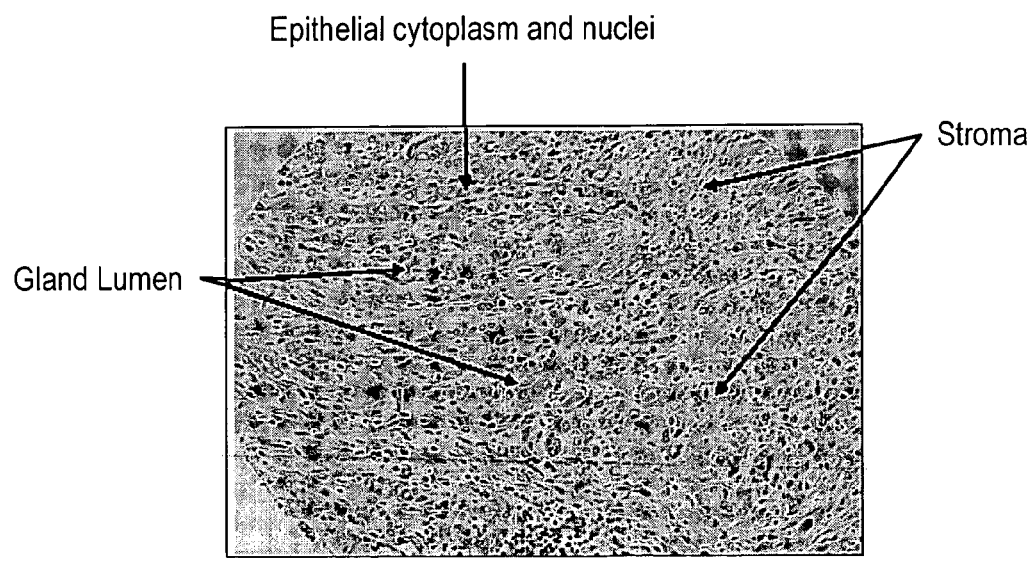

Image Analysis and Morphometry Studies. FIGS. 5a and 5b illustrate digitized images of healthy and abnormal prostate tissue, respectively, obtained after segmentation and classification in accordance with the present invention. Various pathological objects have been labeled in the tissue for illustration. A total of 496 morphometric features (shown in Table 1) were generated by the image analysis software.

Of the 496 morphometric features, the 10 morphometric features shown in FIG. 6 were selected as being predictive of PSA recurrence. The morphometric features selected related to the following pathological objects, where the numbers in parentheses next to the features indicate how many times the features were selected as correlated with outcome during generation of the final model: red blood cell, epithelial nuclei, lumen, stroma, cytoplasm, and tissue background (Red Blood Cell Minimum Length in Pixels (20), Epithelial Nuclei Maximum Compactness (17), Lumen Minimum Radius of Smallest Enclosure (14), Epithelial Nuclei Minimum Width in Pixels (11), Stroma Maximum Density (10), Lumen Maximum Border Length in Pixels (10), Epithelial Nuclei Minimum Standard Deviation Channel 2 (10), Epithelial Nuclei Maximum Radius of Smallest Enclosure (10), Cytoplasm Standard Deviation of Border Length in Pixels (10), and Background Standard Deviation of Area in Pixels (10)). More particularly, in this example, the morphometric features of length for red blood cell, radius of smallest enclosure and border length for lumen, border length for cytoplasm, density for stroma (e.g., square root of the area covered by a stroma divided by its radius), and area for background were determined to correlate with outcome. The morphometric features of compactness, width, green channel value, and radius of smallest enclosure for epithelial nuclei (e.g., ellipse with the same area as the object is created and then enlarged until it completely encloses the epithelial nuclei, and the ratio of the radius of the smallest enclosing ellipse to the radius of the original ellipse is computed) were also determined to correlate with outcome.

Various possible reasons for at least some of these correlations are described above in connection with Example 1. For example, the morphometric feature of compactness of the epithelial nuclei may be a reflection of the 'back to back' nature of epithelial cells in a circumferential pattern which would suggest a loss of glandular and lumen formation/differentiation and therefore be consistent with a higher Gleason grade (i.e., higher disease progression). Also, the morphometric feature of the radius of smallest enclosure of the lumen relates to the overall size of the lumen which is dramatically reduced and diminished as the Gleason grade increases.

In addition, the correlations determined in this study may be at least partially explained by the hypothesis that epithelial nuclei typically become less diverse in shape (e.g., more round with less variations) and size (e.g., area and border length) and have less color variation as the epithelial nuclei invade the stroma. This invasion of the stroma may also explain why morphometric features of the stroma have been determined to be correlated with disease progression. Particularly, cancerous images are typically characterized by a small amount of stroma because the stroma area is replaced by epithelial cell cytoplasm as cancer progresses. This causes density values for stroma to be higher because the stroma compactness is reduced and becomes more fractal in shape (the object radius increases more than the area as objects deform and become thinner). Additional reasoning for the correlations determined in this study may be that an abundance of red blood cells traveling through the tissue may reflect some measure of angiogenesis or new blood vessel formation which may be related to disease progression as a means for cells to leave the prostate and seed externally—thus impacting on the clinical outcome of PSA/BCR recurrence.

As stated above, it will be understood that at least some of the particular morphometric features determined by the teachings provided herein to correlate with outcome may depend on, for example, the particular hardware, software, or combination thereof that is used by the present invention to calculate the morphometric features. The Definiens Cellenger software and the particular morphometric features measured by the software described herein are only illustrative and any other hardware, software, or combination thereof may be used without departing from the scope of the invention.

Molecular Analysis. Of the 12 biomarkers that were evaluated by IHC, a total of 43 unique features were recorded. (Tables 8a, 8b, and 8c, below, show a summary of the observed biomarker—molecular features).

TABLE 8a

Cells (%) Staining (+) by Histologic Component and Intensity (Study 1)

| Marker | Tumor | | | PIN | | | Gland | | |
|---|---|---|---|---|---|---|---|---|---|
| | 1+ | 2+ | 3+ | 1+ | 2+ | 3+ | 1+ | 2+ | 3+ |
| Ki-67 | | | | | | | | | |
| Mean ± SD | 23.9 ± 31.38 | 9.8 ± 21.32 | 2.4 ± 4.64 | 25.3 ± 32.50 | 10.3 ± 21.51 | 2.6 ± 3.29 | 1.8 ± 9.96 | 0.0 ± 0.36 | 0.1 ± 0.63 |
| Median | 4.7 | 0.0 | 0.0 | 4.8 | 0.0 | 0.0 | 0.0 | 0.0 | 0.0 |
| Range | 0.0-100.0 | 0.0-100.0 | 0.0-26.3 | 0.0-100.0 | 0.0-100.0 | 0.0-39.5 | 0.0-96.0 | 0.0-4.0 | 0.0-6.3 |
| CK 18 | | | | | | | | | |
| Mean ± SD | NA | NA | 100.0 ± 0.00 | NA | NA | 100.0 ± 0.00 | NA | NA | 100.0 ± 0.00 |
| Median | NA | NA | 100.0 | NA | NA | 100.0 | NA | NA | 100.0 |
| Range | NA | NA | 100.0-100.0 | NA | NA | 100.0-100.0 | NA | NA | 100.0-100.0 |
| CD45 | | | | | | | | | |
| Mean ± SD | NA | NA | 0.0 ± 0.04 | NA | NA | 0.0 ± 0.01 | NA | NA | 0.0 ± 0.00 |
| Median | NA | NA | 0.0 | NA | NA | 0.0 | NA | NA | 0.0 |
| Range | NA | NA | 0.0-0.4 | NA | NA | 0.0-0.1 | NA | NA | 0.0-0.0 |
| CD68 | | | | | | | | | |
| Mean ± SD | NA | NA | 0.0 ± 0.01 | NA | NA | NA | NA | NA | NA |
| Median | NA | NA | 0.0 | NA | NA | NA | NA | NA | NA |
| Range | NA | NA | 0.0-0.1 | NA | NA | NA | NA | NA | NA |

TABLE 8b

CD34 Cells (%) Staining (+) by Histologic Component (Study 1)

| | PIN | Stroma | Tumor | Tumor/PIN | Tumor/Stroma | PIN/Stroma |
|---|---|---|---|---|---|---|
| Mean ± SD | 0.0 ± 0.05 | 0.0 ± 0.03 | 0.1 ± 0.21 | 0.0 ± 0.06 | 0.0 ± 0.08 | 0.0 ± 0.05 |
| Median | 0.0 | 0.0 | 0.0 | 0.0 | 0.0 | 0.0 |
| Range | 0.0-0.4 | 0.0-0.2 | 0.0-0.9 | 0.0-0.5 | 0.0-0.4 | 0.0-0.3 |

TABLE 8c

Staining Index (0-300) by Histologic Component (Study 1)

| Marker | Tumor | PIN | Gland |
|---|---|---|---|
| AR | | | |
| Mean ± SD | 179.8 ± 71.4 | 64.3 ± 75.10 | 22.6 ± 56.86 |
| Median | 200 | 36.5 | 0 |
| Range | 0-300 | 0-300 | 0-300 |
| CK14 | | | |
| Mean ± SD | 2.6 ± 5.83 | 31.2 ± 57.35 | 4.7 ± 20.42 |
| Median | 0 | 0 | 0 |
| Range | 0-42 | 0-285 | 0-150 |
| Cyclin D1 | | | |
| Mean ± SD | 1.5 ± 5.15 | 0.0 ± 0.27 | 0.0 ± 0.0 |
| Median | 0 | 0 | 0 |
| Range | 0-33 | 0-3 | 0-0 |
| PSA | | | |
| Mean ± SD | 128.0 ± 68.85 | 135.7 ± 97.88 | 13.9 ± 41.32 |
| Median | 100 | 111 | 0 |
| Range | 0-300 | 0-300 | 0-201 |
| PSMA | | | |
| Mean ± SD | 0.5 ± 2.97 | 9.5 ± 26.93 | 2.5 ± 15.00 |
| Median | 0 | 0 | 0 |
| Range | 0-21 | 0-154 | 0-99 |
| p27 | | | |
| Mean ± SD | 4.3 ± 9.61 | 7.0 ± 19.49 | 2.1 ± 12.03 |
| Median | 0 | 0 | 0 |
| Range | 0-80 | 0-140 | 0-120 |
| Her-2/neu | | | |
| Mean ± SD | 4.1 ± 18.50 | 0.1 ± 1.00 | 0.0 ± 0.00 |
| Median | 0 | 0 | 0 |
| Range | 0-146 | 0-10 | 0-0 |

Figure 7A:
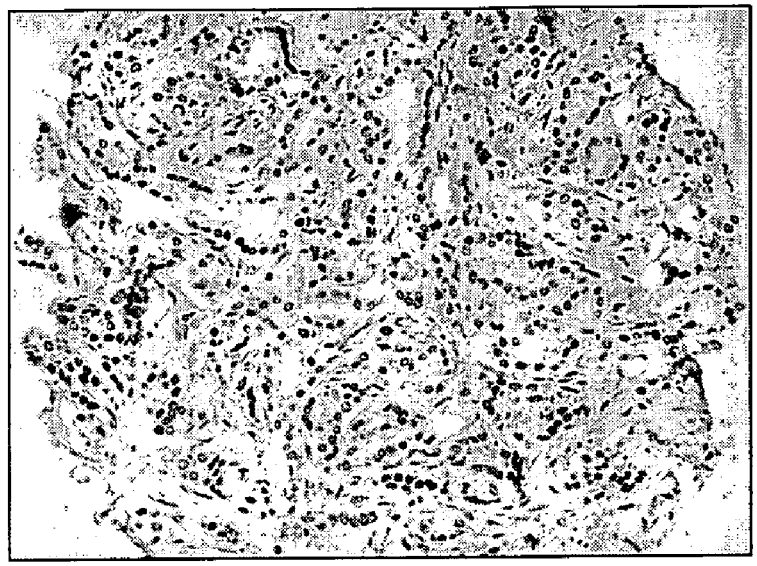
FIGS. 7a and 7b show stained tissue specimens demonstrating the presence of two molecular features, particularly Androgen Receptor (AR) and CD34.
Figure 7B:

From these 12 antibodies, 8 biomarkers encompassing 14 specific molecular features were selected as being associated with PSA recurrence. Some examples of the more highly selected molecular features are annotated as follows (biomarker—# times selected by the model) and include: AR Staining Index—tumor (93), AR Staining Index—atrophic gland (54), CD34—associated Tumor/PIN (22), Ki-67—tumor (18) and CD45—associated with PIN (17), where PIN is an abbreviation for prostatic intraepithelial neoplasm. FIGS. 7a and 7b illustrate representative fields demonstrating expression profiles for AR and CD34, respectively. The profile of biomarker expression was noteworthy for the highly selected and somewhat heterogeneous expression patterns of AR and CD34. These markers and their relationship to tumor, atrophic glands (for AR) and Tumor/PIN (for CD34) suggest biological and functional significance impacting on the clinical outcome of PSA recurrence. The second group of selected markers included Ki-67 and CD45 both of which had prominent but overall low selection frequency when compared with AR and CD34.

Analytical and Statistical Studies. Using both domain expertise and domain-specific feature selection procedure above where 120 random splits were created for training (N=100) and testing (N=32) the models, the final feature set was reduced to 41 total features of which 17 were clinical, 10 morphometric, and 14 molecular. FIG. 5 shows a complete list of the selected features. The 10 morphometric features are described above. The clinical and molecular features are further described below.

Clinical Features

1. Biopsy Gleason Score: the summarized Gleason grades (dominant and secondary) which are assigned to the multiple Needle Biopsy Tissue Samples received by a pathologist. The Gleason scoring system was developed to create a standardized, somewhat subjective, means of representing the architecture of prostatic adenocarcinoma by histology with the production of individual grades. The grades range from 1-5 based on the degree of differentiation of the glandular units and epithelial cells. The dominant (primary) and sub-dominant (secondary) patterns are added together to create a Gleason Summary. In addition, the features of overall stromal compactness, epithelial cell size and nuclear features are occasionally considered in the overall grading system.
2. Race (e.g., African American, Caucasian, etc.)
3. UICC Stage: International Union against Cancer TNM staging system use to define clinical staging for cancer, where "T" stands for Tumor size, "N" stands for lymph node involvement and "M" stands for metastasis to a distant site.
4. Ploidy Result: DNA content which is a reflection of the overall DNA content within the prostate cancer epithelial cells. Benign cells and well-behaved tumor cells grow and divide in an orderly fashion. In the resting state, they contain one complete set of chromosomes (this is the diploid condition). This complete set of chromosomes consists of 23 chromosomes (or N) from Ma and 23 (N again) chromosomes from Pa (equaling a total of 2N). A cell must double the number of its chromosomes before it can divide, creating two complete sets of chromosomes (this is 4N, or the tetraploid state). After division is completed, each new cell receives half of the genetic material and therefore becomes diploid (2N) once again. If DNA ploidy analysis were to be performed on a group of these cells, one would see that most of the cells would be diploid and a small fraction of them (those getting ready to divide) would be tetraploid. Additionally, in measuring and creating a graph of the amount of genetic material in each cell, one would see a dominant diploid peak and a minor tetraploid peak. The amount of DNA in a cell can be measured by staining it with a dye that binds to the genetic material. The concentration and distribution of this dye (Fuelgen stain) can be measured by image analysis microscopy.

When tumors worsen they tend to not divide as orderly as they once did. Instead of the resting state having a complete set of chromosomes, the resting state may only have a set and a half. Such cells would have a DNA content that was neither diploid nor tetraploid but mid-way between. Plotting these cells on the above-described graph above would yield an aneuploid peak midway between the other two peaks. Studies have shown that tumors that have a significant aneuploid peak do not behave as well as those that do not. This is not surprising because a strong correlation exists between ploidy status and nuclear grade. A nuclear grade can be assessed by any pathologist with enough experience with prostate cancer. The value that DNA ploidy analysis adds is that it is an objective measurement that can be compared between labs using standardized techniques and that can be used to perform a quick check on the approximate accuracy of Gleason scoring. For example, any Gleason score 2+2=4 or 2+3=5 tumor that has an aneuploid peak should potentially be re-evaluated for possible adjustment to the score.

5. DRE Result: Result from a digital rectal exam (e.g., negative or positive) which is utilized to determine extent of disease both within the prostate as well as extra prostatic extension by palpation.
6. Lymph Node Involvement: a measure of the extent to which lymph nodes contain tumor cells (e.g., prostate cancer epithelial cells), which can be assessed either by clinical/surgical inspection or at the time of a prostatectomy.
7. Dominant Biopsy Gleason Grade: See above description of Biopsy Gleason Score. This reflects the dominant Gleason grading pattern seen on either a biopsy or a prostatectomy specimen.
8. Percent Ploidy in S Phase: represents a fraction of the cellular content which is in a proliferative or S phase of the cell cycle and reflects the growth potential of the tumor.
9. Post-operative Gleason Score: Scoring of tissue taken after surgery from various regions of the prostate resection sample.
10. TNM Stage: Tumor, Node and Metastasis based on the UICC criteria post prostatectomy and based on pathologic examination of tissue samples.
11. Dominant Post-operative Gleason Grade: the dominant Gleason grade which represents the most predominant histologic feature present in the prostatectomy specimen.
12. Age
13. Seminal Vesicle Involvement: Invasion of the seminal vesicle by tumor.
14. Pre-operative PSA: PSA level observed prior to surgery
15. Percent Ploidy Fraction: See above description of ploidy result.
16. Surgical Margin Involvement: Involvement of the surgical margins by tumor which reflects the extent to which the bed from which the tumor/prostate was removed at the time of surgery contained tumor cells.
17. Extracapsular Involvement: Extension of the tumor beyond the capsule of the prostate.

Molecular Features

1. AR—tumor: Androgen Receptor (AR) Staining Index for a tumor, which is a measure of the percentage and intensity of cells staining positive for AR. With respect to prostate cancer, the staining index may represent the degree of brown reaction product which is detected in the nuclei of epithelial cells in the prostate samples evaluated.
2. AR—gland: AR Staining Index for a tumor, which is present within a glandular structure.
3. CD34—tumor/PIN: The localization of CD34 to the endothelial cells of vessels which are associated with tumor and PIN.

4. Ki67—tumor 2: The identification of ki67 positive nuclei in tumor epithelial cell nuclei.
5. CD45—PIN 3: The identification f CD45 positive lymphocytes in association with PIN.
6. CD34—tumor/stroma: The localization of CD34 vessels which are associated with tumor.
7. Ki-67—tumor 3: see above.
8. p27—tumor: The identification of p27 in the nuclei of tumor epithelial cells.
9. C14—PIN: The identification of cytokeratin 14 in the (epithelial) basal cells of the glandular unit.
10. CD34—tumor: The localization of CD34 to vessels which are associated with the tumor.
11. PSA—gland: The identification of PSA to the luminal epithelial cells of the gland unit.
12. PSMA—PIN: The identification of PSMA to the glandular/luminal cells of regions identified as PIN.
13. CD34—PIN/stroma: The localization of CD34 to vessels associated with PIN.
14. CD45—tumor 3: The identification of CD45 positive lymphocytes which are associated with tumor.

As each domain of data was analyzed during this process using SVRc, the predictive accuracy of the models increased. Using internal validation, when looking at the clinical data alone, the concordance index was 0.79. By adding features from the molecular domain, the concordance index increased to 0.81. The final model, formed by the addition of the morphometric features, reached a concordance index of 0.84. Each of these internally-validated models was also validated externally (as described above in Materials and Methods) with the same trend being noted. Using NNci on the final selected set of features, the concordance index reached 0.88.

The resulting output of the NNci and the SVRc models can be interpreted as a relative risk estimate of PSA recurrence for an individual patient. Using the quartiles of this score ($\leq 25\%$, $>25\%-75\%$, $>75\%$), risk groups of patients were created; the Kaplan-Meier estimates of recurrence for each risk group according to the NNci model are presented in FIG. 8. The groups showed a statistically significant difference in time to PSA recurrence (log-rank test, p-value<0.0001). The p-value represents the probability that chance alone is responsible for the observed differences between strata (risk groups in these examples). Therefore, the lower the p-value, the more likely you are seeing a true statistical association. Generally, any p-value less than or equal to 0.05 is statistically significant.

Study 2. For the 268 patients in this cohort, which contains 129 of the 132 patients analyzed in Study 1, the median age at diagnosis was 63 years (min: 38, max: 81), and the median PSA prior to radical prostatectomy was 7.8 ng/dl (min: 0.9, max: 81.9). Based on the prostatectomy samples, 40% of tumors had a Gleason Score less than 7, while 55% of the prostatectomies had a Gleason 7. The remaining 5% of prostatectomies had a Gleason Score greater than 7. One hundred fifty-seven patients (59%) were diagnosed as having pT2N0M0 disease, 72 patients (27%) as pT3aN0M0, and the remaining 39 patients (14%) as pT3bN0M0 or pT1-3N+. (See Table 5, supra for details of all analyzed clinicopathological features for this cohort). Thirty-eight (14%) patients experienced PSA recurrence, while the remaining patients (86%) were censored. For censored patients, the median follow-up time was 58.7 months, or just under 5 years. The overall median time to PSA recurrence was not reached. Three clinical features were selected as being predictive of PSA recurrence: TNM clinical stage, surgical margins, and lymph nodes.

Image Analysis and Morphometry Studies. Using an updated version of the image analysis software but analyzing the same H&E stained slides, a total of 350 morphometric features were generated (shown in Table 2, above).

FIG. 9 shows that, of the 350 features, 6 morphometric features were selected as being predictive of PSA recurrence, where these morphometric features related to the pathological objects of epithelial nuclei, stroma, cytoplasm, red blood cell, and lumen (i.e., EpithelialNucleiMinCompactne0215, StromaMaxStddevChannel30569, CytoplasmStddevMaxDiff0148, RedBloodCellMeanAreaPxl0386, RedBloodCellStddevAreaPxl0388, and LumenMinAsymmetry0295). More particularly, in this study, the morphometric features of compactness of epithelial nuclei, blue channel value for stroma, max difference for cytoplasm (e.g., minimum mean value belonging to cytoplasm subtracted from its maximum value over all color channels for the cytoplasm, where the result is divided by the object brightness), area for red blood cells, and asymmetry of lumen were selected as being correlated with outcome.

Various possible reasons for at least some of these correlations are described above in connection with Example 1 and/or Study 1. For example, morphometric features including the compactness of the epithelial cells, the variation and disruption of the stroma by infiltrating epithelial cells, and the evidence of reduced lumen size would all provide histologic evidence of a higher Gleason grade (i.e., higher disease progression). A higher Gleason grade suggests a more aggressive prostate tumor which would support metastasis and or extension of tumor supporting PSA recurrence post surgery. In addition, the identification of red blood cells in various formats would suggest an abundance of vessels. The evidence of additional vessels would create a possible route for which epithelial cells could exit the prostate and be distributed in external locations producing PSA.

Clinical and molecular features selected in study 2 are shown in FIG. 9 and listed below. Descriptions of these clinical and molecular features are provided above.

Clinical Features
1. TNM stage
2. Surgical Margin Involvement
3. Lymph Node Involvement Molecular Feature
1. AR Staining Index (tumor)

Each number in FIG. 9 represents the concordance index of a predictive model based on the corresponding feature and all other feature(s) in FIG. 9 having smaller number(s). For example, 0.8483 is the CI of a model based on features TNM Clinical Stage, Surgical Margins, EpithelialNucleiMinCompactne0215, Lymph Nodes, and StromaMaxStddevChannel30569. The CI of a model based on the same 5 features plus AR Staining Index (tumor) is 0.8528. In other words, the addition of the AR Staining Index molecular feature to the model increases the predictive power of the model.

Molecular Analysis. No additional immunohistochemistry studies were necessary. The data originally collected was used as described in Materials and Methods (see Tables 9a, 9b, and 9c for a complete summary of the molecular features).

TABLE 9a

Cells (%) Staining (+) by Histologic Component and Intensity (Study 2 and Study 3)

| Marker | Tumor | | | PIN | | | Gland | | |
|---|---|---|---|---|---|---|---|---|---|
| | 1+ | 2+ | 3+ | 1+ | 2+ | 3+ | 1+ | 2+ | 3+ |
| Ki-67 | | | | | | | | | |
| Mean ± SD | 22.1 ± 30.30 | 7.3 ± 17.04 | 1.9 ± 4.01 | 23.2 ± 31.36 | 7.9 ± 18.16 | 2.0 ± 4.46 | 1.3 ± 7.96 | 1.2 ± 9.78 | 0.3 ± 1.55 |
| Median | 1.3 | 0.0 | 0.0 | 1.0 | 0.0 | 0.0 | 0.0 | 0.0 | 0.0 |
| Range | 0.0-100.0 | 0.0-100.0 | 0.0-26.3 | 0.0-100.0 | 0.0-100.0 | 0.0-39.5 | 0.0-96.0 | 0.0-96.5 | 0.0-13.0 |
| CK 18 | | | | | | | | | |
| Mean ± SD | NA | NA | 100.0 ± 0.00 | NA | NA | 1.0 ± 0.04 | NA | NA | 100.0 ± 0.00 |
| Median | NA | NA | 100.0 | NA | NA | 100.0 | NA | NA | 100.0 |
| Range | NA | NA | 100.0-100.0 | NA | NA | 0.5-100.0 | NA | NA | 100.0-100.0 |
| CD45 | | | | | | | | | |
| Mean ± SD | NA | NA | 0.0 ± 0.04 | NA | NA | 0.0 ± 0.01 | NA | NA | 0.0 ± 0.00 |
| Median | NA | NA | 0.0 | NA | NA | 0.0 | NA | NA | 0.0 |
| Range | NA | NA | 0.0-0.4 | NA | NA | 0.0-0.1 | NA | NA | 0.0-0.0 |
| CD68 | | | | | | | | | |
| Mean ± SD | NA | NA | 0.0 ± 0.01 | NA | NA | NA | NA | NA | NA |
| Median | NA | NA | 0.0 | NA | NA | NA | NA | NA | NA |
| Range | NA | NA | 0.0-0.1 | NA | NA | NA | NA | NA | NA |

TABLE 9b

CD34 Cells (%) Staining (+) by Histologic Component (Study 2 and Study 3)

| | PIN | Stroma | Tumor | Tumor/PIN | Tumor/Stroma | PIN/Stroma |
|---|---|---|---|---|---|---|
| Mean ± SD | 0.0 ± 0.04 | 0.0 ± 0.11 | 0.1 ± 0.18 | 0.0 ± 0.08 | 0.0 ± 0.08 | 0.0 ± 0.04 |
| Median | 0.0 | 0.0 | 0.0 | 0.0 | 0.0 | 0.0 |
| Range | 0.0-0.4 | 0.0-1.7 | 0.0-0.9 | 0.0-0.6 | 0.0-0.4 | 0.0-0.3 |

TABLE 9c

Staining Index (0-300) by Histologic Component (Study 2 and Study 3)

| Marker | Tumor | PIN | Gland |
|---|---|---|---|
| AR | | | |
| Mean ± SD | 172.1 ± 75.3 | 79.6 ± 82.74 | 28.9 ± 67.25 |
| Median | 200 | 66.0 | 0 |
| Range | 0-300 | 0-300 | 0-300 |
| CK14 | | | |
| Mean ± SD | 2.1 ± 6.32 | 34.4 ± 61.46 | 8.5 ± 32.62 |
| Median | 0 | 0 | 0 |
| Range | 0-69 | 0-300 | 0-300 |
| Cyclin D1 | | | |
| Mean ± SD | 1.4 ± 6.99 | 0.0 ± 0.21 | 0.0 ± 0.0 |
| Median | 0 | 0 | 0 |
| Range | 0-90 | 0-3 | 0-0 |
| PSA | | | |
| Mean ± SD | 118.3 ± 71.10 | 139.4 ± 97.16 | 22.8 ± 55.14 |
| Median | 100 | 134 | 0 |
| Range | 0-300 | 0-300 | 0-300 |
| PSMA | | | |
| Mean ± SD | 0.2 ± 2.09 | 6.4 ± 21.02 | 2.9 ± 22.94 |
| Median | 0 | 0 | 0 |
| Range | 0-21 | 0-154 | 0-300 |
| p27 | | | |
| Mean ± SD | 3.9 ± 8.20 | 6.4 ± 18.83 | 1.3 ± 8.65 |
| Median | 0 | 0 | 0 |
| Range | 0-48 | 0-140 | 0-120 |
| Her-2/neu | | | |
| Mean ± SD | 3.4 ± 16.69 | 0.2 ± 1.12 | 0.0 ± 0.00 |
| Median | 0 | 0 | 0 |
| Range | 0-150 | 0-10 | 0-0 |

A single molecular feature was selected as being predictive of PSA recurrence: AR Staining Index—tumor.

Analytical and Statistical Studies. Using domain expertise and simple bootstrapping, the algorithm found a subset of 10 features (3 clinicopathological, 6 morphometric, and 1 molecular) that had a concordance index (CI) of 0.87 (Table 9, above, shows the complete list of selected features). The resulting output of the SVRc model can also be interpreted as a relative risk estimate of PSA recurrence for an individual patient. Using the quartiles of this score (<25%, >25%-75%, >75%), risk groups of patients were created; the Kaplan-Meier estimates of recurrence for each risk group as predicted by the SVRc model are presented in FIG. 10. The groups showed a statistically significant difference in time to PSA recurrence (log-rank test, p-value<0.0001).

Study 3. This study used the same cohort as that of Study 2 so that the clinicopathological characteristics of the patients are identical. In terms of outcome, nineteen (7%) patients died due to any cause, while the remaining patients (93%) were alive as of their last visit and censored. For censored patients, the median follow-up time was 64.8 months, or just over 5 years. The overall median time to death was not reached. Two clinical features were selected as being predictive of death due to any cause: TNM clinical stage and patient age.

Image Analysis and Morphometry Studies. The same set of 350 morphometric features from Study 2 was used in this study. FIG. 11 shows that, of the 350 features, 11 morphometric features were selected as being predictive of death due to any cause, where these features related to the pathological objects of stroma, red blood cell, and epithelial nuclei (i.e., StromaMinMeanChannel10535, RedBloodCellMeanStddevChann30474, StromaMinMeanChannel20539, RedBloodCellMinMeanChannel20443, RedBloodCellStddeStddeChann20472, StromaMaxMaxDiff0529, EpitheNucleMeanBordeLengtPxl0206, EpithelialNucleiMeanAreaPxl0194, EpithelNucleiStddevElliptFit0228, RedBloodCellStddeStddeChann30476, and RedBloodCellStddevElliptiFit0420, where "channel" refers to the red (R), green (G), and blue (B) color channels of an image). More particularly, in this study, the morphometric features of mean value of red color channel, mean value of blue color channel and max difference for stroma were determined to be correlated with outcome. The morphometric features of mean and standard deviation of red channel, mean and standard deviation of green channel and elliptic fit for red blood cell were determined to be correlated with outcome. To determine the morphometric feature of elliptic fit, an ellipse with the same area as the red blood cell was created, the area of the red blood cell outside the ellipse was compared with the area inside the ellipse that was not filled with the red blood cell, and a value of 0 was assigned where there was no fit whereas a value of 1 was assigned for a complete fitting object. The morphometric features of border length, area and elliptic fit for epithelial nuclei were determined to be correlated with outcome.

Various possible reasons for at least some of these correlations are described above in connection with Example 1 and/or Study 1. For example, the overall shape of the epithelial nuclei reflects a histologic appearance of a higher Gleason grade. Additionally, in this study, the correlation with respect to stroma may be explained by the understanding that stroma will exhibit a reduced contrast (as measured by the max difference morphometric feature) as cancer progresses due to its interruption with epithelial cells.

Molecular Analysis. The same set of molecular features from Study 2 was used in this study. A single feature was selected as being predictive of death due to any cause: PSA Staining Index—atrophic gland.

Analytical and Statistical Studies. In this cohort, a total of 14 features (2 clinicopathological, 11 morphometric, and 1 molecular) were selected. The final model had a concordance index (CI) of 0.80. The complete list of selected features are shown in FIG. 11 and listed below. The clinical and molecular features selected are listed below. Descriptions of the clinical features are provided above.

Clinical Features
1. TNM stage
2. age

Molecular Feature
1. psapsi: refers to the staining index for prostate specific antigen (PSA) in the prostatic intraepithelial neoplasm (PIN).

Each number in FIG. 11 represents the concordance index of a predictive model based on the corresponding feature and all other feature(s) in FIG. 11 having smaller number(s). For example, 0.6804 is the CI of a model based on StromaMinMeanChannel10535 and 0.7362 is the CI when the model is based on both StromaMinMeanChannel10535 and TNM.

The resulting output of the SVRc model can also be interpreted as a relative risk estimate of death for an individual patient. Using the quartiles of this score (<25%, >25%-75%, >75%), risk groups of patients were created; the Kaplan-Meier estimates of recurrence for each risk group as predicted by the SVRc model are presented in FIG. 12. Using the log-rank test, a significant difference in survival was observed between risk groups (p<0.0001).

Discussion of Results (Example 2)

The observed reduction of (composite) selected features from Study 1(41) to Study 2(10) while retaining the predictive accuracy of the model emphasized the precision and filtering attributes that were achieved through different machine learning algorithms. The concordance index of the model that was developed in the 268-patient cohort was 0.87; by comparison, when the Kattan nomogram [20] is applied to this cohort it achieved a concordance index of 0.78. Perhaps more striking is the ability of the above model as discussed in Study 2 to correctly classify patients with early PSA recurrences (within 5 years) with a sensitivity of 80%. By comparison, the Kattan nomogram is able to make the same prediction with a sensitivity of only 54%. This further emphasizes the role that such a predictive test would serve in decision making for early intervention. Finally, the output of the model presented can be used to estimate the likelihood of a patient recurring over time, as opposed to offering a single estimate of the probability of a patient recurring within a given number of years without any indication as to when within that time frame.

In Study 3 the objective was to utilize the existing domain knowledge derived from Study 2 and develop a predictive model for overall survival. The successful end result was the ability to predict with 80% accuracy an individual's overall survival and time to death utilizing a total of 14 combined domain features. Although limited by the small number of events (7% dead from any cause) and absence of a comparable published nomogram, the results further support the use of a systems approach for developing these types of predictive tests.

Additional efforts are underway with respect to expanding this 'overall survival' analysis to include clinical measures of poor outcome (i.e., metastasis and or death due to prostate cancer) utilizing a retrospective multi-institutional population with an independent external validation study. In addition, a 'Systems Pathology' approach recently has been initiated to interrogate diagnostic needle biopsies in order to have an impact on treatment issues prior to surgery.

The foregoing example demonstrates that a 'Systems Pathology' platform has been successfully developed which integrates clinical features, tumor tissue morphometrics and molecular analyses. By using domain expertise and support vector regression for censored data (SVRc), features were selected from the three domains and used to develop a predictive model for PSA recurrence and overall survival. It will be understood that this novel 'Systems Pathology' approach has broad application in the field of personalized medicine as it relates to tumor diagnostics, patient prognostication, and as a tool for predicting response to specific therapeutics.

EXAMPLE 3

Prediction of Aggressive Disease Subsequent to Prostatectomy

Clinical and Morphometric Data

This study was undertaken to predict aggressive disease (i.e., clinical failure as demonstrated by a positive bone scan representing metastatic prostate cancer to bone) subsequent to a patient having a prostatectomy. Prior to the present invention, no accurate analytical tools existed for providing such a prediction. As described above, the systems pathology approach of the present invention has been shown to accurately predict PSA recurrence. This study demonstrates that the present invention can also be used to accurately predict distant bone metastasis after prostatectomy.

A cohort of 119 patients who underwent radical prostatectomy was studied incorporating tissue microarrays (TMAs) constructed from prostatectomy specimens. Morphometric (i.e., image analysis) studies were performed using hematoxylin and eosin (H&E) stained tissue sections, and biological determinants were assessed with immunohistochemistry (IHC) utilizing a series of biomarkers selected for their potential biological relevance for prostate cancer progression. A predictive model for clinical failure (i.e., positive bone scan) was derived from a selected set of features through supervised multivariate learning. Patients with complete non-missing data (n=116) in each domain were evaluated with a support vector machine for regression developed to handle censored data (SVRc). Predictive performance of the model was estimated using the concordance index (CI) with generated scores used to define risk groups.

From the 116 patients, a subset of 61 patients was selected based on their clinical features, including 20 individuals with clinical failure as identified by bone metastasis. This cohort was used to create a model for predicting the likelihood of a positive bone scan within 5 years of prostatectomy. The seven features shown in FIG. 13 (including four clinical and three morphometric features) were selected which predicted clinical failure with 89 percent accuracy and a sensitivity and specificity of 86 and 85 percent, respectively. The selected morphometric features were related to the pathological objects of cytoplasm and lumen. More particularly, the selected morphometric features were area of cytoplasm divided by the total tissue area, area of lumen divided by total tissue area, and cytoplasm standard deviation of mean red channel. The clinical features are listed below.

Clinical Features
1. Extracapsular Extension (ECE)
2. Seminal Vesicle Invasion (SVI)
3. Dominant Prostatectomy Gleason Grade (PGG1)
4. Lymph Node Invasion (LNI)

Conclusion

The integration of clinical features with morphometric features resulted in the first, accurate prognostic test for predicting clinical failure within 5 years after prostatectomy. As described, the test can predict with 89% accuracy which patients are most likely to have a clinical failure (and when) within a 5 year period post prostatectomy. The results of adding molecular features to the clinical and morphometric features of the model are currently pending.

EXAMPLE 4

Liver Toxicology

Morphometric Data

This study was undertaken to demonstrate image analysis and statistical modeling capabilities in the area of toxicology. Specifically, the study called for the acquisition and analysis of sections of rat liver with the overall objective being to classify the sections as normal or abnormal. Being able to automate this process while simultaneously achieving a high-level of classification accuracy could allow for the creation of a high-throughput platform used to objectively screen for toxicities in pre-clinical studies.

The study was divided into two phases. The initial phase used a set of 100 rat liver sections as a training set; 80 normal liver sections and 20 abnormal. This set of sections was used to develop an image analysis application using the tissue image analysis system described above as well as perform feature and model selection to classify the sections. The established image analysis process was then applied to an unlabeled set of 100 rat liver sections in the second phase of the study in which the statistical models designed in the training phase were tested.

Segmentation Accuracy

The global segmentation accuracy for all objects, as measured by a pathologist's assessment, was 80%-90%.

Statistics

The statistical component of the study involved two steps. The first step involved selecting features from the imaging data generated by the image analysis of the sections. Reducing the number of features used for classification may improve the robustness and reliability of the classification of the sections. The second step involved both training a model using the selected feature set and labels for each section (abnormal, normal) and then testing the model by predicting the classification of an independent set of rat liver sections where the labels were unknown.

Feature Selection

The statistical measurements generated for each of the above objects were:
  Number of objects
  Relative area (percent, in relation to total area of image)
  Minimum size (in pixels)
  Maximum size (in pixels)
  Average size (in pixels)
  Standard deviation of the size Since multiples images which were analyzed per section, these measures were themselves averaged across all images for an individual rat liver section. The total number of original features was 378.

Feature selection also involved two steps. The first step utilized domain expertise. A pathologist selected features from the original feature list generated by the image analysis of the sections. The decision to include or exclude features was based on the understanding of the pathology of the liver and potential abnormalities/toxicities that could be encountered. From the original set of 378 features, 90 features were selected using domain knowledge.

These features were then examined using stepwise discriminant analysis to further reduce the number of features for classification. The set of features that made up each class were assumed to be multivariate normal with a common covariance matrix. Features were chosen to enter or leave the model according to the significance level of an F-test from an analysis of covariance, where the features already chosen act as the covariates and the feature under consideration is the dependent variable. A significance level of 0.15 was used.

Stepwise selection began with no features in the model. At each step, the model was examined.

If the feature in the model that contributed least to the discriminatory power of the model as measured by Wilks' lambda (the likelihood criterion) failed to meet the criterion to stay, then that feature was removed.

Otherwise, the feature not in the model that contributed most to the discriminatory power of the model was entered.

When all features in the model met the criterion to stay and none of the other features met the criterion to enter, the stepwise selection process stopped.

Classification/Model Training

The selected features were then entered into a linear discriminant analysis (LDA) which classified each of the liver sections as abnormal or normal. The output of the model was corrected for potential bias via cross-validation.

Neural networks were also explored as a classifier. The selected features were used as the inputs to the neural network model, which is a standard multilayer perceptron (MLP) structure with zero hidden units and direct connection between the input and output layers. The model was trained by trying to directly maximize an approximation to the area under the ROC curve, which is explained below. It was found that the MLP model trained by this criterion achieves better accuracy than an MLP model trained by the typical criteria, e.g., mean square error and cross entropy.

The output from both models were used to create a receiver operating characteristic (ROC) curve by choosing a different value of the model output as a cut point, calculating the sensitivity and specificity for each cut point, and plotting these in a 2-dimensional plot (sensitivity along the y-axis and specificity along the x-axis). The area under the ROC curve (AUC) uses both measures to assess each model's accuracy and can be interpreted as the ability of the model to correctly classify the liver sections as abnormal or normal. Typically, sensitivity and specificity are described in terms of the true positive rate and true negative rate, respectively. Thus in the context of this study, the abnormal class was considered as a 'positive' result, while the normal class was considered as a 'negative' result. Sensitivity, therefore, is the true positive rate, i.e. the proportion of liver sections correctly classified as abnormal; the specificity, on the other hand, is the true negative rate, i.e., the proportion of liver sections correctly classified as normal.

From the ROC curves, selected sensitivities and specificities from the training set are provided in the Results section below.

Model Testing

Once developed, the parameters of both the linear discriminant function and the neural network were locked. Upon receipt of the statistical measurements from the test set of rat liver images, both classifiers were applied using an individual cut point estimated using the cross validation results of each of the model outputs respectively. The cut points both corresponded to a sensitivity of 100% and a specificity of 90% (both based on cross validation) for a future industrial-grade application. For the initial evaluation of this external validation set of livers, assessment of the models' accuracies was performed by another party who was unblinded to the true classification of the liver sections. This other party then also provided the test key to verify the results.

Results

The area under the ROC curve for both models is very close to 1, indicating almost perfect discrimination between abnormal and normal liver sections. The function derived using LDA has an AUC of 0.99; the function derived using neural networks has an AUC of 0.98.

Also observed in the ROC curves was the sensitivity and specificity of each model, depending on the cut point applied to the model outputs to classify a liver section as abnormal or normal. Table 10 summarizes a selection of sensitivity-specificity pairs.

TABLE 10

| LDA | | NN | |
|---|---|---|---|
| Specificity | Sensitivity | Specificity | Sensitivity |
| 100% | 65% | 100% | 65% |
| 99% | 75% | 99% | 70% |
| 98% | 100% | 98% | 85% |

Testing

The test key labels were compared with the predicted classifications of the linear discriminant function and those of the neural networks. Based on the key, the results are summarized in Tables 11a and 11b as follows:

TABLE 11a

| | | Test Key Label | |
|---|---|---|---|
| | | Abnormal | Normal |
| LDA Label | Abnormal | 42 (TP) | 19 (FP) |
| | Normal | 7 (FN) | 32 (TN) |
| | | 49 | 51  100 |

Sensitivity = TP/(TP + FN) × 100 = 42/(42 + 7) × 100 = (42/49) × 100 = 86%
Specificity = TN/(FP + TN) × 100 = 32/(19 + 32) × 100 = (32/51) × 100 = 63%

TABLE 11b

| | | Test Key Label | |
|---|---|---|---|
| | | Abnormal | Normal |
| NN Label | Abnormal | 36 (TP) | 19 (FP) |
| | Normal | 13 (FN) | 32 (TN) |
| | | 49 | 51  100 |

Sensitivity = TP/(TP + FN) × 100 = 36/(36 + 13) × 100 = (36/49) × 100 = 73%
Specificity = TN/(FP + TN) × 100 = 32/(19 + 32) × 100 = (32/51) × 100 = 63%

The cut point used for the LDA classifier equaled 0.0031; the cut point used for the NN classifier equaled 0.0002. Both correspond to the system requirements of 100% sensitivity and 90% specificity.

Discussion

Based on the sensitivity and specificity of each classifier after applying them to the test set, LDA outperformed NN. The LDA classifier achieved a sensitivity of 86% which means that this classifier correctly labeled the abnormal rat liver sections as abnormal 86% of the time, as opposed to the neural network classifier which achieved a sensitivity of 73%. Specificity for both classifiers was 63%. Both the sensitivity and the specificity of each model are lower than previously observed, but this is not surprising as generalizing any classifier to an external set often leads to a drop in its accuracy. This study demonstrated the successful application of technologies for imaging and statistical modeling.

EXAMPLE 5

Prediction of Prostate Cancer Recurrence

Clinical, Morphometric, and Molecular Data

Another study was performed to generate a model that predicts time to recurrence of prostate cancer in patients who have undergone radical prostatectomy. As with Example 2, time to recurrence was defined as the time (in months) from radical prostatectomy until PSA (biochemical) recurrence. The sections of prostate tissue used in this study were composed predominantly of tumor but also included benign elements.

This study was based on information for the same 17 clinical features (Table 4) and 43 molecular features (Table 6) evaluated in Example 2. The set of 496 morphometric features (Table 1) were reduced to the 38 features shown in Table 10 (appended hereto) based on, for example, expert knowledge and additional experimentation in the field of prostate cancer recurrence. Clinical, molecular, and morphometric information for 262 patients from the 539 patient cohort described above in connection with Example 2 were evaluated in this study. Other than the filtering that reduced the number of morphometric features from 496 to 38, the main difference between this study and Example 2 is that this study used a SVRc Feature Reduction method for feature selection. SVRc Feature Reduction is described in commonly-owned U.S. patent application Ser. No. 11/438,789, filed May 22, 2006, which is hereby incorporated by reference herein in its entirety.

Results

A final model based on 6 features (3 clinical-pathological, 1 molecular, and 2 morphometric) and having a concordance index (CI) of 0.83 was generated as a result of the study. The 6 features included in the model are shown in FIG. 14, along with their respective feature contributions to the final model. The three clinical features selected as being predictive of PSA recurrence were seminal vesicle involvement (feature contribution=−5.2103), surgical margin involvement (−7.3159), and lymph node involvement (−9.3742). The one molecular feature selected was the Androgen Receptor (AR) Staining Index present in tumor (−3.5404). These clinical and molecular features are described above in connection with Example 2. The two morphometric features selected were the area occupied by epithelial cell nuclei divided by total tissue area (3.2975) and the area occupied by stroma divided by total tissue area (−0.34225). For example, total tissue area may include the sum (in pixels with 1920000 being the maximum where the image size is 1200×1600 pixels) of the areas of cytoplasm, epithelial nuclei, lumen, red blood cells, stromal nuclei, stroma, and artifacts. Possible reasons for the selection of morphometric features related to epithelial nuclei and stromal cells are also described below in connection with the validation study.

The final training model had a sensitivity of 82% and specificity of 81% for correctly predicting prostate cancer recurrence prior to 5 years. The resulting output of the SVRc model can also be interpreted as a relative risk estimate of PSA recurrence for an individual patient. Using the quartiles of this score (<25%, >25%-75%, >75%), risk groups of patients were created, and Kaplan Meier estimates of recurrence for each risk group were generated. The groups showed a statistically significant difference in time to PSA recurrence (log-rank test, p-value<0.0001).

Validation Study

The final model was validated with an external cohort consisting of 61 patients. The final model produced a CI of 0.80, sensitivity of 91% and specificity of 70% for the validation for identifying patients at risk for experiencing prostate cancer recurrence within the first 5 years.

To further understand the significance of the two morphometric features selected in the final model, Kaplan-Meier curves were generated for each morphometric feature. It was observed that increasing amounts of stroma (p=0.004) and epithelial nuclei (although not statistically significant, p=0.28) were independently associated with a favorable outcome. This raised the possibility that the quantitative measurements derived from these image patterns may represent more objective determinants of the Gleason grading system.

This study demonstrated that only a limited set of clinical, molecular, and morphometric features may be required to create a clinically useful predictive test. This reduction of features was accomplished while also retaining the predictive accuracy of the model.

EXAMPLE 6

Prediction of Prostate Cancer Recurrence

Clinical, Morphometric, and Molecular Data

Yet another study was performed to generate a model that predicts time to recurrence of prostate cancer in patients who have undergone radical prostatectomy. As in Examples 2 and 6, time to recurrence was defined as the time (in months) from radical prostatectomy until PSA (biochemical) recurrence. The sections of prostate tissue used in this study were composed predominantly of tumor but also included benign elements.

This study was based on information for the same 17 clinical features (Table 4) and 43 molecular features (Table 6) evaluated in Examples 2 and 5. The set of 496 morphometric features (Table 1) were reduced to the 33 features shown in Table 11 (appended hereto). Clinical, molecular, and morphometric information for the same 262 patients from Example 5 were evaluated in this study. This study used the same SVRc Feature Reduction method referenced above in Example 5.

Results

A final model based on 8 features (the same 6 features selected in Example 5 plus 1 additional clinical-pathological feature and 1 additional morphometric feature) and having a concordance index (CI) of 0.86 was generated as a result of the study. The 8 features included in the model are shown in FIG. 15, along with their respective feature contributions to the final model. The additional clinical feature selected in this study was biopsy Gleason Score (−10.60), described above in connection with Example 2. The additional morphometric feature selected in this study was the variation in texture within stroma as expressed in the red channel (−11.26). This feature, which indicates variation in stromal texture based on its staining properties, most likely reflects the biochemical attributes of stroma associated with tumor as opposed to benign elements.

Validation Study

The final model was validated with an external cohort consisting of 366 patients. The final model produced for the validation a CI of 0.82, sensitivity of 96% and specificity of 72% for identifying patients at risk for experiencing prostate cancer recurrence within the first 5 years. Table 12 below shows the observed clinical features for the training and validation cohorts. Tables 13a-c show the observed biomarker-molecular features from the training cohort.

TABLE 12

| Characteristic | Training | Validation |
|---|---|---|
| N | 262 | 61 |
| Age (years) | | |
| Mean | 62 | 61 |
| Median | 63 | 62 |
| Range | 38-81 | 42-74 |
| Race | | |
| Caucasian | 235 (89.7%) | 58 (95.1%) |
| African-American (Hispanic and Non-Hispanic) | 21 (8.0%) | 2 (3.3%) |
| Other/Unknown | 6 (2.3%) | 1 (1.6% |
| Pre-operative PSA (ng/mL) | | |
| Mean | 10.7 | 12.9 |
| Median | 7.8 | 10.0 |
| Range | 0.9-81.9 | 2.0-69.5 |
| Pathologic TNM Stage | | |
| T2N0 | 158 (60.3%) | Not Collected |
| T3aN0 | 70 (26.7%) | Not Collected |
| T3bN0 | 17 (6.5%) | Not Collected |
| T1-3N+ | 17 (6.5%) | Not Collected |
| Missing | 0 | Not Collected |
| UICC Stage | | |
| T1a <5% | 1 (0.4%) | Not Collected |
| T1b ≧5% | 1 (0.4%) | Not Collected |
| T1c not palpable or visible | 113 (43.1%) | Not Collected |
| T2a ≦½ lobe | 54 (20.7%) | Not Collected |
| T2b ≦1 lobe | 43 (16.4%) | Not Collected |
| T2c both lobes | 33 (12.6%) | Not Collected |
| T3a unilateral ECE | 15 (5.7%) | Not Collected |
| T3c SV+ | 2 (0.8%) | Not Collected |
| Missing | 0 | Not Collected |
| Digital Rectal Exam Result | | |
| Non-palpable | 122 (46.6%) | 32 (52.5%) |
| Palpable | 140 (53.4%) | 29 (47.5%) |
| Missing | 0 | 0 |
| Lymph Node Involvement | | |
| Negative | 246 (93.9%) | 56 (91.8%) |
| Positive | 16 (6.1%) | 5 (8.2%) |
| Missing | 0 | 0 |
| Seminal Vesicle Involvement | | |
| No | 233 (88.9%) | 51 (83.6%) |
| Yes | 29 (11.1%) | 10 (16.4%) |
| Missing | 0 | 0 |

TABLE 12-continued

| Characteristic | Training | Validation |
|---|---|---|
| Surgical Margins | | |
| Negative | 216 (82.4%) | 36 (59.0%) |
| Positive | 46 (17.6%) | 25 (41.0%) |
| Extracapsular Involvement | | |
| No | 159 (60.7%) | 43 (70.5%) |
| Yes | 103 (39.3%) | 18 (29.5%) |
| Missing | 0 | 0 |
| Dominant Biopsy Gleason Grade | | |
| 1 | 1 (0.4%) | 0 (0.0%) |
| 2 | 43 (16.4%) | 0 (0.0%) |
| 3 | 181 (69.1%) | 39 (63.9%) |
| 4 | 36 (13.7%) | 22 (36.1%) |
| 5 | 1 (0.4%) | 0 (0.0%) |
| Missing | 0 | 0 |
| Biopsy Gleason Score | | |
| 2 | 1 (0.4%) | 0 (0.0%) |
| 3 | 0 (0.0%) | 0 (0.0%) |
| 4 | 7 (2.7%) | 0 (0.0%) |
| 5 | 56 (21.4%) | 3 (4.9%) |
| 6 | 97 (37.0%) | 27 (44.3%) |
| 7 | 85 (32.4%) | 20 (32.8%) |
| 8 | 13 (5.0%) | 8 (13.1%) |
| 9 | 3 (1.2%) | 3 (4.9%) |
| Missing | 0 | 0 |
| Dominant Specimen Gleason Grade | | |
| 2 | 20 (7.6%) | 0 (0.0%) |
| 3 | 198 (75.6%) | 34 (55.7%) |
| 4 | 44 (16.8%) | 23 (37.7%) |
| 5 | 0 (0.0%) | 4 (6.6%) |
| Specimen Gleason Score | | |
| 5 | 21 (8.0%) | 1 (1.6%) |
| 6 | 86 (32.8%) | 8 (13.1%) |
| 7 | 144 (55.0%) | 37 (60.7%) |
| 8 | 11 (4.2%) | 7 (11.5%) |
| 9 | 0 (0.0%) | 8 (13.1%) |
| Ploidy | | |
| Diploid | 141 (53.8%) | Not Collected |
| Tetraploid | 113 (43.1%) | Not Collected |
| Aneuploid | 8 (3.1%) | Not Collected |
| Missing | 0 (0.0%) | Not Collected |
| Percent Ploidy in S Phase (%) | | |
| Mean | 2.4 | Not Collected |
| Median | 1.2 | Not Collected |
| Range | 0.0-66.4 | Not Collected |
| Percent Ploidy Fraction | | |
| Mean | 3.4 | Not Collected |
| Median | 2.4 | Not Collected |
| Range | 0.0-20.0 | Not Collected |

TABLE 13a

Percentage of Cells Staining, by Histologic Component and Staining Intensity (Training Set)

| | Tumor | | | PIN | | | Atrphic Gland | | |
|---|---|---|---|---|---|---|---|---|---|
| Marker | 1+ | 2+ | 3+ | 1+ | 2+ | 3+ | 1+ | 2+ | 3+ |
| Ki-67 | | | | | | | | | |
| Mean ± SD | 22.0 ± 30.4 | 7.2 ± 17.1 | 1.8 ± 4.0 | 23.0 ± 31.5 | 7.8 ± 18.3 | 2.0 ± 4.5 | 1.3 ± 8.05 | 1.2 ± 9.9 | 0.3 ± 1.6 |
| Median | 0.7 | 0.0 | 0.0 | 1.0 | 0.0 | 0.0 | 0.0 | 0.0 | 0.0 |
| Range | 0.0-100.0 | 0.0-100.0 | 0.0-26.3 | 0.0-100.0 | 0.0-100.0 | 0.0-39.5 | 0.0-96.0 | 0.0-96.5 | 0.0-13.0 |

TABLE 13a-continued

Percentage of Cells Staining, by Histologic Component and Staining Intensity (Training Set)

| | Tumor | | | PIN | | | Atrphic Gland | | |
|---|---|---|---|---|---|---|---|---|---|
| Marker | 1+ | 2+ | 3+ | 1+ | 2+ | 3+ | 1+ | 2+ | 3+ |
| CK18 | | | | | | | | | |
| Mean ± SD | NA | NA | 100.0 ± 0.04 | NA | NA | 100.0 ± 0.04 | NA | NA | 100.0 ± 0.00 |
| Median | NA | NA | 100.0 | NA | NA | 100.0 | NA | NA | 100.0 |
| Range | NA | NA | 50.0-100.0 | NA | NA | 50.0-100.0 | NA | NA | 100.0-100.0 |
| CD45 | | | | | | | | | |
| Mean ± SD | NA | NA | 0.0 ± 0.04 | NA | NA | 0.0 ± 0.01 | NA | NA | 0.0 ± 0.00 |
| Median | NA | NA | 0.0 | NA | NA | 0.0 | NA | NA | 0.0 |
| Range | NA | NA | 0.0-0.4 | NA | NA | 0.0-0.1 | NA | NA | 0.0-0.0 |
| CD68 | | | | | | | | | |
| Mean ± SD | NA | NA | 0.0 ± 0.01 | NA | NA | NA | NA | NA | NA |
| Median | NA | NA | 0.0 | NA | NA | NA | NA | NA | NA |
| Range | NA | NA | 0.0-0.1 | NA | NA | NA | NA | NA | NA |

TABLE 13b

Percentage of Cells with CD34 Staining, by Histologic Component (Training)

| | PIN | Stroma | Tumor | Tumor/PIN | Tumor/Stroma | PIN/Stroma |
|---|---|---|---|---|---|---|
| Mean ± SD | 0.0 ± 0.04 | 0.0 ± 0.11 | 0.1 ± 0.18 | 0.0 ± 0.07 | 0.0 ± 0.08 | 0.0 ± 0.04 |
| Median | 0.0 | 0.0 | 0.0 | 0.0 | 0.0 | 0.0 |
| Range | 0.0-0.4 | 0.0-1.7 | 0.0-0.9 | 0.0-0.5 | 0.0-0.4 | 0.0-0.3 |

TABLE 13c

Staining Index by Histologic Component (Training Set)

| Marker | Tumor | PIN | Gland |
|---|---|---|---|
| AR | | | |
| Mean ± SD | 171.8 ± 75.9 | 79.9 ± 83.3 | 29.5 ± 67.9 |
| Median | 200 | 66.0 | 0 |
| Range | 0-300 | 0-300 | 0-300 |
| CK14 | | | |
| Mean ± SD | 2.2 ± 6.4 | 35.2 ± 62.0 | 8.3 ± 32.6 |
| Median | 0 | 0 | 0 |
| Range | 0-69 | 0-300 | 0-300 |
| Cyclin D1 | | | |
| Mean ± SD | 1.4 ± 7.1 | 0.0 ± 0.21 | 0.0 ± 0.0 |
| Median | 0 | 0 | 0 |
| Range | 0-90 | 0-3 | 0-0 |
| PSA | | | |
| Mean ± SD | 117.9 ± 71.2 | 140.5 ± 97.4 | 22.4 ± 54.9 |
| Median | 100 | 134 | 0 |
| Range | 0-300 | 0-300 | 0-300 |
| PSMA | | | |
| Mean ± SD | 0.3 ± 2.1 | 5.8 ± 19.8 | 3.0 ± 23.2 |
| Median | 0 | 0 | 0 |
| Range | 0-21 | 0-154 | 0-300 |
| $p27^{Kip1}$ | | | |
| Mean ± SD | 3.9 ± 8.2 | 6.6 ± 19.0 | 1.3 ± 8.7 |
| Median | 0 | 0 | 0 |
| Range | 0-48 | 0-140 | 0-120 |
| Her-2/neu | | | |
| Mean ± SD | 3.5 ± 16.9 | 0.2 ± 1.1 | 0.0 ± 0.0 |
| Median | 0 | 0 | 0 |
| Range | 0-150 | 0-10 | 0-0 |

EXAMPLE 7

Prediction of Clinical Failure Subsequent to Radical Prostatectomy

Clinical, Morphometric, and Molecular Data

This study generated a model for predicting clinical failure in prostate cancer patients who have undergone radical prostatectomy. In this study, clinical failure was defined as the development of metastatic disease and/or androgen-independent disease (e.g., bone scan positive for metastases or a PSA rise while on ADT after surgery). This is in contrast to the clinical failure study described in Example 2, in which clinical failure was defined as death due to any cause.

Clinical information and morphometric information for 345 patients were evaluated in this study. Ten (10) clinical features and 27 morphometric features similar to the clinical and morphometric features shown in Tables 4 and 6 were evaluated. Eleven (11) molecular features were also evaluated. However, these molecular features were generated by a computer from images of tissue subject to immunofluorescence (IF) detection, and not based on IHC as with the molecular features described in Example 2.

More particularly, Alexa fluorochrome labeled antibodies for the androgen receptor (AR), racemase (AMACR), cytokeratin 18 (CK18), TP73L (p63), and high molecular weight keratin were used, along with DAPI, in a 'quint-plex' assay. Based on the distinctive spectral profiles of the fluorochromes, antigen-specific gray-scale images were acquired. Scripts were generated for the Definiens Cellenger product to localize the individual antigens. From antigen distribution and intensity, the scripts identified cell types and cellular compartments (e.g. luminal epithelial cells, epithelial/stromal nuclei) and quantified AR and AMACR in prostate tumor, benign glands, and stroma. Namely, scripts for the Definiens Cellenger product were generated that segmented DAPI and CK18 images into valid nuclei and cytoplasm objects, respectively. These scripts classified an image object as either nuclei or cytoplasm based on an intensity threshold, where the intensity threshold was a linear function of the biomarker gray scale image characteristics (e.g., average intensity, standard deviation, quantiles). Each script/linear function was specific to a given biomarker and was designed using supervised learning (threshold settings by an expert) and linear regression between expert thresholds and image characteristics. The identified cytoplasm objects served as anchor objects for the nuclei split into epithelial and stromal objects. AR and AMACR biomarkers were also segmented using spatial and intensity co-localizations. The spatial localization identified a biomarker within specified compartment: epithelial and stromal nuclei for the AR and epithelial cells (cytoplasm) for the AMACR. The threshold function similar to those used for DAPI and CK18 allowed further classification of the biomarker signal within a compartment as either valid or noise. Patients were excluded if their cores were missing from the array or if the sample contained only stroma.

Because the majority of patients had multiple cores from which IF features were extracted, a procedure was devised for aggregating the feature values across multiple cores, for each patient and feature. Four candidate functions (min, max, median, and mean) were considered (e.g., if a patient had 3 cores, the function min returns the lowest value among the 3 cores). For a given feature, each of these functions was applied to aggregate the core values of each patient in the training set; then the concordance index for each aggregation function was calculated to evaluate it as a predictor of clinical failure. The best aggregating function for a feature was considered to be the one whose concordance index was farthest from random (0.5). Table 14 below lists the 11 IF features and the corresponding selected aggregating functions, and Table 15 describes the features. The aggregating function selected was then used to generate a single value for each IF feature for each patient. Additional details regarding multiplex immunofluorescence are described in commonly-owned U.S. patent application Ser. No. 11/581,083, titled "Multiplex In Situ Immunohistochemical Analysis", filed Oct. 13, 2006, which is hereby incorporated by reference herein in its entirety.

TABLE 14

| IF feature | Selected aggregating function |
| --- | --- |
| EpitarposamaMeanMeanChannel30017 | mean |
| EpitarposamaMeanMeanChannel30021 | median |
| Mamacrpostotalarea0045 | max |
| Mcytoplasmamacrpostotalarea0050 | max |
| SumMen02_10totalarea | not applicable; this is a derived feature whose value is the average of the aggregated values of 10 primary features |
| Mepithnucleiarposamacrpostot0085 | max |
| RelAEpithNucARpos | median |
| RelAEpithNucARposAMACRpos | max |
| MeanEpithNucARPosIntensity | min |
| MeanEpithNucARPosAMACRPosIntens | max |
| NormSimpleAverageTotalEpithLum | min |

TABLE 15

| Feature | Description |
| --- | --- |
| EpitarposamaMeanMeanChannel30017 | Mean intensity of the DAPI objects classified as Epithelial Nuclei positively expressed with AR biomarker and located in the cytoplasm negative with respect to the AMACR biomarker |
| EpitarposamaMeanMeanChannel30021 | Mean intensity of the DAPI objects classified as Epithelial Nuclei negatively expressed with AR biomarker and located in the cytoplasm positive with respect to the AMACR biomarker |
| Mamacrpostotalarea0045 | Total area of the AMACR objects with the intensity above noise/signal threshold |
| Mcytoplasmamacrpostotalarea0050 | Total area of the cytoplasm (CK18) objects positively expressed with AMACR |
| SumMen02_10totalarea | In every DAPI object classified as an epithelial nucleus and positively expressed with AR biomarker the sum of normalized AR object intensity values $\tilde{Y}_k$ is calculated: $$I = \sum_k \tilde{Y}_k \text{ Where } \tilde{Y}_k = Y_k/Y_*$$ is ratio of the actual AR object intensity $Y_k$ and the local (with respect to an AR image) noise vs. signal intensity threshold $Y_*$ values. The I values are associated with total amount of the protein detected by the biomarker. The values of I are subject for binning. The epithelial nuclei are classified into M = 11 bins. Every bin characterizes a certain amount of the AR in the epithelial nuclei. The feature is area of the epithelial nuclei with $20 \leq I < 30$. The area values are divided on to total area of the epithelial nuclei detected on the image |
| Mepithnucleiarposamacrpostot0085 | Total area of the epithelial nuclei positively expressed with AR and positive with respect to the AMACR |
| RelAEpithNucARpos | Relative area of the epithelial nuclei with AR+ with respect to the total epithelial nuclei area |
| RelAEpithNucARposAMACRpos | Fraction (relative area) of the AR+ epithelial nuclei with AMACR+ with respect to the AR+ epithelial nuclei |
| MeanEpithNucARPosIntensity | Value of the summed intensity (I values) for the AR objects in epithelial nuclei calculated as average across I bin values. The feature can be interpreted as average amount of the AR expressed in the epithelial nuclei in an image (region of interest) |
| MeanEpithNucARPosAMACRPosIntens | Value of the summed intensity (I values) for the AR objects in the AR+ and AMACR+ epithelial nuclei estimated through mean value of the intensity. The feature is proportional to the average amount of the AR expressed in the epithelial nuclei located |

TABLE 15-continued

| Feature | Description |
|---|---|
| | in the cytoplasm positive with respect to the AMACR marker. |
| NormSimpleAverageTotalEpithLum | Concept of luminance - total light energy emitted by object - was introduced. For every DAPI objects classified as an epithelial nucleus luminance was calculated (mean AR intensity multiplied on object area). The feature is an estimate of the AR amount in the epithelial nuclei calculated via luminance values. |

All the IF features except 'Nuclear AR present within epithelial cells that are AMACR negative' displayed association with clinical failure in univariate analysis based on concordance index ($CI \leq 0.4$ or $CI \geq 0.6$). Table 15 below describes various

Results

The model resulting from this study was based on 7 features (3 clinical, 1 molecular, and 3 morphometric) and had a concordance index (CI) of 0.91, sensitivity of 95%, and a specificity of 80% on the training cohort. The 7 features included in the model are shown in FIG. 16. The 3 clinical features selected as being predictive of clinical failure post-prostatectomy were Biopsy Gleason Score, Lymph Node Involvement, and Specimen (Prostatectomy) Gleason Score. The 3 morphometric features were mean intensity of epithelial cytoplasm as expressed in the blue channel (CytoplasmMeanMeanChannel60060), variation in texture within the stroma as expressed in the Red channel (StromaMeanStddevChannel40310), and variation in texture between epithelial nuclei as expressed in the Red channel (EpitheNucleiStddevMeanChann40157). As described above, the feature related to stromal texture is based on its staining properties and most likely reflects the biochemical attributes of stroma associated with tumor as opposed to benign elements. Additionally, typically when the cytoplasm color changes from light blue to dark blue it reflects changes in the tissue due to cancer development, namely epithelial cell invasion into stroma areas. Regarding texture variations inside epithelial nuclei (folded/unfolded chromatin texture and nucleoli), cancer development is typically characterized by an increased number of the epithelial nuclei with unfolded chromatin texture as well as an increased number of nucleoli, which results in higher values for this feature. The 1 molecular feature selected was AR intensity within epithelial cells that were AMACR positive.

Validation

The final model was validated with an independent cohort consisting of 319 patients. The final model produced for the validation a CI of 0.85, sensitivity of 89% and specificity of 77% for predicting clinical failure after prostatectomy. Table 16 below shows the observed clinical features for the training and validation cohorts.

TABLE 16

| Characteristic | Training | Validation |
|---|---|---|
| Clinical Information | | |
| Race | | |
| White (Hispanic and Non-Hispanic) | 328 (95.1) | 301 (94.4) |
| African-American (Hispanic and Non-Hispanic) | 11 (3.2) | 9 (2.8) |
| Other/Unknown | 6 (1.7) | 9 (2.8) |
| Pre-operative PSA (ng/ml) | | |
| Mean | 11.4 | 11.1 |
| Median | 7.9 | 8.2 |
| Range | 0.5-100.0 | 1.1-56.2 |
| Clinical TNM Stage | | |
| T1a/b | 4 (1.2) | 4 (1.3) |
| T1c | 172 (49.9) | 148 (46.4) |
| T2a | 64 (18.6) | 59 (18.5) |
| T2b | 29 (8.4) | 26 (8.2) |
| T2c | 67 (19.4) | 77 (24.1) |
| T3 | 9 (2.6) | 5 (1.6) |
| Lymph Node Involvement | | |
| Negative | 332 (96.2) | 308 (96.6) |
| Positive | 13 (3.8) | 11 (3.4) |
| Seminal Vesicle Involvement | | |
| No | 316 (91.6) | 291 (91.2) |
| Yes | 29 (8.4) | 28 (8.8) |
| Surgical Margins | | |
| Negative | 228 (66.1) | 199 (62.4) |
| Positive | 117 (33.9) | 120 (37.6) |
| Extracapsular Involvement | | |
| No | 242 (70.1) | 222 (69.6) |
| Yes | 103 (29.9) | 97 (30.4) |
| Dominant Biopsy Gleason Grade | | |
| 1 | 2 (0.6) | 1 (0.3) |
| 2 | 22 (6.4) | 20 (6.3) |
| 3 | 264 (76.5) | 247 (77.4) |
| 4 | 56 (19.4) | 51 (16.0) |
| 5 | 9 (2.6) | 0 (0.0) |
| Biopsy Gleason Score | | |
| 2 | 1 (0.3) | 0 (0.0) |
| 3 | 2 (0.6) | 1 (0.3) |
| 4 | 7 (2.0) | 12 (3.8) |
| 5 | 28 (8.1) | 27 (8.5) |
| 6 | 186 (53.9) | 159 (49.8) |
| 7 | 93 (27.0) | 97 (30.4) |
| 8 | 23 (6.7) | 20 (6.3) |
| 9 | 5 (1.5) | 3 (0.9) |
| 10 | 0 (0.0) | 0 (0.0) |
| Dominant Specimen Gleason Grade | | |
| 2 | 9 (2.6) | 8 (2.5) |
| 3 | 269 (78.0) | 243 (76.2) |
| 4 | 62 (18.0) | 63 (19.8) |
| 5 | 5 (1.5) | 5 (1.6) |
| Specimen Gleason Score | | |
| 5 | 16 (4.6) | 16 (5.0) |
| 6 | 112 (32.5) | 102 (32.0) |
| 7 | 182 (52.8) | 167 (52.4) |
| 8 | 22 (6.4) | 18 (5.6) |
| 9 | 12 (3.5) | 16 (5.0) |
| 10 | 1 (0.3) | 0 (0.0) |

In another aspect, based on an evaluation of a subset of patients who were treated with ADT post-prostatectomy, it has been determined that increasing levels of AR may be associated with a shortened time to clinical failure post treatment with ADT. Thus, measurement(s) of AR content in the prostatectomy specimen could be used to predict response to an androgen suppression type of therapy. To summarize, AR content at the time of the prostatectomy specimen and prior to any form of treatment may be used to t only progression of disease but also potentially response to treatment.

Additional Embodiments

Thus it is seen that methods and systems are provided for predicting the occurrence of a medical condition. Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, unclaimed inventions are also contemplated. Applicants reserve the right to pursue such inventions in later claims.

Insofar as embodiments of the invention described above are implementable, at least in part, using a computer system, it will be appreciated that a computer program for implementing at least part of the described methods and/or the described systems is envisaged as an aspect of the present invention. The computer system may be any suitable apparatus, system or device. For example, the computer system may be a programmable data processing apparatus, a general purpose computer, a Digital Signal Processor or a microprocessor. The computer program may be embodied as source code and undergo compilation for implementation on a computer, or may be embodied as object code, for example.

It is also conceivable that some or all of the functionality ascribed to the computer program or computer system aforementioned may be implemented in hardware, for example by means of one or more application specific integrated circuits.

Suitably, the computer program can be stored on a carrier medium in computer usable form, which is also envisaged as an aspect of the present invention. For example, the carrier medium may be solid-state memory, optical or magneto-optical memory such as a readable and/or writable disk for example a compact disk (CD) or a digital versatile disk (DVD), or magnetic memory such as disc or tape, and the computer system can utilize the program to configure it for operation. The computer program may also be supplied from a remote source embodied in a carrier medium such as an electronic signal, including a radio frequency carrier wave or an optical carrier wave.

REFERENCES

The following references referred to above are all hereby incorporated by reference herein in their entireties:

[1] Scherr D., et al., *Urology*. 61 (2 Suppl 1): 14-24, February 2003, Swindle P. W., et al., *Urologic Clinics of North America*. 30(2):377-401, May 2003.
[2] Wahlby C., et al., *Analytical Cellular Pathology* 24, 101-111, 2002.
[3] Street W. N., "Xcyt: A System for Remote Cytological Diagnosis and Prognosis of Breast Cancer," In *Soft Computing Techniques in Breast Cancer Prognosis and Diagnosis*, L. C. Jain (ed.), CRC Press, 1999
[4] Gleason D. F., "The Veteran's Administration Cooperative Urologic Research Group: Histologic Grading and Clinical Staging of Prostatic Carcinoma," In *Urologic Pathology: The Prostate*, Tannenbaum M. (ed.), 171-198, Lea and Febiger, Philadelphia, 1977.
[5] Cristianni et al., An Introduction to Support Vector Machines, Cambridge University Press (2000).
[6] Hastie, The Elements of Statistical Learning, Springer (2001).
[7] F. E. Harrell et al., "Evaluating the yield of medical tests," JAMA, 247(18):2543-2546, 1982.
[8] Bishop, C., Neural Networks for Pattern Recognition, Oxford University Press (1995).
[9] Fausett, L., Fundamentals of Neural Networks, New York, Prentice Hall (1994).
[10] Definiens Cellenger Architecture: A Technical Review, April 2004.
[11] Baatz M. and Schäpe A., "Multiresolution Segmentation—An Optimization Approach for High Quality Multiscale Image Segmentation," In *Angewandte Geographische Informationsverarbeitung* XII, Strobl, J., Blaschke, T., Griesebner, G. (eds.), Wichmann-Verlag, Heidelberg, 12-23, 2000.
[12] Fukunaga K., *Introduction to Statistical Pattern Recognition*, 2nd Edition, Boston: Academic Press, 1990.
[13] Duda R. O. et al., *Pattern Classification*, 2nd Edition, John Wiley & Sons Inc., 2001.
[14] Holmberg L. et al., A randomized trial comparing radical prostatectomy with watchful waiting in early prostate cancer, N. Engl. M. Med., 347:781-789 (2002).
[15] Pound C R et al., Natural history of progression after PSA elevation following radical prostatectomy, JAMA 1999, 281:1591-1597.
[16] Kumar-Sinha C. et al., Molecular markers to identify patients at risk for recurrence after primary treatment for prostate cancer, Urology 2003; 62 Suppl. 1:19-35.
[17] Cox D. R., "Regression Models and Life Tables," *Journal of the Royal Statistical Society*, B 34, 187-220, 1972.
[18] Harrell F. E., *Regression Modeling Strategies*, Springer-Verlag 2001.
[19] Tuxhorn et al., "Reactive Stroma in Human Prostate Cancer: Induction of Myofibroblast Phenotype and Extracellular Matrix Remodeling" Clinical Cancer Research 2912 Vol. 8, 2912-2923, September 2002.
[20] Kattan et al., "Postoperative Nomogram for Disease Recurrence After Radical Prostatectomy for Prostate Cancer," Journal of Clinical Oncology, Vol. 17, No. 5 (May), 1999: pp 1499-1507.

TABLE 1

Morphometric Features
Script v1.0 (496 Features)

| Feature |
| --- |
| Background.MaxAreaPxl |
| Background.MeanAreaPxl |
| Background.MinAreaPxl |
| Background.StdDevAreaPxl |
| Background.SumAreaPxl |
| Cytoplasm.Objects |
| Cytoplasm.ObjectsPct |
| Cytoplasm.MaxAreaPxl |
| Cytoplasm.MeanAreaPxl |
| Cytoplasm.MinAreaPxl |
| Cytoplasm.StdDevAreaPxl |
| Cytoplasm.SumAreaPxl |
| Cytoplasm.MaxAsymmetry |
| Cytoplasm.MeanAsymmetry |

TABLE 1-continued

Morphometric Features
Script v1.0 (496 Features)

Feature

Cytoplasm.MinAsymmetry
Cytoplasm.StdDevAsymmetry
Cytoplasm.MaxBorderlengthPxl
Cytoplasm.MeanBorderlengthPxl
Cytoplasm.MinBorderlengthPxl
Cytoplasm.StdDevBorderlengthPxl
Cytoplasm.SumBorderlengthPxl
Cytoplasm.MaxBrightness
Cytoplasm.MeanBrightness
Cytoplasm.MinBrightness
Cytoplasm.StdDevBrightness
Cytoplasm.MaxCompactness
Cytoplasm.MeanCompactness
Cytoplasm.MinCompactness
Cytoplasm.StdDevCompactness
Cytoplasm.MaxDensity
Cytoplasm.MeanDensity
Cytoplasm.MinDensity
Cytoplasm.StdDevDensity
Cytoplasm.MaxDiff.ofenclosing.enclo
Cytoplasm.MeanDiff.ofenclosing.encl
Cytoplasm.MinDiff.ofenclosing.enclo
Cytoplasm.StdDevDiff.ofenclosing.en
Cytoplasm.MaxEllipticFit
Cytoplasm.MeanEllipticFit
Cytoplasm.MinEllipticFit
Cytoplasm.StdDevEllipticFit
Cytoplasm.MaxLengthPxl
Cytoplasm.MeanLengthPxl
Cytoplasm.MinLengthPxl
Cytoplasm.StdDevLengthPxl
Cytoplasm.SumLengthPxl
Cytoplasm.MaxMax.Diff.
Cytoplasm.MeanMax.Diff.
Cytoplasm.MinMax.Diff.
Cytoplasm.StdDevMax.Diff.
Cytoplasm.MaxMeanChannel1
Cytoplasm.MeanMeanChannel1
Cytoplasm.MinMeanChannel1
Cytoplasm.StdDevMeanChannel1
Cytoplasm.MaxMeanChannel2
Cytoplasm.MeanMeanChannel2
Cytoplasm.MinMeanChannel2
Cytoplasm.StdDevMeanChannel2
Cytoplasm.MaxMeanChannel3
Cytoplasm.MeanMeanChannel3
Cytoplasm.MinMeanChannel3
Cytoplasm.StdDevMeanChannel3
Cytoplasm.MaxRadiusoflargestenclose
Cytoplasm.MeanRadiusoflargestenclos
Cytoplasm.MinRadiusoflargestenclose
Cytoplasm.StdDevRadiusoflargestencl
Cytoplasm.MaxRadiusofsmallestenclos
Cytoplasm.MeanRadiusofsmallestenclo
Cytoplasm.MinRadiusofsmallestenclos
Cytoplasm.StdDevRadiusofsmallestenc
Cytoplasm.MaxStdevChannel1
Cytoplasm.MeanStdevChannel1
Cytoplasm.MinStdevChannel1
Cytoplasm.StdDevStdevChannel1
Cytoplasm.MaxStdevChannel2
Cytoplasm.MeanStdevChannel2
Cytoplasm.MinStdevChannel2
Cytoplasm.StdDevStdevChannel2
Cytoplasm.MaxStdevChannel3
Cytoplasm.MeanStdevChannel3
Cytoplasm.MinStdevChannel3
Cytoplasm.StdDevStdevChannel3
Cytoplasm.MaxWidthPxl
Cytoplasm.MeanWidthPxl
Cytoplasm.MinWidthPxl
Cytoplasm.StdDevWidthPxl
Epithelial.Nuclei.Objects
Epithelial.Nuclei.ObjectsPct Epithelial.Nuclei.MaxAreaPxl
Epithelial.Nuclei.MeanAreaPxl
Epithelial.Nuclei.MinAreaPxl
Epithelial.Nuclei.StdDevAreaPxl
Epithelial.Nuclei.SumAreaPxl
Epithelial.Nuclei.MaxAsymmetry
Epithelial.Nuclei.MeanAsymmetry
Epithelial.Nuclei.MinAsymmetry
Epithelial.Nuclei.StdDevAsymmetry
Epithelial.Nuclei.MaxBorderlengthPx
Epithelial.Nuclei.MeanBorderlengthP
Epithelial.Nuclei.MinBorderlengthPx
Epithelial.Nuclei.StdDevBorderlengt
Epithelial.Nuclei.SumBorderlengthPx
Epithelial.Nuclei.MaxBrightness
Epithelial.Nuclei.MeanBrightness
Epithelial.Nuclei.MinBrightness
Epithelial.Nuclei.StdDevBrightness
Epithelial.Nuclei.MaxCompactness
Epithelial.Nuclei.MeanCompactness
Epithelial.Nuclei.MinCompactness
Epithelial.Nuclei.StdDevCompactness
Epithelial.Nuclei.MaxDensity
Epithelial.Nuclei.MeanDensity
Epithelial.Nuclei.MinDensity
Epithelial.Nuclei.StdDevDensity
Epithelial.Nuclei.MaxDiff.ofenclosi
Epithelial.Nuclei.MeanDiff.ofenclos
Epithelial.Nuclei.MinDiff.ofenclosi
Epithelial.Nuclei.StdDevDiff.ofencl
Epithelial.Nuclei.MaxEllipticFit
Epithelial.Nuclei.MeanEllipticFit
Epithelial.Nuclei.MinEllipticFit
Epithelial.Nuclei.StdDevEllipticFit
Epithelial.Nuclei.MaxLengthPxl
Epithelial.Nuclei.MeanLengthPxl
Epithelial.Nuclei.MinLengthPxl
Epithelial.Nuclei.StdDevLengthPxl
Epithelial.Nuclei.SumLengthPxl
Epithelial.Nuclei.MaxMax.Diff.
Epithelial.Nuclei.MeanMax.Diff.
Epithelial.Nuclei.MinMax.Diff.
Epithelial.Nuclei.StdDevMax.Diff.
Epithelial.Nuclei.MaxMeanChannel1
Epithelial.Nuclei.MeanMeanChannel1
Epithelial.Nuclei.MinMeanChannel1
Epithelial.Nuclei.StdDevMeanChannel
Epithelial.Nuclei.MaxMeanChannel2
Epithelial.Nuclei.MeanMeanChannel2
Epithelial.Nuclei.MinMeanChannel2
Epithelial.Nuclei.StdDevMeanChannel
Epithelial.Nuclei.MaxMeanChannel3
Epithelial.Nuclei.MeanMeanChannel3
Epithelial.Nuclei.MinMeanChannel3
Epithelial.Nuclei.StdDevMeanChannel
Epithelial.Nuclei.MaxRadiusoflarges
Epithelial.Nuclei.MeanRadiusoflarge
Epithelial.Nuclei.MinRadiusoflarges
Epithelial.Nuclei.StdDevRadiusoflar
Epithelial.Nuclei.MaxRadiusofsmalle
Epithelial.Nuclei.MeanRadiusofsmall
Epithelial.Nuclei.MinRadiusofsmalle
Epithelial.Nuclei.StdDevRadiusofsma
Epithelial.Nuclei.MaxStdevChannel1
Epithelial.Nuclei.MeanStdevChannel1
Epithelial.Nuclei.MinStdevChannel1
Epithelial.Nuclei.StdDevStdevChanne
Epithelial.Nuclei.MaxStdevChannel2
Epithelial.Nuclei.MeanStdevChannel2
Epithelial.Nuclei.MinStdevChannel2
Epithelial.Nuclei.StdDevStdevChanne
Epithelial.Nuclei.MaxStdevChannel3
Epithelial.Nuclei.MeanStdevChannel3
Epithelial.Nuclei.MinStdevChannel3

TABLE 1-continued

Morphometric Features
Script v1.0 (496 Features)

Feature

Epithelial.Nuclei.StdDevStdevChanne
Epithelial.Nuclei.MaxWidthPxl
Epithelial.Nuclei.MeanWidthPxl
Epithelial.Nuclei.MinWidthPxl
Epithelial.Nuclei.StdDevWidthPxl
Lumen.Objects
Lumen.ObjectsPct
Lumen.MaxAreaPxl
Lumen.MeanAreaPxl
Lumen.MinAreaPxl
Lumen.StdDevAreaPxl
Lumen.SumAreaPxl
Lumen.MaxAsymmetry
Lumen.MeanAsymmetry
Lumen.MinAsymmetry
Lumen.StdDevAsymmetry
Lumen.MaxBorderlengthPxl
Lumen.MeanBorderlengthPxl
Lumen.MinBorderlengthPxl
Lumen.StdDevBorderlengthPxl
Lumen.SumBorderlengthPxl
Lumen.MaxBrightness
Lumen.MeanBrightness
Lumen.MinBrightness
Lumen.StdDevBrightness
Lumen.MaxCompactness
Lumen.MeanCompactness
Lumen.MinCompactness
Lumen.StdDevCompactness
Lumen.MaxDensity
Lumen.MeanDensity
Lumen.MinDensity
Lumen.StdDevDensity
Lumen.MaxDiff.ofenclosing.enclosede
Lumen.MeanDiff.ofenclosing.enclosed
Lumen.MinDiff.ofenclosing.enclosede
Lumen.StdDevDiff.ofenclosing.enclos
Lumen.MaxEllipticFit
Lumen.MeanEllipticFit
Lumen.MinEllipticFit
Lumen.StdDevEllipticFit
Lumen.MaxLengthPxl
Lumen.MeanLengthPxl
Lumen.MinLengthPxl
Lumen.StdDevLengthPxl
Lumen.SumLengthPxl
Lumen.MaxMax.Diff.
Lumen.MeanMax.Diff.
Lumen.MinMax.Diff.
Lumen.StdDevMax.Diff.
Lumen.MaxMeanChannel1
Lumen.MeanMeanChannel1
Lumen.MinMeanChannel1
Lumen.StdDevMeanChannel1
Lumen.MaxMeanChannel2
Lumen.MeanMeanChannel2
Lumen.MinMeanChannel2
Lumen.StdDevMeanChannel2
Lumen.MaxMeanChannel3
Lumen.MeanMeanChannel3
Lumen.MinMeanChannel3
Lumen.StdDevMeanChannel3
Lumen.MaxRadiusoflargestenclosedell
Lumen.MeanRadiusoflargestenclosedel
Lumen.MinRadiusoflargestenclosedell
Lumen.StdDevRadiusoflargestenclosed
Lumen.MaxRadiusofsmallestenclosinge
Lumen.MeanRadiusofsmallestenclosing
Lumen.MinRadiusofsmallestenclosinge
Lumen.StdDevRadiusofsmallestenclosi
Lumen.MaxStdevChannel1
Lumen.MeanStdevChannel1
Lumen.MinStdevChannel1
Lumen.StdDevStdevChannel1

Lumen.MaxStdevChannel2
Lumen.MeanStdevChannel2
Lumen.MinStdevChannel2
Lumen.StdDevStdevChannel2
Lumen.MaxStdevChannel3
Lumen.MeanStdevChannel3
Lumen.MinStdevChannel3
Lumen.StdDevStdevChannel3
Lumen.MaxWidthPxl
Lumen.MeanWidthPxl
Lumen.MinWidthPxl
Lumen.StdDevWidthPxl
Red.Blood.Cell.Objects
Red.Blood.Cell.ObjectsPct
Red.Blood.Cell.MaxAreaPxl
Red.Blood.Cell.MeanAreaPxl
Red.Blood.Cell.MinAreaPxl
Red.Blood.Cell.StdDevAreaPxl
Red.Blood.Cell.SumAreaPxl
Red.Blood.Cell.MaxAsymmetry
Red.Blood.Cell.MeanAsymmetry
Red.Blood.Cell.MinAsymmetry
Red.Blood.Cell.StdDevAsymmetry
Red.Blood.Cell.MaxBorderlengthPxl
Red.Blood.Cell.MeanBorderlengthPxl
Red.Blood.Cell.MinBorderlengthPxl
Red.Blood.Cell.StdDevBorderlengthPx
Red.Blood.Cell.SumBorderlengthPxl
Red.Blood.Cell.MaxBrightness
Red.Blood.Cell.MeanBrightness
Red.Blood.Cell.MinBrightness
Red.Blood.Cell.StdDevBrightness
Red.Blood.Cell.MaxCompactness
Red.Blood.Cell.MeanCompactness
Red.Blood.Cell.MinCompactness
Red.Blood.Cell.StdDevCompactness
Red.Blood.Cell.MaxDensity
Red.Blood.Cell.MeanDensity
Red.Blood.Cell.MinDensity
Red.Blood.Cell.StdDevDensity
Red.Blood.Cell.MaxDiff.ofenclosing.
Red.Blood.Cell.MeanDiff.ofenclosing
Red.Blood.Cell.MinDiff.ofenclosing.
Red.Blood.Cell.StdDevDiff.ofenclosi
Red.Blood.Cell.MaxEllipticFit
Red.Blood.Cell.MeanEllipticFit
Red.Blood.Cell.MinEllipticFit
Red.Blood.Cell.StdDevEllipticFit
Red.Blood.Cell.MaxLengthPxl
Red.Blood.Cell.MeanLengthPxl
Red.Blood.Cell.MinLengthPxl
Red.Blood.Cell.StdDevLengthPxl
Red.Blood.Cell.SumLengthPxl
Red.Blood.Cell.MaxMax.Diff.
Red.Blood.Cell.MeanMax.Diff.
Red.Blood.Cell.MinMax.Diff.
Red.Blood.Cell.StdDevMax.Diff.
Red.Blood.Cell.MaxMeanChannel1
Red.Blood.Cell.MeanMeanChannel1
Red.Blood.Cell.MinMeanChannel1
Red.Blood.Cell.StdDevMeanChannel1
Red.Blood.Cell.MaxMeanChannel2
Red.Blood.Cell.MeanMeanChannel2
Red.Blood.Cell.MinMeanChannel2
Red.Blood.Cell.StdDevMeanChannel2
Red.Blood.Cell.MaxMeanChannel3
Red.Blood.Cell.MeanMeanChannel3
Red.Blood.Cell.MinMeanChannel3
Red.Blood.Cell.StdDevMeanChannel3
Red.Blood.Cell.MaxRadiusoflargesten
Red.Blood.Cell.MeanRadiusoflargeste
Red.Blood.Cell.MinRadiusoflargesten
Red.Blood.Cell.StdDevRadiusoflarges
Red.Blood.Cell.MaxRadiusofsmalleste TABLE 1-continued Morphometric Features
Script v1.0 (496 Features)

Feature

Red.Blood.Cell.MeanRadiusofsmallest
Red.Blood.Cell.MinRadiusofsmalleste
Red.Blood.Cell.StdDevRadiusofsmalle
Red.Blood.Cell.MaxStdevChannel1
Red.Blood.Cell.MeanStdevChannel1
Red.Blood.Cell.MinStdevChannel1
Red.Blood.Cell.StdDevStdevChannel1
Red.Blood.Cell.MaxStdevChannel2
Red.Blood.Cell.MeanStdevChannel2
Red.Blood.Cell.MinStdevChannel2
Red.Blood.Cell.StdDevStdevChannel2
Red.Blood.Cell.MaxStdevChannel3
Red.Blood.Cell.MeanStdevChannel3
Red.Blood.Cell.MinStdevChannel3
Red.Blood.Cell.StdDevStdevChannel3
Red.Blood.Cell.MaxWidthPxl
Red.Blood.Cell.MeanWidthPxl
Red.Blood.Cell.MinWidthPxl
Red.Blood.Cell.StdDevWidthPxl
Stroma.Objects
Stroma.ObjectsPct
Stroma.MaxAreaPxl
Stroma.MeanAreaPxl
Stroma.MinAreaPxl
Stroma.StdDevAreaPxl
Stroma.SumAreaPxl
Stroma.MaxAsymmetry
Stroma.MeanAsymmetry
Stroma.MinAsymmetry
Stroma.StdDevAsymmetry
Stroma.MaxBorderlengthPxl
Stroma.MeanBorderlengthPxl
Stroma.MinBorderlengthPxl
Stroma.StdDevBorderlengthPxl
Stroma.SumBorderlengthPxl
Stroma.MaxBrightness
Stroma.MeanBrightness
Stroma.MinBrightness
Stroma.StdDevBrightness
Stroma.MaxCompactness
Stroma.MeanCompactness
Stroma.MinCompactness
Stroma.StdDevCompactness
Stroma.MaxDensity
Stroma.MeanDensity
Stroma.MinDensity
Stroma.StdDevDensity
Stroma.MaxDiff.ofenclosing.enclosed
Stroma.MeanDiff.ofenclosing.enclose
Stroma.MinDiff.ofenclosing.enclosed
Stroma.StdDevDiff.ofenclosing.enclo
Stroma.MaxEllipticFit
Stroma.MeanEllipticFit
Stroma.MinEllipticFit
Stroma.StdDevEllipticFit
Stroma.MaxLengthPxl
Stroma.MeanLengthPxl
Stroma.MinLengthPxl
Stroma.StdDevLengthPxl
Stroma.SumLengthPxl
Stroma.MaxMax.Diff.
Stroma.MeanMax.Diff.
Stroma.MinMax.Diff.
Stroma.StdDevMax.Diff.
Stroma.MaxMeanChannel1
Stroma.MeanMeanChannel1
Stroma.MinMeanChannel1
Stroma.StdDevMeanChannel1
Stroma.MaxMeanChannel2
Stroma.MeanMeanChannel2
Stroma.MinMeanChannel2
Stroma.StdDevMeanChannel2
Stroma.MaxMeanChannel3
Stroma.MeanMeanChannel3

TABLE 1-continued

Morphometric Features
Script v1.0 (496 Features)

Feature

Stroma.MinMeanChannel3
Stroma.StdDevMeanChannel3
Stroma.MaxRadiusoflargestenclosedel
Stroma.MeanRadiusoflargestenclosede
Stroma.MinRadiusoflargestenclosedel
Stroma.StdDevRadiusoflargestenclose
Stroma.MaxRadiusofsmallestenclosing
Stroma.MeanRadiusofsmallestenclosin
Stroma.MinRadiusofsmallestenclosing
Stroma.StdDevRadiusofsmallestenclos
Stroma.MaxStdevChannel1
Stroma.MeanStdevChannel1
Stroma.MinStdevChannel1
Stroma.StdDevStdevChannel1
Stroma.MaxStdevChannel2
Stroma.MeanStdevChannel2
Stroma.MinStdevChannel2
Stroma.StdDevStdevChannel2
Stroma.MaxStdevChannel3
Stroma.MeanStdevChannel3
Stroma.MinStdevChannel3
Stroma.StdDevStdevChannel3
Stroma.MaxWidthPxl
Stroma.MeanWidthPxl
Stroma.MinWidthPxl
Stroma.StdDevWidthPxl
Stroma.Nuclei.Objects
Stroma.Nuclei.ObjectsPct
Stroma.Nuclei.MaxAreaPxl
Stroma.Nuclei.MeanAreaPxl
Stroma.Nuclei.MinAreaPxl
Stroma.Nuclei.StdDevAreaPxl
Stroma.Nuclei.SumAreaPxl
Stroma.Nuclei.MaxAsymmetry
Stroma.Nuclei.MeanAsymmetry
Stroma.Nuclei.MinAsymmetry
Stroma.Nuclei.StdDevAsymmetry
Stroma.Nuclei.MaxBorderlengthPxl
Stroma.Nuclei.MeanBorderlengthPxl
Stroma.Nuclei.MinBorderlengthPxl
Stroma.Nuclei.StdDevBorderlengthPxl
Stroma.Nuclei.SumBorderlengthPxl
Stroma.Nuclei.MaxBrightness
Stroma.Nuclei.MeanBrightness
Stroma.Nuclei.MinBrightness
Stroma.Nuclei.StdDevBrightness
Stroma.Nuclei.MaxCompactness
Stroma.Nuclei.MeanCompactness
Stroma.Nuclei.MinCompactness
Stroma.Nuclei.StdDevCompactness
Stroma.Nuclei.MaxDensity
Stroma.Nuclei.MeanDensity
Stroma.Nuclei.MinDensity
Stroma.Nuclei.StdDevDensity
Stroma.Nuclei.MaxDiff.ofenclosing.e
Stroma.Nuclei.MeanDiff.ofenclosing.
Stroma.Nuclei.MinDiff.ofenclosing.e
Stroma.Nuclei.StdDevDiff.ofenclosin
Stroma.Nuclei.MaxEllipticFit
Stroma.Nuclei.MeanEllipticFit
Stroma.Nuclei.MinEllipticFit
Stroma.Nuclei.StdDevEllipticFit
Stroma.Nuclei.MaxLengthPxl
Stroma.Nuclei.MeanLengthPxl
Stroma.Nuclei.MinLengthPxl
Stroma.Nuclei.StdDevLengthPxl
Stroma.Nuclei.SumLengthPxl
Stroma.Nuclei.MaxMax.Diff.
Stroma.Nuclei.MeanMax.Diff.
Stroma.Nuclei.MinMax.Diff.
Stroma.Nuclei.StdDevMax.Diff.
Stroma.Nuclei.MaxMeanChannel1
Stroma.Nuclei.MeanMeanChannel1
Stroma.Nuclei.MinMeanChannel1

TABLE 1-continued

Morphometric Features
Script v1.0 (496 Features)

Feature

Stroma.Nuclei.StdDevMeanChannel1
Stroma.Nuclei.MaxMeanChannel2
Stroma.Nuclei.MeanMeanChannel2
Stroma.Nuclei.MinMeanChannel2
Stroma.Nuclei.StdDevMeanChannel2
Stroma.Nuclei.MaxMeanChannel3
Stroma.Nuclei.MeanMeanChannel3
Stroma.Nuclei.MinMeanChannel3
Stroma.Nuclei.StdDevMeanChannel3
Stroma.Nuclei.MaxRadiusoflargestenc
Stroma.Nuclei.MeanRadiusoflargesten
Stroma.Nuclei.MinRadiusoflargestenc
Stroma.Nuclei.StdDevRadiusoflargest
Stroma.Nuclei.MaxRadiusofsmallesten
Stroma.Nuclei.MeanRadiusofsmalleste
Stroma.Nuclei.MinRadiusofsmallesten
Stroma.Nuclei.StdDevRadiusofsmalles
Stroma.Nuclei.MaxStdevChannel1
Stroma.Nuclei.MeanStdevChannel1
Stroma.Nuclei.MinStdevChannel1
Stroma.Nuclei.StdDevStdevChannel1
Stroma.Nuclei.MaxStdevChannel2
Stroma.Nuclei.MeanStdevChannel2
Stroma.Nuclei.MinStdevChannel2
Stroma.Nuclei.StdDevStdevChannel2
Stroma.Nuclei.MaxStdevChannel3
Stroma.Nuclei.MeanStdevChannel3
Stroma.Nuclei.MinStdevChannel3
Stroma.Nuclei.StdDevStdevChannel3
Stroma.Nuclei.MaxWidthPxl
Stroma.Nuclei.MeanWidthPxl
Stroma.Nuclei.MinWidthPxl
Stroma.Nuclei.StdDevWidthPxl
C2EN
EN2SN
L2Core
C2L
CEN2L

TABLE 2

Morphometric Features
Script v2.0 (350 features)

Feature

Artifact Mean Area Pxl
Artifact StdDev Area Pxl
Artifact Mean Asymmetry
Artifact StdDev Asymmetry
Artifact Mean Border index
Artifact StdDev Border index
Artifact Mean Border length Pxl
Artifact StdDev Border length Pxl
Artifact Mean Brightness
Artifact StdDev Brightness
Artifact Mean Compactness
Artifact StdDev Compactness
Artifact Mean Density
Artifact StdDev Density
Artifact Mean Diff. of enclosing/enclosed ellipse
Artifact StdDev Diff. of enclosing/enclosed ellipse
Artifact Mean Elliptic Fit
Artifact StdDev Elliptic Fit
Artifact Mean Length Pxl
Artifact StdDev Length Pxl
Artifact Mean Length/width
Artifact StdDev Length/width
Artifact Mean Main direction
Artifact StdDev Main direction
Artifact Mean Max.Diff.

TABLE 2-continued

Morphometric Features
Script v2.0 (350 features)

Feature

Artifact StdDev Max.Diff.
Artifact Mean Mean Channel 1
Artifact StdDev Mean Channel 1
Artifact Mean Mean Channel 2
Artifact StdDev Mean Channel 2
Artifact Mean Mean Channel 3
Artifact StdDev Mean Channel 3
Artifact Mean Radius of largest enclosed ellipse
Artifact StdDev Radius of largest enclosed ellipse
Artifact Mean Radius of smallest enclosing ellipse
Artifact StdDev Radius of smallest enclosing ellipse
Artifact Mean Rectangular Fit
Artifact StdDev Rectangular Fit
Artifact Mean Shape index
Artifact StdDev Shape index
Artifact Mean Stddev Channel 1
Artifact StdDev Stddev Channel 1
Artifact Mean Stddev Channel 2
Artifact StdDev Stddev Channel 2
Artifact Mean Stddev Channel 3
Artifact StdDev Stddev Channel 3
Artifact Mean Width Pxl
Artifact StdDev Width Pxl
Cytoplasm Mean Area Pxl
Cytoplasm StdDev Area Pxl
Cytoplasm Mean Asymmetry
Cytoplasm StdDev Asymmetry
Cytoplasm Mean Border index
Cytoplasm StdDev Border index
Cytoplasm Mean Border length Pxl
Cytoplasm StdDev Border length Pxl
Cytoplasm Mean Brightness
Cytoplasm StdDev Brightness
Cytoplasm Mean Compactness
Cytoplasm StdDev Compactness
Cytoplasm Mean Density
Cytoplasm StdDev Density
Cytoplasm Mean Diff. of enclosing/enclosed ellipse
Cytoplasm StdDev Diff. of enclosing/enclosed ellipse
Cytoplasm Mean Elliptic Fit
Cytoplasm StdDev Elliptic Fit
Cytoplasm Mean Length Pxl
Cytoplasm StdDev Length Pxl
Cytoplasm Mean Length/width
Cytoplasm StdDev Length/width
Cytoplasm Mean Main direction
Cytoplasm StdDev Main direction
Cytoplasm Mean Max.Diff.
Cytoplasm StdDev Max.Diff.
Cytoplasm Mean Mean Channel 1
Cytoplasm StdDev Mean Channel 1
Cytoplasm Mean Mean Channel 2
Cytoplasm StdDev Mean Channel 2
Cytoplasm Mean Mean Channel 3
Cytoplasm StdDev Mean Channel 3
Cytoplasm Mean Radius of largest enclosed ellipse
Cytoplasm StdDev Radius of largest enclosed ellipse
Cytoplasm Mean Radius of smallest enclosing ellipse
Cytoplasm StdDev Radius of smallest enclosing ellipse
Cytoplasm Mean Rectangular Fit
Cytoplasm StdDev Rectangular Fit
Cytoplasm Mean Shape index
Cytoplasm StdDev Shape index
Cytoplasm Mean Stddev Channel 1
Cytoplasm StdDev Stddev Channel 1
Cytoplasm Mean Stddev Channel 2
Cytoplasm StdDev Stddev Channel 2
Cytoplasm Mean Stddev Channel 3
Cytoplasm StdDev Stddev Channel 3
Cytoplasm Mean Width Pxl
Cytoplasm StdDev Width Pxl
Epithelial Nuclei Mean Area Pxl
Epithelial Nuclei StdDev Area Pxl
Epithelial Nuclei Mean Asymmetry TABLE 2-continued Morphometric Features
Script v2.0 (350 features)

Feature

Epithelial Nuclei StdDev Asymmetry
Epithelial Nuclei Mean Border index
Epithelial Nuclei StdDev Border index
Epithelial Nuclei Mean Border length Pxl
Epithelial Nuclei StdDev Border length Pxl
Epithelial Nuclei Mean Brightness
Epithelial Nuclei StdDev Brightness
Epithelial Nuclei Mean Compactness
Epithelial Nuclei StdDev Compactness
Epithelial Nuclei Mean Density
Epithelial Nuclei StdDev Density
Epithelial Nuclei Mean Diff. of enclosing/enclosed ellipse
Epithelial Nuclei StdDev Diff. of enclosing/enclosed ellipse
Epithelial Nuclei Mean Elliptic Fit
Epithelial Nuclei StdDev Elliptic Fit
Epithelial Nuclei Mean Length Pxl
Epithelial Nuclei StdDev Length Pxl
Epithelial Nuclei Mean Length/width
Epithelial Nuclei StdDev Length/width
Epithelial Nuclei Mean Main direction
Epithelial Nuclei StdDev Main direction
Epithelial Nuclei Mean Max.Diff.
Epithelial Nuclei StdDev Max.Diff.
Epithelial Nuclei Mean Mean Channel 1
Epithelial Nuclei StdDev Mean Channel 1
Epithelial Nuclei Mean Mean Channel 2
Epithelial Nuclei StdDev Mean Channel 2
Epithelial Nuclei Mean Mean Channel 3
Epithelial Nuclei StdDev Mean Channel 3
Epithelial Nuclei Mean Radius of largest enclosed ellipse
Epithelial Nuclei StdDev Radius of largest enclosed ellipse
Epithelial Nuclei Mean Radius of smallest enclosing ellipse
Epithelial Nuclei StdDev Radius of smallest enclosing ellipse
Epithelial Nuclei Mean Rectangular Fit
Epithelial Nuclei StdDev Rectangular Fit
Epithelial Nuclei Mean Shape index
Epithelial Nuclei StdDev Shape index
Epithelial Nuclei Mean Stddev Channel 1
Epithelial Nuclei StdDev Stddev Channel 1
Epithelial Nuclei Mean Stddev Channel 2
Epithelial Nuclei StdDev Stddev Channel 2
Epithelial Nuclei Mean Stddev Channel 3
Epithelial Nuclei StdDev Stddev Channel 3
Epithelial Nuclei Mean Width Pxl
Epithelial Nuclei StdDev Width Pxl
Lumen Mean Area Pxl
Lumen StdDev Area Pxl
Lumen Mean Asymmetry
Lumen StdDev Asymmetry
Lumen Mean Border index
Lumen StdDev Border index
Lumen Mean Border length Pxl
Lumen StdDev Border length Pxl
Lumen Mean Brightness
Lumen StdDev Brightness
Lumen Mean Compactness
Lumen StdDev Compactness
Lumen Mean Density
Lumen StdDev Density
Lumen Mean Diff. of enclosing/enclosed ellipse
Lumen StdDev Diff. of enclosing/enclosed ellipse
Lumen Mean Elliptic Fit
Lumen StdDev Elliptic Fit
Lumen Mean Length Pxl
Lumen StdDev Length Pxl
Lumen Mean Length/width
Lumen StdDev Length/width
Lumen Mean Main direction
Lumen StdDev Main direction
Lumen Mean Max.Diff.
Lumen StdDev Max.Diff.
Lumen Mean Mean Channel 1
Lumen StdDev Mean Channel 1
Lumen Mean Mean Channel 2

TABLE 2-continued

Morphometric Features
Script v2.0 (350 features)

Feature

Lumen StdDev Mean Channel 2
Lumen Mean Mean Channel 3
Lumen StdDev Mean Channel 3
Lumen Mean Radius of largest enclosed ellipse
Lumen StdDev Radius of largest enclosed ellipse
Lumen Mean Radius of smallest enclosing ellipse
Lumen StdDev Radius of smallest enclosing ellipse
Lumen Mean Rectangular Fit
Lumen StdDev Rectangular Fit
Lumen Mean Shape index
Lumen StdDev Shape index
Lumen Mean Stddev Channel 1
Lumen StdDev Stddev Channel 1
Lumen Mean Stddev Channel 2
Lumen StdDev Stddev Channel 2
Lumen Mean Stddev Channel 3
Lumen StdDev Stddev Channel 3
Lumen Mean Width Pxl
Lumen StdDev Width Pxl
Stroma Mean Area Pxl
Stroma StdDev Area Pxl
Stroma Mean Asymmetry
Stroma StdDev Asymmetry
Stroma Mean Border index
Stroma StdDev Border index
Stroma Mean Border length Pxl
Stroma StdDev Border length Pxl
Stroma Mean Brightness
Stroma StdDev Brightness
Stroma Mean Compactness
Stroma StdDev Compactness
Stroma Mean Density
Stroma StdDev Density
Stroma Mean Diff. of enclosing/enclosed ellipse
Stroma StdDev Diff. of enclosing/enclosed ellipse
Stroma Mean Elliptic Fit
Stroma StdDev Elliptic Fit
Stroma Mean Length Pxl
Stroma StdDev Length Pxl
Stroma Mean Length/width
Stroma StdDev Length/width
Stroma Mean Main direction
Stroma StdDev Main direction
Stroma Mean Max.Diff.
Stroma StdDev Max.Diff.
Stroma Mean Mean Channel 1
Stroma StdDev Mean Channel 1
Stroma Mean Mean Channel 2
Stroma StdDev Mean Channel 2
Stroma Mean Mean Channel 3
Stroma StdDev Mean Channel 3
Stroma Mean Radius of largest enclosed ellipse
Stroma StdDev Radius of largest enclosed ellipse
Stroma Mean Radius of smallest enclosing ellipse
Stroma StdDev Radius of smallest enclosing ellipse
Stroma Mean Rectangular Fit
Stroma StdDev Rectangular Fit
Stroma Mean Shape index
Stroma StdDev Shape index
Stroma Mean Stddev Channel 1
Stroma StdDev Stddev Channel 1
Stroma Mean Stddev Channel 2
Stroma StdDev Stddev Channel 2
Stroma Mean Stddev Channel 3
Stroma StdDev Stddev Channel 3
Stroma Mean Width Pxl
Stroma StdDev Width Pxl
Stroma Nuclei Mean Area Pxl
Stroma Nuclei StdDev Area Pxl
Stroma Nuclei Mean Asymmetry
Stroma Nuclei StdDev Asymmetry
Stroma Nuclei Mean Border index
Stroma Nuclei StdDev Border index
Stroma Nuclei Mean Border length Pxl

TABLE 2-continued

Morphometric Features
Script v2.0 (350 features)

Feature

Stroma Nuclei StdDev Border length Pxl
Stroma Nuclei Mean Brightness
Stroma Nuclei StdDev Brightness
Stroma Nuclei Mean Compactness
Stroma Nuclei StdDev Compactness
Stroma Nuclei Mean Density
Stroma Nuclei StdDev Density
Stroma Nuclei Mean Diff. of enclosing/enclosed ellipse
Stroma Nuclei StdDev Diff. of enclosing/enclosed ellipse
Stroma Nuclei Mean Elliptic Fit
Stroma Nuclei StdDev Elliptic Fit
Stroma Nuclei Mean Length Pxl
Stroma Nuclei StdDev Length Pxl
Stroma Nuclei Mean Length/width
Stroma Nuclei StdDev Length/width
Stroma Nuclei Mean Main direction
Stroma Nuclei StdDev Main direction
Stroma Nuclei Mean Max.Diff.
Stroma Nuclei StdDev Max.Diff.
Stroma Nuclei Mean Mean Channel 1
Stroma Nuclei StdDev Mean Channel 1
Stroma Nuclei Mean Mean Channel 2
Stroma Nuclei StdDev Mean Channel 2
Stroma Nuclei Mean Mean Channel 3
Stroma Nuclei StdDev Mean Channel 3
Stroma Nuclei Mean Radius of largest enclosed ellipse
Stroma Nuclei StdDev Radius of largest enclosed ellipse
Stroma Nuclei Mean Radius of smallest enclosing ellipse
Stroma Nuclei StdDev Radius of smallest enclosing ellipse
Stroma Nuclei Mean Rectangular Fit
Stroma Nuclei StdDev Rectangular Fit
Stroma Nuclei Mean Shape index
Stroma Nuclei StdDev Shape index
Stroma Nuclei Mean Stddev Channel 1
Stroma Nuclei StdDev Stddev Channel 1
Stroma Nuclei Mean Stddev Channel 2
Stroma Nuclei StdDev Stddev Channel 2
Stroma Nuclei Mean Stddev Channel 3
Stroma Nuclei StdDev Stddev Channel 3
Stroma Nuclei Mean Width Pxl
Stroma Nuclei StdDev Width Pxl
Area of Artifact Pxl
Area of Cytoplasm Pxl
Area of Epithelial Nuclei Pxl
Area of Lumen Pxl
Area of Red Blood Cell Pxl
Area of Stroma Pxl
Area of Stroma Nuclei Pxl
Number of objects of Artifact
Number of objects of Cytoplasm
Number of objects of Epithelial Nuclei
Number of objects of Lumen

TABLE 2-continued

Morphometric Features
Script v2.0 (350 features)

Feature

Number of objects of Red Blood Cell
Number of objects of Stroma
Number of objects of Stroma Nuclei
Red Blood Cell Mean Area Pxl
Red Blood Cell StdDev Area Pxl
Red Blood Cell Mean Asymmetry
Red Blood Cell StdDev Asymmetry
Red Blood Cell Mean Border index
Red Blood Cell StdDev Border index
Red Blood Cell Mean Border length Pxl
Red Blood Cell StdDev Border length Pxl
Red Blood Cell Mean Brightness
Red Blood Cell StdDev Brightness
Red Blood Cell Mean Compactness
Red Blood Cell StdDev Compactness
Red Blood Cell Mean Density
Red Blood Cell StdDev Density
Red Blood Cell Mean Diff. of enclosing/enclosed ellipse
Red Blood Cell StdDev Diff. of enclosing/enclosed ellipse
Red Blood Cell Mean Elliptic Fit
Red Blood Cell StdDev Elliptic Fit
Red Blood Cell Mean Length Pxl
Red Blood Cell StdDev Length Pxl
Red Blood Cell Mean Length/width
Red Blood Cell StdDev Length/width
Red Blood Cell Mean Main direction
Red Blood Cell StdDev Main direction
Red Blood Cell Mean Max.Diff.
Red Blood Cell StdDev Max.Diff.
Red Blood Cell Mean Mean Channel 1
Red Blood Cell StdDev Mean Channel 1
Red Blood Cell Mean Mean Channel 2
Red Blood Cell StdDev Mean Channel 2
Red Blood Cell Mean Mean Channel 3
Red Blood Cell StdDev Mean Channel 3
Red Blood Cell Mean Radius of largest enclosed ellipse
Red Blood Cell StdDev Radius of largest enclosed ellipse
Red Blood Cell Mean Radius of smallest enclosing ellipse
Red Blood Cell StdDev Radius of smallest enclosing ellipse
Red Blood Cell Mean Rectangular Fit
Red Blood Cell StdDev Rectangular Fit
Red Blood Cell Mean Shape index
Red Blood Cell StdDev Shape index
Red Blood Cell Mean Stddev Channel 1
Red Blood Cell StdDev Stddev Channel 1
Red Blood Cell Mean Stddev Channel 2
Red Blood Cell StdDev Stddev Channel 2
Red Blood Cell Mean Stddev Channel 3
Red Blood Cell StdDev Stddev Channel 3
Red Blood Cell Mean Width Pxl
Red Blood Cell StdDev Width Pxl

TABLE 10

Morphometric Features -
Script v5.0 (38 features)

| Feature Name | Description |
|---|---|
| CytoplasmMeanMeanChannel40058 | Mean cytoplasm intensity value in the red color channel |
| CytoplasmMeanMeanChannel50059 | Mean cytoplasm intensity value in the green color channel |
| CytoplasmMeanMeanChannel60060 | Mean cytoplasm intensity value in the blue color channel |
| CytoplasmMeanStddevChannel40066 | Mean cytoplasm intensity standard deviation in the red color channel. |
| CytoplasmMeanStddevChannel50067 | Mean cytoplasm intensity standard deviation in the green color channel |
| CytoplasmMeanStddevChannel60068 | Mean cytoplasm intensity standard deviation in the blue color channel |
| CytoplasmStddevMeanChannel40081 | Standard deviation of cytoplasm intensity in the red color channel |
| CytoplasmStddevMeanChannel50082 | Standard deviation of cytoplasm intensity in the green color channel |
| CytoplasmStddevMeanChannel60083 | Standard deviation of cytoplasm intensity in the blue color channel |
| EpithelialNucleiMeanAreaPxl0101 | Mean value of the epithelial nuclei area, pixels |
| EpithelNucleiMeanMeanChanne40112 | Mean epithelial nuclei intensity in the red color channel |

TABLE 10-continued

Morphometric Features - Script v5.0 (38 features)

| Feature Name | Description |
| --- | --- |
| EpithelNucleiMeanMeanChanne50113 | Mean epithelial nuclei intensity in the green color channel |
| EpithelNucleiMeanMeanChanne60114 | Mean epithelial nuclei intensity in the blue color channel |
| EpitheNucleiMeanStddevChann40120 | Mean epithelial nuclei intensity standard deviation in the red color channel |
| EpitheNucleiMeanStddevChann50121 | Mean epithelial nuclei intensity standard deviation in the green color channel |
| EpitheNucleiMeanStddevChann60122 | Mean epithelial nuclei intensity standard deviation in the blue color channel |
| EpitheliaNucleiStddevAreaPxl0124 | Standard deviation of the epithelial nuclei area |
| EpitheNucleiStddevMeanChann40135 | Standard deviation of epithelial nuclei intensity in the red color channel |
| EpitheNucleiStddevMeanChann50136 | Standard deviation of epithelial nuclei intensity in the green color channel |
| EpitheNucleiStddevMeanChann60137 | Standard deviation of epithelial nuclei intensity in the blue color channel |
| StromaMeanMeanChannel40262 | Mean stroma intensity in the red color channel |
| StromaMeanMeanChannel50263 | Mean stroma intensity in the green color channel |
| StromaMeanMeanChannel60264 | Mean stroma intensity in the blue color channel |
| StromaMeanStddevChannel40270 | Mean stroma intensity standard deviation in the red color channel |
| StromaMeanStddevChannel50271 | Mean stroma intensity standard deviation in the green color channel |
| StromaMeanStddevChannel60272 | Mean stroma intensity standard deviation in the blue color channel |
| StromaStddevMeanChannel40331 | Standard deviation of stroma intensity in the red color channel |
| StromaStddevMeanChannel50332 | Standard deviation of stroma intensity in the green color channel |
| StromaStddevMeanChannel60333 | Standard deviation of stroma intensity, in the blue color channel |
| AreaOfCytoplasmPxl0345 | Total area of cytoplasm, pixels |
| AreaOfEpithelialNucleiPxl0350 | Total area of epithelial nuclei, pixels |
| AreaOfLumenPxl0357 | Total area of lumens, pixels |
| NumberOfObjectOfEpitheNuclei0364 | Total number of epithelial nuclei objects |
| AreaCytopdivTotTissueArea | Relative area of cytoplasm with respect to the tissue area, % |
| AreaEpitNucdivTotTissueArea | Relative area of epithelial nuclei with respect to the tissue area, % |
| AreaLumendivTotTissueArea | Relative area of lumens with respect to the tissue area, % |
| AreaStromadivTotTissueArea | Relative area of stroma with respect to the tissue area, % |
| NumObjEpitNucdivTotNumberNuc | Relative number of epithelial nuclei with respect to the total number of nuclei |

TABLE 11

Morphometric Features

| Feature Name | Description |
| --- | --- |
| CytoplasmMeanMeanChannel40058 | Mean of cytoplasm intensity mean value with the red filter |
| CytoplasmMeanMeanChannel50059 | Mean of cytoplasm intensity mean value with the green filter |
| CytoplasmMeanMeanChannel60060 | Mean of cytoplasm intensity mean value with the blue filter |
| CytoplasmMeanStddevChannel40066 | Mean of cytoplasm intensity standard deviation with the red filter |
| CytoplasmMeanStddevChannel50067 | Mean of cytoplasm intensity standard deviation with the green filter |
| CytoplasmMeanStddevChannel60068 | Mean of cytoplasm intensity standard deviation with the blue filter |
| CytoplasmStddevMeanChannel40081 | Standard deviation of the mean cytoplasm intensity with the red filter |
| CytoplasmStddevMeanChannel50082 | Standard deviation of the mean cytoplasm intensity with the green filter |
| CytoplasmStddevMeanChannel60083 | Standard deviation of the mean cytoplasm intensity with the blue filter |
| EpithelNucleiMeanMeanChanne40112 | Mean of epithelial nuclei intensity with the red filter |
| EpithelNucleiMeanMeanChanne50113 | Mean of epithelial nuclei intensity with the green filter |
| EpithelNucleiMeanMeanChanne60114 | Mean of epithelial nuclei intensity with the blue filter |
| EpitheNucleiMeanStddevChann40120 | Mean of epithelial nuclei intensity standard deviation with the red filter |
| EpitheNucleiMeanStddevChann50121 | Mean of epithelial nuclei intensity standard deviation with the green filter |
| EpitheNucleiMeanStddevChann60122 | Mean of epithelial nuclei intensity standard deviation with the blue filter |
| EpitheliaNucleiStddevAreaPxl0124 | Standard deviation of the epithelial nuclei area |
| EpitheNucleiStddevMeanChann40135 | Standard deviation of the mean epithelial nuclei intensity with the red filter |
| EpitheNucleiStddevMeanChann50136 | Standard deviation of the mean epithelial nuclei intensity with the green filter |
| EpitheNucleiStddevMeanChann60137 | Standard deviation of the mean epithelial nuclei intensity with the blue filter |
| StromaMeanMeanChannel40262 | Mean of stroma intensity with the red filter |
| StromaMeanMeanChannel50263 | Mean of stroma intensity with the green filter |
| StromaMeanMeanChannel60264 | Mean of stroma intensity with the blue filter |
| StromaMeanStddevChannel40270 | Mean of stroma intensity standard deviation with the red filter |
| StromaMeanStddevChannel50271 | Mean of stroma intensity standard deviation with the green filter |
| StromaMeanStddevChannel60272 | Mean of stroma intensity standard deviation with the blue filter |
| StromaStddevMeanChannel40331 | Standard deviation of the mean stroma intensity with the red filter |
| StromaStddevMeanChannel50332 | Standard deviation of the mean stroma intensity with the green filter |
| StromaStddevMeanChannel60333 | Standard deviation of the stroma intensity with the blue filter |
| AreaCytopdivTotTissueArea | Area of cytoplasm relative to the tissue area, % |
| AreaEpitNucdivTotTissueArea | Area of epithelial nuclei relative to the tissue area, % |
| AreaLumendivTotTissueArea | Area of lumen relative to the tissue area, % |
| AreaRBCdivTotTissueArea | Area of red blood cells relative to the tissue area, % |
| AreaStromadivTotTissueArea | Area of stroma relative to the tissue area, % |

What is claimed is:

1. Apparatus for evaluating a risk of prostate cancer recurrence in a patient, the apparatus comprising:
a model predictive of prostate cancer recurrence configured to evaluate a dataset for a patient to thereby evaluate a risk of prostate cancer recurrence in the patient, wherein the model is based on at least the following features:
seminal vesicle involvement;
a measurement of androgen receptor (AR); and
a morphometric measurement of epithelial nuclei derived from a tissue image.

2. The apparatus of claim 1, wherein the model is further based on a biopsy Gleason score.

3. The apparatus of claim 1, wherein the apparatus comprises an output device for outputting a value indicative of the patient's risk of prostate cancer recurrence.

4. A method of evaluating a risk of prostate cancer recurrence in a patient, the method comprising:
evaluating a dataset for a patient with a model predictive of prostate cancer recurrence, wherein the model is based on at least the following features: seminal vesicle involvement, a measurement of androgen receptor (AR), and a morphometric measurement of epithelial nuclei derived from a tissue image,
thereby evaluating the risk of prostate cancer recurrence in the patient.

5. The method of claim 4, wherein the model is further based on a biopsy Gleason score.

6. The method of claim 4, further comprising outputting a value indicative of the patient's risk of prostate cancer recurrence.

7. A computer-readable medium comprising computer executable instructions recorded thereon for performing the method comprising:
evaluating a dataset for a patient with a model predictive of prostate cancer recurrence to thereby evaluate the risk of prostate cancer recurrence in the patient, wherein the model is based on at least the following features: seminal vesicle involvement, a measurement of androgen receptor (AR), and a morphometric measurement of epithelial nuclei derived from a tissue image.

8. An apparatus for evaluating a risk of clinical failure in a patient subsequent to the patient having a radical prostatectomy, the apparatus comprising:
a model predictive of clinical failure configured to evaluate a dataset for a patient to thereby evaluate a risk of clinical failure for the patient, wherein the model is based on at least the following features:
lymph node involvement;
a morphometric measurement of cytoplasm derived from a tissue image; and
a measurement of intensity of androgen receptor (AR) in epithelial cells.

9. The apparatus of claim 8, wherein the feature of intensity of androgen receptor (AR) in epithelial cells is generated based on computer analysis of a tissue image showing immunofluorescence.

10. A method of evaluating a risk of clinical failure in a patient subsequent to the patient having a radical prostatectomy, the method comprising:
evaluating a dataset for a patient with a model predictive of clinical failure post-prostatectomy, wherein the model is based on at least the following features: lymph node involvement, a morphometric measurement of cytoplasm derived from a tissue image, and a measurement of intensity of androgen receptor (AR) in epithelial cells,
thereby evaluating the risk of clinical failure in the patient.

11. The method of claim 10, wherein the feature of intensity of androgen receptor (AR) in epithelial cells is generated based on computer analysis of a tissue image-showing immunofluorescence.

12. A computer-readable medium comprising computer executable instructions recorded thereon for performing the method comprising:
evaluating a dataset for a patient with a model predictive of clinical failure post-prostatectomy to thereby evaluate the risk of clinical failure in the patient, wherein the model is based on at least the following features: lymph node involvement, a morphometric measurement of cytoplasm derived from a tissue image, and a measurement of intensity of androgen receptor (AR) in epithelial cells.

13. The computer-readable medium of claim 12, wherein the feature of intensity of androgen receptor (AR) in epithelial cells is generated based on computer analysis of a tissue image showing immunofluorescence.

14. The apparatus of claim 1, wherein the measurement of androgen receptor (AR) is generated based on computer analysis of a tissue image showing immunofluorescence (IF).

15. The apparatus of claim 14, wherein the measurement of androgen receptor (AR) comprises the relative area of epithelial nuclei with AR positive with respect to total epithelial nuclei area.

16. The method of claim 4, wherein the measurement of androgen receptor (AR) is generated based on computer analysis of a tissue image showing immunofluorescence (IF).

17. The method of claim 16, wherein the measurement of androgen receptor (AR) comprises the relative area of epithelial nuclei with AR positive with respect to total epithelial nuclei area.

18. The computer-readable medium of claim 7, wherein the measurement of androgen receptor (AR) is generated based on computer analysis of a tissue image showing immunofluorescence (IF).

19. The computer-readable medium of claim 18, wherein the measurement of androgen receptor (AR) comprises the relative area of epithelial nuclei with AR positive with respect to total epithelial nuclei area.

20. The computer-readable medium of claim 7, wherein the model is further based on a biopsy Gleason score.

21. The computer-readable medium of claim 7, further comprising computer executable instructions recorded thereon for outputting a value indicative of the patient's risk of prostate cancer recurrence.

22. A method of evaluating a risk of occurrence of a medical condition in a patient, the method comprising:
receiving a patient dataset for the patient; and
evaluating the patient dataset with a model predictive of the medical condition to produce a value indicative of the risk of occurrence of the medical condition in the patient, wherein the model is based on one or more clinical feature(s), one or more molecular feature(s) generated based on computer analysis of one or more tissue images showing immunofluorescence (IF), and one or more computer-generated morphometric feature(s) generated from one or more tissue image(s).

23. The method of claim 22, further comprising generating with a computer the one or more molecular feature(s) for the patient for inclusion in the patient dataset comprising:
acquiring at least one antigen-specific tissue image for the patient based on a spectral profile of at least one fluorochrome; and
using the computer to take one or more measurements from the at least one antigen-specific tissue image.

24. The method of claim 22, further comprising generating with a computer the one or more morphometric feature(s) for the patient for inclusion in the patient dataset comprising:
   segmenting the tissue image into one or more objects;
   classifying the one or more objects into one or more object classes; and
   determining the morphometric feature(s) by taking one or more measurements for the one or more object classes.

25. The method of claim 24, wherein said classifying the one or more objects into one or more object classes comprises classifying each object into a class from the group of classes consisting of stroma, cytoplasm, epithelial nuclei, stroma nuclei, lumen, red blood cell, tissue artifact, and tissue background.

26. An apparatus for evaluating the risk of occurrence of a medical condition in a patient, the apparatus comprising:
   a model predictive of the medical condition, wherein the model is based on one or more clinical feature(s), one or more molecular feature(s) generated based on computer analysis of one or more tissue images showing immunofluorescence (IF), and one or more computer-generated morphometric feature(s) generated from one or more tissue image(s), wherein the model is configured to:
   receive a patient dataset for the patient; and
   evaluate the patient dataset according to the model to produce a value indicative of the risk of occurrence of the medical condition in the patient.

27. The apparatus of claim 26, further comprising a computer for generating the one or more molecular feature(s) for the patient for inclusion in the patient dataset, wherein the computer is configured to take one or more measurements from at least one antigen-specific tissue image acquired for the patient based on a spectral profile of at least one fluorochrome.

28. The apparatus of claim 26, further comprising an image processing tool configured to generate the one or more morphometric feature(s) from a tissue image for the patient for inclusion in the patient dataset comprising:
   segmenting the tissue image into one or more objects with the image processing tool;
   classifying the one or more objects into one or more object classes by the image processing tool; and
   determining the morphometric features by taking one or more measurements for the one or more object classes with the image processing tool.

29. The apparatus of claim 27, wherein said classifying the one or more objects into one or more object classes by the image processing tool comprises classifying by the image processing tool each of one or more of the objects into a class from the group of classes consisting of stroma, cytoplasm, epithelial nuclei, stroma nuclei, lumen, red blood cell, tissue artifact, and tissue background.

30. A computer-readable medium comprising computer executable instructions recorded thereon for performing the method comprising:
   receiving a patient dataset for a patient; and
   evaluating the patient dataset with a model predictive of a medical condition to produce a value indicative of the risk of occurrence of the medical condition in the patient, wherein the model is based on one or more clinical feature(s), one or more molecular feature(s) generated based on computer analysis of one or more tissue images showing immunofluorescence (IF), and one or more computer-generated morphometric feature(s) generated from one or more tissue image(s).

31. The computer-readable medium of claim 30, further comprising computer executable instructions recorded thereon for generating with a computer the one or more molecular feature(s) for the patient for inclusion in the patient dataset comprising:
   acquiring at least one antigen-specific tissue image for the patient based on a spectral profile of at least one fluorochrome; and
   using the computer to take one or more measurements from the at least one antigen-specific tissue image.

32. The computer-readable medium of claim 30, further comprising computer executable instructions recorded thereon for generating with a computer the one or more morphometric feature(s) from a tissue image for the patient for inclusion in the patient dataset comprising:
   segmenting the tissue image into one or more objects;
   classifying the one or more objects into one or more object classes; and
   determining the morphometric feature(s) by taking one or more measurements for the one or more object classes.

33. The computer readable medium of claim 32, wherein said classifying the one or more objects into one or more object classes comprises classifying each object into a class from the group of classes consisting of stroma, cytoplasm, epithelial nuclei, stroma nuclei, lumen, red blood cell, tissue artifact, and tissue background.

* * * * *